(12) United States Patent
Chakraborty et al.

(10) Patent No.: US 11,904,031 B2
(45) Date of Patent: Feb. 20, 2024

(54) ORTHODONTIC ARTICLES COMPRISING POLYMERIZED COMPOSITION COMPRISING AT LEAST TWO FREE-RADICAL INITIATORS

(71) Applicant: 3M INNOVATIVE PROPERTIES COMPANY, St. Paul, MN (US)

(72) Inventors: Saswata Chakraborty, Cottage Grove, MN (US); Benjamin C. MacMurray, St. Paul, MN (US); Eric W. Nelson, Stillwater, MN (US); Thomas P. Klun, Lakeland, MN (US); Richard J. Pokorny, Maplewood, MN (US); Wayne S. Mahoney, St. Paul, MN (US); Chad M. Amb, Roberts, WI (US); George W. Griesgraber, Eagan, MN (US); Dana R. Reed, Minneapolis, MN (US); Ahmed S. Abuelyaman, Woodbury, MN (US); Robert S. Clough, St. Paul, MN (US); James D. Hansen, White Bear Lake, MN (US); Daniel J. Skamser, Ham Lake, MN (US); Ian Dailey, Maplewood, MN (US); John M. Riedesel, San Jose, CA (US)

(73) Assignee: 3M Innovative Properties Company, St. Paul, MN (US)

( * ) Notice: Subject to any disclaimer, the term of this patent is extended or adjusted under 35 U.S.C. 154(b) by 944 days.

(21) Appl. No.: 16/754,186

(22) PCT Filed: Nov. 20, 2018

(86) PCT No.: PCT/US2018/062085
§ 371 (c)(1),
(2) Date: Apr. 7, 2020

(87) PCT Pub. No.: WO2019/104079
PCT Pub. Date: May 31, 2019

(65) Prior Publication Data
US 2021/0186820 A1 Jun. 24, 2021

Related U.S. Application Data

(60) Provisional application No. 62/736,027, filed on Sep. 25, 2018, provisional application No. 62/736,031, (Continued)

(51) Int. Cl.
A61K 6/62 (2020.01)
A61C 7/08 (2006.01)
(Continued)

(52) U.S. Cl.
CPC ............... *A61K 6/62* (2020.01); *A61C 7/002* (2013.01); *A61C 7/08* (2013.01); *A61K 6/893* (2020.01);
(Continued)

(58) Field of Classification Search
CPC ............ A61K 6/62; A61K 6/893; A61C 7/08; A61C 7/002; C08L 75/14; B33Y 70/00; B33Y 80/00; B33Y 10/00; B29C 64/124
(Continued)

(56) References Cited

U.S. PATENT DOCUMENTS

| 3,429,722 A | 2/1969 | Economy |
| 3,795,524 A | 3/1974 | Sowman |

(Continued)

FOREIGN PATENT DOCUMENTS

| CA | 2092131 | 9/1993 |
| CA | 3008362 | 6/2017 |

(Continued)

OTHER PUBLICATIONS

M. Azam Ali et al. "Relationship Between Physical-Mechanical Properties and Glass transition Temperatures of UV-Cured Polymers", Polymer-Plastic Technology and Engineering, (online), 37(2), 175-189, (1998) (Year: 1998).*
(Continued)

*Primary Examiner* — Michael M. Bernshteyn
(74) *Attorney, Agent, or Firm* — Adrian L. Pishko; Carolyn A. Fischer

(57) ABSTRACT

An orthodontic article is described comprising the reaction product of a free-radically polymerizable resin; a first free-
(Continued)

radical photoinitiator having sufficient absorbance at a first wavelength range; and a second free-radical initiator selected from a second photoinitiator having sufficient absorbance at a second wavelength range, wherein the second wavelength range is different than the first wavelength range, or a thermal free-radical initiator. In some embodiments, the first free-radical photoinitiator exhibits a maximum absorbance at a wavelength of the range of 370-380 nm or 320-330 nm and/or comprises photoinitiator groups selected from acyl phosphine oxide or alkyl amine acetophenone. Also described are photopolymerizable compositions and methods.

20 Claims, 7 Drawing Sheets

Related U.S. Application Data filed on Sep. 25, 2018, provisional application No. 62/692,456, filed on Jun. 29, 2018, provisional application No. 62/692,466, filed on Jun. 29, 2018, provisional application No. 62/643,431, filed on Mar. 15, 2018, provisional application No. 62/589,707, filed on Nov. 22, 2017.

(51) Int. Cl.
| | |
|---|---|
| *A61C 7/00* | (2006.01) |
| *A61K 6/893* | (2020.01) |
| *C08L 75/14* | (2006.01) |
| *B33Y 70/00* | (2020.01) |
| *B33Y 80/00* | (2015.01) |
| *B33Y 10/00* | (2015.01) |
| *B29C 64/124* | (2017.01) |

(52) U.S. Cl.
CPC ............ *B29C 64/124* (2017.08); *B33Y 10/00* (2014.12); *B33Y 70/00* (2014.12); *B33Y 80/00* (2014.12); *C08L 75/14* (2013.01)

(58) Field of Classification Search
USPC ........................................................ 523/118
See application file for complete search history.

(56) References Cited

U.S. PATENT DOCUMENTS

| | | | |
|---|---|---|---|
| 4,047,965 A | 9/1977 | Karst | |
| 4,591,626 A | 5/1986 | Kawai | |
| 4,642,126 A | 2/1987 | Zador | |
| 4,652,274 A | 3/1987 | Boettcher | |
| 4,954,462 A | 9/1990 | Wood | |
| 5,185,299 A | 2/1993 | Wood | |
| 5,462,797 A | 10/1995 | Williams | |
| 5,476,749 A | 12/1995 | Steinmann | |
| 5,573,889 A | 11/1996 | Hofmann | |
| 5,645,973 A | 7/1997 | Hofmann | |
| 5,780,154 A | 7/1998 | Okano | |
| 5,902,836 A | 5/1999 | Bennett | |
| 5,981,621 A | 11/1999 | Clark | |
| 6,017,973 A | 1/2000 | Tamura | |
| 6,025,114 A | 2/2000 | Popat | |
| 6,057,034 A | 5/2000 | Yamazaki | |
| 6,183,593 B1 | 2/2001 | Narang | |
| 6,200,732 B1 | 3/2001 | Tamura | |
| 6,572,693 B1 | 6/2003 | Wu | |
| 6,664,306 B2 | 12/2003 | Gaddem | |
| 7,015,286 B2 | 3/2006 | Heilmann | |
| 7,211,368 B2 | 5/2007 | Coats | |
| 7,622,535 B2 | 11/2009 | Dairoku | |
| 8,329,776 B2 | 12/2012 | Hecht | |
| 9,205,601 B2 | 12/2015 | DeSimone | |
| 9,295,617 B2 | 3/2016 | Eckert | |
| 9,360,757 B2 | 6/2016 | DeSimone | |
| 9,387,056 B2 | 7/2016 | Wachter | |
| 9,701,775 B2 | 7/2017 | Liu | |
| 9,777,097 B2 | 10/2017 | Liu | |
| 10,492,888 B2 | 12/2019 | Chen | |
| 2005/0090575 A1* | 4/2005 | Chaput | C04B 35/6263 523/115 |
| 2007/0031791 A1 | 2/2007 | Cinader, Jr. | |
| 2008/0248442 A1 | 10/2008 | Raby | |
| 2011/0091832 A1 | 4/2011 | Kim | |
| 2011/0183298 A1* | 7/2011 | Sun | A61K 6/62 433/223 |
| 2012/0046376 A1 | 2/2012 | Loccufier | |
| 2012/0270038 A1 | 10/2012 | Kim | |
| 2013/0078594 A1 | 3/2013 | Leslie-Martin | |
| 2013/0095446 A1 | 4/2013 | Andreiko | |
| 2013/0130203 A1 | 5/2013 | Velamakanni | |
| 2014/0131908 A1 | 5/2014 | Sun | |
| 2014/0167300 A1 | 6/2014 | Lee | |
| 2014/0239527 A1 | 8/2014 | Lee | |
| 2014/0356799 A1 | 12/2014 | Cinader, Jr. | |
| 2015/0044623 A1 | 2/2015 | Rundlett | |
| 2015/0111979 A1 | 4/2015 | Yang | |
| 2016/0167301 A1 | 6/2016 | Cole | |
| 2016/0184189 A1 | 6/2016 | Hagiwara | |
| 2016/0288479 A1 | 10/2016 | Shuey | |
| 2016/0332367 A1 | 11/2016 | Sun | |
| 2017/0007362 A1 | 1/2017 | Chen | |
| 2017/0022311 A1 | 1/2017 | Liu | |
| 2017/0151718 A1 | 6/2017 | Rolland | |
| 2020/0048392 A1 | 2/2020 | Gryska | |
| 2021/0176820 A1 | 6/2021 | Zhang | |
| 2021/0186820 A1* | 6/2021 | Chakraborty | C08G 18/8141 |
| 2021/0238328 A1* | 8/2021 | Wu | A61K 6/893 |
| 2021/0361389 A1* | 11/2021 | MacMurray | A61C 7/08 |

FOREIGN PATENT DOCUMENTS

| | | |
|---|---|---|
| CN | 104765251 | 7/2015 |
| CN | 105566916 | 5/2016 |
| EP | 0562826 | 9/1993 |
| EP | 2008636 | 12/2008 |
| EP | 2167013 | 3/2010 |
| GB | 2163443 | 2/1986 |
| GB | 2189793 | 11/1987 |
| JP | 2001302744 | 10/2001 |
| JP | 2017001226 | 1/2017 |
| WO | WO 1996-15179 | 5/1996 |
| WO | WO 1998-39374 | 9/1998 |
| WO | WO 2006-044012 | 4/2006 |
| WO | WO 2009-045752 | 4/2009 |
| WO | WO 2012-045660 | 4/2012 |
| WO | WO 2014-078537 | 5/2014 |
| WO | WO 2014-098956 | 6/2014 |
| WO | WO 2015-094842 | 6/2015 |
| WO | WO 2015-200201 | 12/2015 |
| WO | WO 2016-071811 | 5/2016 |
| WO | WO 2016-109660 | 7/2016 |
| WO | WO 2016-148960 | 9/2016 |
| WO | WO 2016-149007 | 9/2016 |
| WO | WO 2016-182444 | 11/2016 |
| WO | WO 2016-187155 | 11/2016 |
| WO | WO 2018-005501 | 1/2018 |
| WO | WO 2018-106531 | 6/2018 |
| WO | WO 2018-119026 | 6/2018 |
| WO | WO 2018-152076 | 8/2018 |
| WO | WO 2019-023009 | 1/2019 |
| WO | WO 2019-023120 | 1/2019 |
| WO | WO 2019-023166 | 1/2019 |
| WO | WO 2019-048963 | 3/2019 |
| WO | WO 2019-103855 | 5/2019 |
| WO | WO 2019-104072 | 5/2019 |
| WO | WO 2019-175716 | 9/2019 |
| WO | WO 2019-224699 | 11/2019 |
| WO | WO 2019-244007 | 12/2019 |

(56) References Cited

FOREIGN PATENT DOCUMENTS

| WO | WO 2020-005411 | 1/2020 |
|----|----------------|--------|
| WO | WO 2020-005413 | 1/2020 |
| WO | WO 2020-104873 | 5/2020 |

OTHER PUBLICATIONS

M.Azam Ali et al. "Relationship Between Physical-Mechanical Properties and Glass transition Temperatures of UV-Cured Polymers", Polymer-Plastic Technology and Engineering, (online), 37(2), 175-189 (Year: 1998).*

Ali, "Relationship Between Physical-Mechanical Properties and Glass Transition Temperatures of UV-Cured Polymers", Polymer-Plastics Technology and Engineering, vol. 37, No. 2, 1998, pp. 175-189.

Bishop, "Multiple Photoinitiators for Improved Performance", Jan. 1, 2008, Retrieved from the Internet: URL <https://www.radtech.org/proceedings/2008/papers/072.pdf>, [retrieved on Feb. 19, 2019], 8 pages, XP055558707.

Cavex LC Dental Tray, Apr. 2015, 6 pages.
CHIVACURE® 300, Chitec, May 4, 2010, 10 pages.
Ciba® IRGACURE® 369, Sep. 2001, 3 pages.
EBECRYL® 8808 Aliphatic Urethane Diacrylate, Allnex Technical Data Sheet, 2013, 2 pages.
Elles, "De Quelques Polyacrylamides", Chimie Moderne, 1959, vol. 4, No. 26, pp. 53-57.
Exothane™ Elastomers, Esstech, Inc., 4 pages.
Fang, "The influence of monobutyl itaconate and β-carboxyethyl acrylate on acrylic latex pressure sensitive adhesives", International Journal of Adhesion and Adhesives, 2018, vol. 84, pp. 387-393.
Fleischhaker, "Glass-Transition-, Melting- , and Decomposition Temperatures of Tailored Polyacrylates and Polymethacrylates: General Trends and Structure-Property Relationships", Macromolecular Chemistry and Physics, 2014, vol. 215, pp. 1192-1200.
Green, Industrial Photoinitiators, 195 (2010).
Griffin, "Calculation of HLB Values of Non-Ionic Surfactants", Journal of the Society of Cosmetic Chemists, 1954, vol. 5, pp. 249-259.
Hopfinger, "Molecular Modeling of Polymers. IV. Estimation of Glass Transition Temperatures", Journal of Polymer Science: Part B: Polymer Physics, 1988, vol. 26, pp. 2007-2028.
IRGACURE® 379 Photoinitiator, Ciba, Apr. 2002, 3 pages.
Jakubowski, "Comparison of thermomechanical properties of statistical, gradient and block copolymers of isobornyl acrylate and n-butyl acrylate with various acrylate homopolymers", Polymer, 2008, vol. 49, pp. 1567-1578.
Kuraray Polyols, Polyester Polyols, Polycarbonate Polyols, 6 pages.
Mappes, Types of Orthodontic Appliances, 6 pages.
Matsumoto, "Radical Polymerization of 4-tert-Butylcyclohexyl Methacrylate: Polymerization Kinetics and Polymer Properties", Macromolecules, 1993, vol. 26, No. 7, pp. 1659-1665.
Matsumoto, "Synthesis and Characterization of Poly(1-adamantyl methacrylate): Effects of the Adamantyl Group on Radical Polymerization Kinetics and Thermal Properties of the Polymer", Macromolecules, 1991, vol. 24, pp. 4017-4024.
Matsumoto, "Synthesis and Thermal Properties of Poly (cycloalkyl methacrylate)s Bearing Bridged- and Fused-Ring Structures", Journal of Polymer Science A:, Polymer Chemistry, 1993, vol. 31, pp. 2531-2539.
Methacrylate Resins, E.I. du Pont de Nemours & Co., Industrial and Engineering Chemistry, Oct. 1936, vol. 28, No. 10, pp. 1160-1163.
Photoinitiators for UV Curing Key Products Selection Guide 2003, Ciba, Oct. 2003, 8 pages.
Polymeric Photoinitiators: UV Inks and Coatings for Food Packaging, Radtech Report, Winter 2011, 6 pages.
Russell, "Thermal and Dynamic Mechanical Relaxation Behavior of Stereoregular Poly(2-Hydroxyethyl Methacrylate)", Journal of Polymer Science: Polymer Physics Edition, 1980, vol. 18, pp. 1271-1283.
Song, "In Vitro Evaluation of Chemically Cross-Linked Shape-Memory Acrylate Methacrylate Copolymer Networks as Ocular Implants", Journal of Physical Chemistry B, May 2010, vol. 114, No. 21, pp. 7172-7178.
SpeedCure, Lambson Technical Data Sheet, 2010, 2 pages.
Tuncay, The Invisalign System, 179-185.
Turner, "The glass transition temperature of poly(N-vinyl pyrolidone) by differential scanning calorimetry", Polymer, 1985, vol. 26, pp. 757-762.
Wei, "A Highly Efficient Polyurethane Type Polymeric Photoinitiator Containing In chain Benzophenone and Coinitiator Amine for Photopolymerization of PU Prepolymers", Macromoiecular Chemistry and Physics, Dec. 2006, vol. 207. No. 24, pp. 2321-2328.
Wilson, "Thermal Expansion of Amorphous Polymers at Atmospheric Pressure. I. Experimental", Macromolecules, Dec. 1973, vol. 6, No. 6, pp. 902-908.
International Search Report for PCT International Application No. PCT/US2018/062085, dated May 9, 2019, 9 pages.
Guo, et al., "Synthesis, characterization, and aging resistance of the polyurethane dimethacrylate layer for dental restorations", European Journal of Oral Sciences, vol. 128, (2020), pp. 89-99.

* cited by examiner

ORTHODONTIC ARTICLES COMPRISING POLYMERIZED COMPOSITION COMPRISING AT LEAST TWO FREE-RADICAL INITIATORS

CROSS REFERENCE TO RELATED APPLICATIONS

This application is a national stage filing under 35 U.S.C. 371 of PCT/US2018/062085, filed Nov. 20, 2018, which claims the benefit of U.S. Application No. 62/589,707, filed Nov. 22, 2017; U.S. Application No. 62/643,431, filed Mar. 15, 2018; U.S. Application No. 62/692,466, filed Jun. 29, 2018; U.S. Application No. 62/692,456, filed Jun. 29, 2018; U.S. Application No. 62/736,027, filed Sep. 25, 2018; U.S. Application No. 62/736,031, filed Sep. 25, 2018; PCT Application No. PCT/US2018/060014, filed Nov. 9, 2018; and U.S. Application No. 62/769,305, filed Nov. 19, 2018, the disclosures of which are incorporated by reference in their entirety herein.

TECHNICAL FIELD

The present disclosure broadly relates to dental articles (e.g. orthodontic tray aligner) including at least one free-radically polymerizable resin, such as a urethane component and at least one monofunctional reactive diluent, and methods of making the articles, such as additive manufacturing methods.

BACKGROUND

The use of stereolithography and inkjet printing to produce three-dimensional articles has been known for a relatively long time, and these processes are generally known as methods of so called 3D printing (or additive manufacturing). In vat polymerization techniques (of which stereolithography is one type), the desired 3D article is built up from a liquid, curable composition with the aid of a recurring, alternating sequence of two steps: in the first step, a layer of the liquid, curable composition, one boundary of which is the surface of the composition, is cured with the aid of appropriate radiation within a surface region which corresponds to the desired cross-sectional area of the shaped article to be formed, at the height of this layer, and in the second step, the cured layer is covered with a new layer of the liquid, curable composition, and the sequence of steps is repeated until a so-called green body (i.e., gelled article) of the desired shape is finished. This green body is often not yet fully cured and must, usually, be subjected to post-curing. The mechanical strength of the green body immediately after curing, otherwise known as green strength, is relevant to further processing of the printed articles.

Other 3D printing techniques use inks that are jetted through a print head as a liquid to form various three-dimensional articles. In operation, the print head may deposit curable photopolymers in a layer-by-layer fashion. Some jet printers deposit a polymer in conjunction with a support material or a bonding agent. In some instances, the build material is solid at ambient temperatures and converts to liquid at elevated jetting temperatures. In other instances, the build material is liquid at ambient temperatures.

One particularly attractive opportunity for 3D printing is in the direct creation of orthodontic clear tray aligners. These trays, also known as aligners or polymeric or shell appliances, are provided in a series and are intended to be worn in succession, over a period of months, in order to gradually move the teeth in incremental steps towards a desired target arrangement. Some types of clear tray aligners have a row of tooth-shaped receptacles for receiving each tooth of the patient's dental arch, and the receptacles are oriented in slightly different positions from one appliance to the next in order to incrementally urge each tooth toward its desired target position by virtue of the resilient properties of the polymeric material. A variety of methods have been proposed in the past for manufacturing clear tray aligners and other resilient appliances. Typically, positive dental arch models are fabricated for each dental arch using additive manufacturing methods such as stereolithography described above. Subsequently, a sheet of polymeric material is placed over each of the arch models and formed under heat, pressure and/or vacuum to conform to the model teeth of each model arch. The formed sheet is cleaned and trimmed as needed and the resulting arch-shaped appliance is shipped along with the desired number of other appliances to the treating professional.

An aligner or other resilient appliance created directly by 3D printing would eliminate the need to print a mold of the dental arch and further thermoform the appliance. It also would allow new aligner designs and give more degrees of freedom in the treatment plan. Exemplary methods of direct printing clear tray aligners and other resilient orthodontic apparatuses are set forth in PCT Publication Nos. WO2016/109660 (Raby et al.), WO2016/148960 (Cinader et al.), and WO2016/149007 (Oda et al.) as well as US Publication Nos. US2011/0091832 (Kim, et al.) and US2013/0095446 (Kitching).

SUMMARY

Existing printable/polymerizable resins tend to be too brittle (e.g., low elongation, short-chain crosslinked bonds, thermoset composition, and/or high glass transition temperature) for a resilient oral appliance such as an aligner. An aligner or other appliance prepared from such resins could easily break in the patient's mouth during treatment, creating material fragments that may abrade or puncture exposed tissue or be swallowed. These fractures at the very least interrupt treatment and could have serious health consequences for the patient. Thus, there is a need for curable liquid resin compositions that are tailored and well suited for creation of resilient articles using 3D printing (e.g., additive manufacturing) method. Preferably, curable liquid resin compositions to be used in the vat polymerization 3D printing process have low viscosity, a proper curing rate, and excellent mechanical properties in both the final cured article. In contrast, compositions for inkjet printing processes need to be much lower viscosity to be able to be jetted through nozzles, which is not the case for most vat polymerization resins.

Urethane (meth)acrylates are a class of raw materials that have interesting properties, for example an elongation of over 100% when cured, and very high toughness. But these resins also have a very high viscosity; at room temperature they are basically solids. Therefore, they only have been used in small amounts in photosensitive resin formulations for vat polymerization or stereolithography, and the properties of these resins are dominated by the other components.

The selection of photoinitiator can reduce the amount of extractables and/or improve the mechanical properties, such as yield strength and 3-point bend modulus.

In one embodiment, an orthodontic article is described comprising a cured composition comprising the reaction product of a free-radically polymerizable resin; a first free-radical photoinitiator having sufficient absorbance at a first wavelength range; and a second free-radical initiator selected from a second photoinitiator having sufficient absorbance at a second wavelength range, wherein the second wavelength range is different than the first wavelength range, or a thermal free-radical initiator.

In some embodiments sufficient absorbance is provided by selection of a first free-radical photoinitiator wherein a 1 g/liter acetonitrile solution, at a pathlength of 1 cm, has an absorbance of greater than 0.01, 0.02, 0.03, 0.04, 0.05, 0.06, 0.07, 0.08, 0.09, or 0.10 at a wavelength of the first wavelength range when measured with a spectrophotometer. In some embodiments, sufficient absorbance is provided by selection of a first free-radical photoinitiator wherein a 1 g/liter acetonitrile solution, at a pathlength, of 1 cm, has an absorbance of greater than 0.2, 0.3, 0.4, or 0.5 for a 1 g/liter solution of the first free-radical photoinitiator in acetonitrile at a wavelength of the first wavelength range when measured with a spectrophotometer.

In some embodiments, the first wavelength range is 375-450 nm (e.g. 385 nm).

In some embodiments, sufficient absorbance is provided by selection of a first free-radical photoinitiator that exhibits a maximum absorbance at a wavelength of the range of 370-380 nm or 320-330 nm.

In some embodiments sufficient absorbance is provided by selection of a first free-radical photoinitiator that comprises photoinitiator groups selected from acyl phosphine oxide or alkyl amine acetophenone.

In some embodiments, the second free-radical initiator is a thermal initiator. In a favored embodiment, the second thermal initiator has a 10 hours half-life at a temperature of at least 50° C. The thermal initiator typically comprises a peroxide or azo group.

In some embodiments sufficient absorbance is provided by selection of a second free-radical photoinitiator wherein a 1 g/liter acetonitrile solution, at a pathlength, has an absorbance of greater than 0.01, 0.02, 0.03, 0.04, 0.05, 0.06, 0.07, 0.08, 0.09, or 0.10 a wavelength of the second wavelength range when measured with a spectrophotometer.

In some embodiments, the second wavelength range is 360 nm up to but not including 375 nm (e.g. 365 nm).

In some embodiments sufficient absorbance is provided by selection of a second free-radical photoinitiator that exhibits a maximum absorbance at a wavelength of the range 325-330 nm.

In some embodiments, sufficient absorbance is provided by selection of a second photoinitiator that comprises photoinitiator groups selected from benzil ketal or hydroxyacetophenone.

In some favored embodiments, the second photoinitiator has low absorbance at the first wavelength range. A 1 g/liter acetonitrile solution of the second photoinitiator, at a pathlength of 1 cm, typically has an absorbance of less than 0.1, 0.09, 0.08, 0.07, 0.06, 0.05, 0.04, 0.03, 0.02, or 0.01 at a wavelength of the first wavelength range when measured with a spectrophotometer.

In some embodiments, the first photoinitiator has an absorbance at 385 nm greater than the second photoinitiator by a factor of 5×-150× or greater.

In typical embodiments, the polymerizable composition comprises 0.1 to 5 wt. % of photoinitiators based on the total weight of the free-radically polymerizable resin.

In another embodiment, a photopolymerizable composition (suitable for use to make an orthodontic article) is described comprising a free-radically polymerizable resin; and a first free-radical photoinitiator and second free-radical initiator as described herein. The free-radically polymerizable resin typically comprises at least one monomer, oligomer and/or polymer comprising at least two (meth)acryl moieties. The photopolymerizable composition typically comprises at least one urethane component. In some embodiments, the urethane component is a urethane (meth) acrylate polymer comprising polymerized units derived from a diol selected from polycarbonate diol or polyester diol. The photopolymerizable composition typically comprises 25 to 70 wt. % of at least one monofunctional reactive diluent. In some embodiments, the monofunctional reactive diluent comprises a monofunctional reactive diluent where a homopolymer thereof has a Tg of 60, 65, 70, 75, 80, 85 or 90 degrees Celsius or greater. In some embodiments, the monofunctional reactive diluent comprises a monofunctional reactive diluent exhibiting a hydrophilic-lipophilic balance (HLB) value of less than 10. In some embodiments, the monofunctional reactive diluent comprises a monofunctional reactive diluent having a log P value of greater than 1.5, 2, 2.5, or 3.

Figure 1:
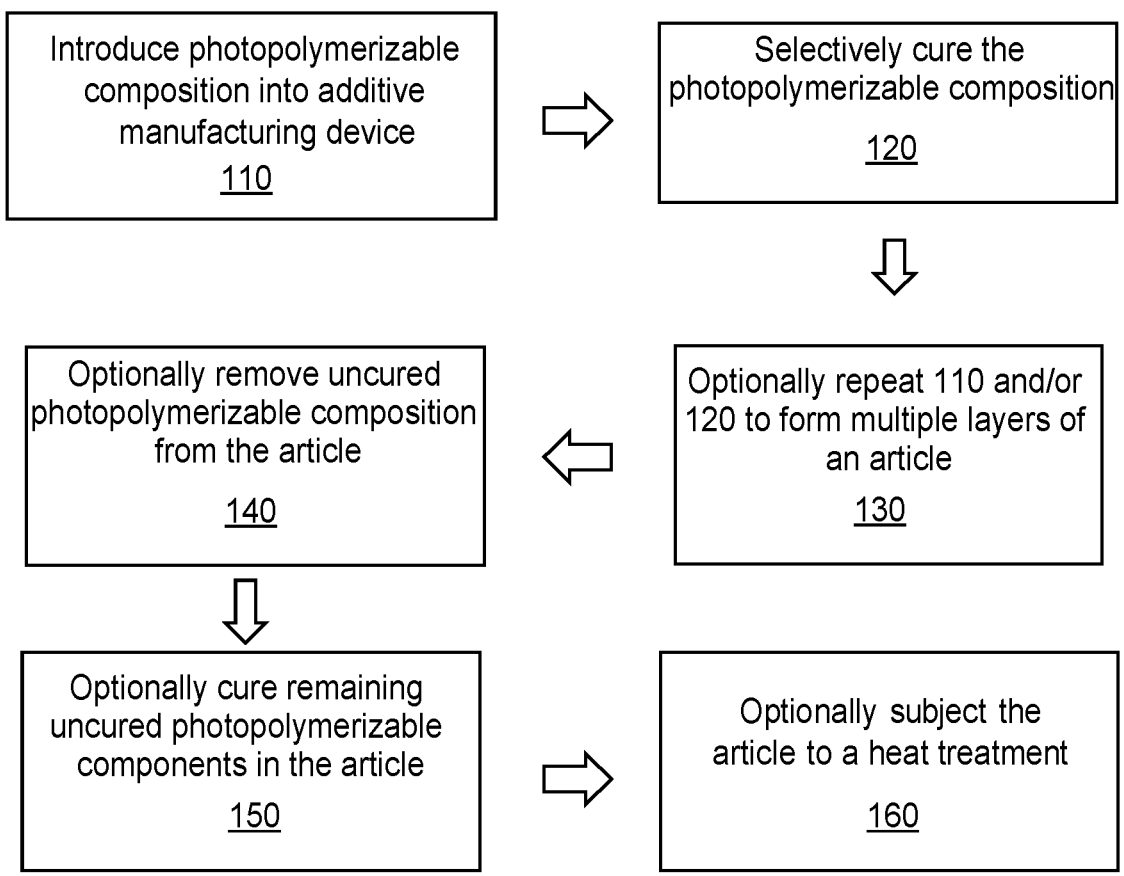
FIG. 1 is a flowchart of a process for building an article using the photopolymerizable compositions disclosed herein.

While the above-identified figures set forth several embodiments of the disclosure other embodiments are also contemplated, as noted in the description. The figures are not necessarily drawn to scale. In all cases, this disclosure presents the invention by way of representation and not limitation. It should be understood that numerous other modifications and embodiments can be devised by those skilled in the art, which fall within the scope and spirit of the principles of the invention.

DETAILED DESCRIPTION OF ILLUSTRATIVE EMBODIMENTS

As used herein, the term "hardenable" refers to a material that can be cured or solidified, e.g., by heating to remove solvent, heating to cause polymerization, chemical crosslinking, radiation-induced polymerization or crosslinking, or the like.

As used herein, "curing" means the hardening or partial hardening of a composition by any mechanism, e.g., by heat, light, radiation, e-beam, microwave, chemical reaction, or combinations thereof.

As used herein, "cured" refers to a material or composition that has been hardened or partially hardened (e.g., polymerized or crosslinked) by curing.

As used herein, "integral" refers to being made at the same time or being incapable of being separated without damaging one or more of the (integral) parts.

As used herein, the term "(meth)acrylate" is a shorthand reference to acrylate, methacrylate, or combinations thereof, and "(meth)acrylic" is a shorthand reference to acrylic, methacrylic, or combinations thereof. As used herein, the term "(meth)acryl" is a shorthand reference to acryl, methacryl, and combinations thereof. As used herein, "(meth) acrylate-functional compounds" are compounds that include, among other things, a (meth)acrylate moiety.

As used herein, "polymerizable composition" means a hardenable composition that can undergo polymerization upon initiation (e.g., free-radical polymerization initiation). Typically, prior to polymerization (e.g., hardening), the polymerizable composition has a viscosity profile consistent with the requirements and parameters of one or more 3D printing systems. In some embodiments, for instance, hardening comprises irradiating with actinic radiation having sufficient energy to initiate a polymerization or cross-linking reaction. For instance, in some embodiments, ultraviolet (UV) radiation, e-beam radiation, or both, can be used. Thermal initiation, using heat and a thermal initiator, can also be employed to initiate polymerization of a polymerizable composition. A combination of actinic radiation and thermal radiation can be used.

As used herein, a "resin" contains all polymerizable components (monomers, oligomers and/or polymers) being present in a hardenable composition. The resin may contain only one polymerizable component compound or a mixture of different polymerizable compounds.

As used herein, a "compatibilizer" refers to a component (e.g., in a polymerizable composition) that improves the interfacial adhesion between two otherwise immiscible (i.e. incompatible) material phases. The compatibilizer is present throughout at least one phase, it is preferentially present at an interface between at least two of the phases, and it increases the compatibility of at least two of the phases in the system. If the weight ratio of the compatibilizer in the system is too high relative to the other phases, a portion of it may separately form a distinct phase.

As used herein, "miscible" refers to any (e.g., polymeric) blend having a free energy of mixing less than zero, and "immiscible" refers to any blend having a free energy greater than zero. A miscible polymer is capable of forming a blend with a second material, which blend appears to be a single phase with no apparent phase separation, and such capability may depend on the temperature of the blend. In other words, a miscible blend is compatible; whereas an immiscible blend is not compatible. Unless specified otherwise, the photopolymerizable compositions described herein are compatible such that there is no apparent phase separation.

As used herein, the terms "glass transition temperature" and "Tg" are used interchangeably and refer to the glass transition temperature of a material or a mixture. Unless otherwise indicated, glass transition temperature values are determined by Differential Scanning calorimetry (DSC), such as at a heating rate of 10° C. per minute in a nitrogen stream. When the $T_g$ of a monomer is mentioned, it is the $T_g$ of a homopolymer of that monomer. The homopolymer must be sufficiently high molecular weight such that the $T_g$ reaches a limiting value, as it is generally appreciated that a $T_g$ of a homopolymer will increase with increasing molecular weight to a limiting value. The homopolymer is also understood to be substantially free of moisture, residual monomer, solvents, and other contaminants that may affect the $T_g$. A suitable DSC method and mode of analysis is as described in Matsumoto, A. et. al., J. Polym. Sci. A., Polym. Chem. 1993, 31, 2531-2539.

As used herein the term "hydrophilic-lipophilic balance" and "HLB" are used interchangeably and refer to a characterization of amphiphilic character of a compound.

As used herein, "thermoplastic" refers to a polymer that flows when heated sufficiently above its glass transition point and become solid when cooled.

As used herein, "thermoset" refers to a polymer that permanently sets upon curing and does not flow upon subsequent heating. Thermoset polymers are typically cross-linked polymers.

As used herein, "occlusal" means in a direction toward the outer tips of the patient's teeth; "facial" means in a direction toward the patient's lips or cheeks; and "lingual" means in a direction toward the patient's tongue.

The words "preferred" and "preferably" refer to embodiments of the disclosure that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the disclosure.

In this application, terms such as "a", "an", and "the" are not intended to refer to only a singular entity, but include the general class of which a specific example may be used for illustration. The terms "a", "an", and "the" are used interchangeably with the term "at least one." The phrases "at least one of" and "comprises at least one of" followed by a list refers to any one of the items in the list and any combination of two or more items in the list.

As used herein, the term "or" is generally employed in its usual sense including "and/or" unless the content clearly dictates otherwise.

The term "and/or" means one or all of the listed elements or a combination of any two or more of the listed elements.

Also herein, all numbers are assumed to be modified by the term "about" and preferably by the term "exactly." As used herein in connection with a measured quantity, the term "about" refers to that variation in the measured quantity as would be expected by the skilled artisan making the measurement and exercising a level of care commensurate with the objective of the measurement and the precision of the measuring equipment used. Also herein, the recitations of numerical ranges by endpoints include all numbers subsumed within that range as well as the endpoints (e.g., 1 to 5 includes 1, 1.5, 2, 2.75, 3, 3.80, 4, 5, etc.).

As used herein as a modifier to a property or attribute, the term "generally", unless otherwise specifically defined, means that the property or attribute would be readily recognizable by a person of ordinary skill but without requiring absolute precision or a perfect match (e.g., within +/−20% for quantifiable properties). The term "substantially", unless otherwise specifically defined, means to a high degree of approximation (e.g., within +/−10% for quantifiable properties) but again without requiring absolute precision or a perfect match. Terms such as same, equal, uniform, constant, strictly, and the like, are understood to be within the usual tolerances or measuring error applicable to the particular circumstance rather than requiring absolute precision or a perfect match.

Presently described is a free-radically polymerizable resin suitable for an orthodontic article comprising a first free-radical photoinitiator and a second free radical photoinitiator or thermal initiator. The free-radically polymerizable resin comprises at least one monomer, oligomer and/or polymer comprising at least two (meth)acrylate moieties. In typical embodiments, the free-radically polymerizable resin comprises at least one urethane component.

In one embodiment, the photopolymerizable composition comprises a blend of:
30 to 70 wt. %, inclusive, of at least one monomer, oligomer and/or polymer comprising at least two (meth)acryl moieties;
25 to 70 wt. %, inclusive, of monofunctional reactive diluent, wherein at least one monofunctional reactive diluent has a Tg of at least 60, 65, 70, 75, 80, 85 or 90 degrees Celsius; and at least one free-radical photoinitiator and at least one second free-radical initiator, as described herein.

In one embodiment, the photopolymerizable composition comprises a blend of:
30 to 70 wt. %, inclusive, of at least one urethane component;
25 to 70 wt. %, inclusive, of at least one monofunctional reactive diluent, wherein the at least one monofunctional reactive diluent comprises at least one monofunctional reactive diluent having a $T_g$ of up to but not including 25 degrees Celsius;
optionally at least one multifunctional reactive diluent in an amount of 1 to 30 wt. %, inclusive, if present, based on the total weight of the photopolymerizable composition;
at least one free-radical photoinitiator and at least one second free-radical initiator; and
an optional inhibitor in an amount of 0.001 to 1 wt. %, inclusive, if present, based on the total weight of the photopolymerizable composition.

Urethane Component

The photopolymerizable compositions of the present disclosure include at least one urethane component. As used herein, a "urethane component" refers to a compound including one or more carbamate functionalities in the backbone of the compound. In certain embodiments, the carbamate functionality is of the following formula:

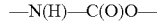

—N(H)—C(O)O—

Urethanes are prepared by the reaction of an isocyanate with an alcohol to form carbamate linkages. Moreover, the term "polyurethane" has been used more generically to refer to the reaction products of polyisocyanates with any polyactive hydrogen compound including polyfunctional alcohols, amines, and mercaptans.

The at least one urethane component provides both toughness (e.g., at least a minimum tensile strength and/or modulus) and flexibility (e.g., at least a minimum elongation at break) to the final article. In some embodiments, in addition to the urethane functionality, the urethane component further comprises one or more functional groups selected from hydroxyl groups, carboxyl groups, amino groups, and siloxane groups. These functional groups can be reactive with other components of the photopolymerizable composition during polymerization. The at least one urethane component often comprises a urethane (meth)acrylate, a urethane acrylamide, or combinations thereof, and wherein the at least one urethane component comprises a linking group selected from alkyl, polyalkylene, polyalkylene oxide, aryl, polycarbonate, polyester, polyamide, and combinations thereof. As used herein, "linking group" refers to a functional group that connects two or more urethane groups. The linking group may be divalent, trivalent, or tetravalent. In select embodiments, the at least one urethane component comprises a urethane (meth)acrylate comprising a polyalkylene oxide linking group, a polyamide linking group, or combinations thereof.

For example, the polymerizable component can include polyfunctional urethane acrylates or urethane methacrylates. These urethane (meth)acrylates are known to the person skilled in the art and can be prepared in a known manner by, for example, reacting a hydroxyl-terminated polyurethane with acrylic acid, methacrylic acid, or isocyanatoethyl methacrylate, or by reacting an isocyanate-terminated prepolymer with hydroxyalkyl (meth)acrylates to give the urethane (meth)acrylate. Suitable processes are disclosed, inter alia, in U.S. Pat. No. 8,329,776 (Hecht et al.) and U.S. Pat. No. 9,295,617 (Cub et al.). Suitable urethane methacrylates can include aliphatic urethane methacrylates, aliphatic polyester urethane methacrylates, and aliphatic polyester triurethane acrylates.

In some embodiments, the urethane component comprises a number average molecular weight (Mn) of 200 grams per mole to 5,000 grams per mole. The number average molecular weight may be measured with gel permeation chromatography. The "urethane component" as used herein optionally includes each of a "high Mn urethane component" and a "low Mn urethane component". The high Mn urethane component encompasses compounds including one or more urethane functionalities in the backbone of the compound and that have a number average molecular weight of 1,000 grams per mole (g/mol) or greater, with the proviso that all branches off the backbone of the compound, if present, have a Mn of no more than 200 g/mol. Stated another way, the high Mn urethane component typically has a Mn of 1,000 g/mol or greater, 1,100 g/mol or greater, 1,200 g/mol or greater, 1,300 g/mol or greater, 1,400 g/mol or greater, 1,500 g/mol or greater, 1,600 g/mol or greater, 1,700 g/mol or greater, 1,800 g/mol or greater, 2,000 g/mol or greater, 2,250 g/mol or greater, 2,500 g/mol or greater, 2,750 g/mol or greater, 3,000 g/mol or greater, 3,250 g/mol or greater, 3,500 g/mol or greater, 3,7500 g/mol or greater, or even 4,000 g/mol or greater; and 5,000 g/mol or less, 4,800 g/mol or less, 4,600 g/mol or less, 4,400 g/mol or less, 4,100 g/mol or less, 3,900 g/mol or less, 3,700 g/mol or less, 3,400 g/mol or less, 3,100 g/mol or less, 2,900 g/mol or less, 2,700 g/mol or less, 2,400 g/mol or less, or 2,200 g/mol or less, or even 1,900 g/mol or less.

The low Mn urethane component encompasses compounds including one or more urethane functionalities in the backbone of the compound and that have either 1) a number average molecular weight of 100 g/mol or greater and up to but not including 1,000 g/mol, or 2) a number average molecular weight of 100 g/mol or greater and 2,000 g/mol or less, with the proviso that a number average molecular weight of any one or more linear portions between two reactive groups and/or branches is up to but not including 1,000 g/mol. For instance, a branched urethane component can have a total Mn of greater than 1,000 g/mol but still be a low Mn urethane component due to having a linear segment between two branching points with a Mn of less than 1,000 g/mol. Stated another way, the 1) category of low Mn urethane components typically have a Mn of 100 g/mol or greater, 150 g/mol or greater, 200 g/mol or greater, 250 g/mol or greater, 300 g/mol or greater, 350 g/mol or greater, 400 g/mol or greater, 450 g/mol or greater, 500 g/mol or greater, 550 g/mol or greater, 600 g/mol or greater, 650 g/mol or greater, 700 g/mol or greater, 750 g/mol or greater, or 800 g/mol or greater; and up to but not including 1,000 g/mol, 975 g/mol or less, 925 g/mol or less, 875 g/mol or less, 825 g/mol or less, 775 g/mol or less, 725 g/mol or less, 675 g/mol or less, 625 g/mol or less, 575 g/mol or less, 525 g/mol or less, 475 g/mol or less, or 425 g/mol or less, or even 375 g/mol or less. The 2) category of low Mn urethane components typically have a Mn of 200 g/mol or greater, 250 g/mol or greater, 300 g/mol or greater, 350 g/mol or greater, 400 g/mol or greater, 450 g/mol or greater, 500 g/mol or greater, 550 g/mol or greater, 600 g/mol or greater, 650 g/mol or greater, 700 g/mol or greater, 750 g/mol or greater, or 800 g/mol or greater; and 1,500 g/mol or less, 1,400 g/mol or less, 1,300 g/mol or less, 1,200 g/mol or less, 1,100 g/mol or less, 1,000 g/mol or less, 975 g/mol or less, 925 g/mol or less, 875 g/mol or less, 825 g/mol or less, 775 g/mol or less, 725 g/mol or less, 675 g/mol or less, 625 g/mol or less, 575 g/mol or less, 525 g/mol or less, 475 g/mol or less, or 425 g/mol or less, or even 375 g/mol or less. Each of the foregoing second category of low Mn urethane components includes the proviso that a number average molecular weight of any one or more linear portions between two reactive groups and/or branches is up to but not including 1,000 g/mol, 950 g/mol or less, 900 g/mol or less, 850 g/mol or less, 800 g/mol or less, or 750 g/mol or less; and a number average molecular weight of any one or more linear portions between two reactive groups and/or branches is 100 g/mol or greater, 200 g/mol or greater, 250 g/mol or greater, 300 g/mol or greater, 350 g/mol or greater, 400 g/mol or greater, 450 g/mol or greater, or 500 g/mol or greater.

The use of high Mn urethane components having a number average molecular weight of 1,000 g/mol or greater tend to provide a final article having at least a certain desirable minimum elongation at break (e.g., at least 15, 20, 25% or greater). Eighty percent by weight or greater of the at least one urethane component is provided by one or more high Mn (e.g., long chain) urethane components. More particularly, in embodiment where a low molecular weight urethane component is present, typical ratios of the high number average molecular weight urethane component to the low number average molecular weight urethane component range from 95:5 high Mn urethane component to low Mn urethane component to 80:20 high Mn urethane component to low Mn urethane component. Stated another way, photopolymerizable compositions according to at least certain aspects of the disclosure include 80 wt. % or more of the total urethane component as a high Mn urethane component, 85 wt. % or more, 87 wt. % or more, 90 wt. % or more, 92 wt. % or more, 95 wt. % or more, or even 97 wt. % or more of the total urethane component as a high Mn urethane component; and 100% or less of the total urethane component as a high Mn urethane component, 98 wt. % or less, 96 wt. % or less, 94 wt. % or less, 91 wt. % or less, 89 wt. % or less, or 86 wt. % or less of the total urethane component as a high Mn urethane component. Similarly, photopolymerizable compositions according to at least certain aspects of the disclosure can include 2 wt. % or more of the total urethane component as a low Mn urethane component, 4 wt. % or more, 5 wt. % or more, 8 wt. % or more, 10 wt. % or more, 12 wt. % or more, 15 wt. % or more, or even 17 wt. % or more of the total urethane component as a low Mn urethane component; and 20 wt. % or less of the total urethane component as a low Mn urethane component, 18 wt. % or less, 16 wt. % or less, 14 wt. % or less, 11 wt. % or less, 9 wt. % or less, 7 wt. % or less, 6 wt. % or less, or 3 wt. % or less of the total urethane component as a low Mn urethane component.

According to certain embodiments, at least one urethane component comprises at least one (meth)acrylate component having a urethane moiety, which may help to improve physical properties of the cured composition like flexural strength and/or elongation at break. Such a urethane component can be characterized by the following features alone or in combination:

a) comprising at least 2 or 3 or 4 (meth)acrylate moieties;

b) number average molecular weight (Mn): from 1,000 to 5,000 g/mol or from 1,000 to 2000 g/mol;

c) comprising a C1 to C20 linear or branched alkyl moiety to which the (meth)acrylate moieties are attached through urethane moieties;

d) viscosity: from 0.1 to 100 Pa·s or 1 to 50 Pa·s at 23° C.

A combination of the features a) and b) or b) and c) or a) and d) can sometimes be preferred.

In other embodiments, the urethane component comprises a polyurethane (meth)acrylate polymer preferably having a weight average molecular weight (Mw) of 2,000 or greater, 2,500 or greater, of 3,000 g/mol or greater, 4,000 g/mol or greater, 5,000 g/mol or greater, 6,000 g/mol or greater, 6,000 g/mol or greater, 7,000 g/mol or greater, 8,000 g/mol or greater, 9,000 g/mol or greater, 10,000 g/mol or greater, 11,000 g/mol or greater, or 12,000 g/mol or greater; and 50,000 g/mol or less, 45,000 g/mol or less, 40,000 g/mol or less, 35,000 g/mol or less, 32,000 g/mol or less, 30,000 g/mol or less, 28,000 g/mol or less, 25,000 g/mol or less, 23,000 g/mol or less, 20,000 g/mol or less, or 18,000 g/mol or less. Higher molecular weight of the polyurethane methacrylates will result in higher viscosity resin formulations with comparable compositions and loadings, which makes them less flowable; lower molecular weight of the polyurethane methacrylates will reduce their toughening effect on the cured articles.

The polyurethane (meth)acrylate polymer may be prepared from a polypropylene oxide diol as described in U.S. Application Ser. No. 62/643,431, a polycarbonate diol as described in U.S. Application Ser. Nos. 62/736,01 and 62/736,027, or a polyester diol as described in co-filed case U.S. Application Ser. No. 62/769,081; incorporated herein by reference Urethane (meth)acrylates may be obtained by a number of processes known to the skilled person. The urethane(meth) acrylates are typically obtained by reacting an NCO-terminated compound with a suitable monofunctional (meth) acrylate monomer such as hydroxyethyl acrylate, hydroxyethyl methacrylate, hydroxypropylmethacrylate, preferably hydroxyethyl- and hydroxypropylmethacrylate. For example, a polyisocyanate and a polyol may be reacted to form an isocyanate-terminated urethane prepolymer that is subsequently reacted with a (meth)acrylate such as 2-hydroxy ethyl(meth)acrylate. These types of reactions may be conducted at room temperature or higher temperature, optionally in the presence of catalysts such as tin catalysts, tertiary amines and the like.

Polyisocyanates which can be employed to form isocyanate-functional urethane prepolymers can be any organic isocyanate having at least two free isocyanate groups. Included are aliphatic cycloaliphatic, aromatic and araliphatic isocyanates. Any of the known polyisocyanates such as alkyl and alkylene polyisocyanates, cycloalkyl and cycloalkylene polyisocyanates, and combinations such as alkylene and cycloalkylene polyisocyanates can be employed. Preferably, diisocyanates having the formula X(NCO)₂ can be used, with X representing an aliphatic hydrocarbon radical with 2 to 15 C atoms, a cycloaliphatic hydrocarbon radical with 5 to 18 C atoms, an aromatic hydrocarbon radical with 6 to 16 C atoms and/or an aliphatic hydrocarbon radical with 7 to 15 C atoms.

Examples of suitable polyisocyanates include 2,2,4-trimethylhexamethylene-1,6-diisocyanate, hexamethylene-1,6-diisocyanate (HDI), cyclohexyl-1,4-diisocyanate, 4,4'-methylene-bis(cyclohexyl isocyanate), 1,1'-methylenebis(4-isocyanato) cyclohexane, isophorone diisocyanate (IPDI), 4,4'-methylene diphenyl diisocyanate, 1,4-tetramethylene diisocyanate, meta- and para-tetra¬methylxylene diisocyanate, 1,4-phenylene diisocyanate, 2,6- and 2,4-toluene diisocyanate, 1,5-naphthylene diisocyanate, 2,4' and 4,4'-diphenylmethane diisocyanate; methylenedicyclohexylene-4,4'-diisocyanate (H12MDI), 3-isocyanatomethyl-3,5,5-trimethylcyclohexyl isocyanate, tetramethyl-m-xylylene diisocyanate, a mixture of 2,2,4- and 2,4,4-trimethyl-1,6-diisocyanatohexane (TMXDI), trans-1,4-hydrogenated xylylene diisocyanates (H6XDI), 4,4'-methylene diphenyl diisocyanate, 2,4'-methylene diphenyl diisocyanate, a mixture of 4,4'-methylene diphenyl diisocyanate and 2,4'-methylene diphenyl diisocyanate, 1,4-phenylene diisocyanate, pentamethylene diisocyanate, dodecamethylene diisocyanate, 1,3-cyclopentane diisocyanate, 1,3-cyclohexane diisocyanate, methyl 2,4-cyclohexane diisocyanate, methyl-2,6-cyclohexane diisocyanate, 1,4-bis (isocyanatomethyl) cyclohexane, 1,3-bis (isocyanatomethyl) cyclohexane, 4,4'-toluidine diisocyanate, 4,4'-diphenyl ether diisocyanate, 1,3- or 1,4-xylylene diisocyanate, lysine diisocyanate methyl ester, 3,3'-dimethyl-4,4'-diphenylmethane diisocyanate, 3,3'-dimethyl-phenylene diisocyanate, 2,5-bis (isocyanate methyl)-bicyclo[2.2.1]heptane, 2,6-bis (isocyanate methyl)-bicyclo[2.2.1]heptane, bis (2-isocyanate ethyl) fumarate, 4-diphenylpropane diisocyanate, trans-cyclohexane-1,4-diisocyanatehydrogenated dimer acid diisocyanate, a norbornene diisocyanate, methylenebis 6-isopropyl-1,3-phenyl diisocyanate; and mixtures thereof.

It is also possible to use higher-functional polyisocyanates known from polyurethane chemistry or else modified polyisocyanates, for example containing carbodiimide groups, allophanate groups, isocyanurate groups and/or biuret groups. Particularly preferred isocyanates are biurets and isocyanurates derived from isophorone diisocyanate.

The isocyanate terminated urethane compound (or reaction product of polypropylene oxide diol, polycarbonate diol, or polyester diol and a diisocyanate) is capped with a (meth)acrylate to produce a urethane(meth)acrylate compound. In general, any (meth)acrylate-type capping agent having a terminal hydroxyl group and also having an acrylic or methacrylic moiety can be employed, with the methacrylic moiety being preferred. Examples of suitable capping agents include 2-hydroxyethyl(meth)acrylate, 2-hydroxypropyl (meth)acrylate, glycerol di(meth)acrylate and/or trimethylolpropane di(meth)acrylate. Particularly preferred are 2-hydroxyethyl methacrylate (HEMA) and/or 2-hydroxyethyl acrylate (HEA).

The equivalence ratio of isocyanate groups to reactive with isocyanate groups (i.e. hydroxyl groups) is about 1:1. Typically, there is a slight excess of hydroxyl groups resulting in substantially all the isocyanate groups being consumed during the polymerization.

The isocyanate polyaddition reaction can take place in the presence of catalysts known from polyurethane chemistry, for example organotin compounds such as dibutyltin dilaurate or amine catalysts such as diazabicyclo[2.2.2]octane. Furthermore, the synthesis can take place both in the melt or in a suitable solvent which can be added before or during the prepolymer preparation. Suitable solvents are for example acetone, 2-butanone, tetrahydrofuran, dioxane, dimethylformamide, N-methyl-2-pyrrolidone (NMP), ethyl acetate, alkyl ethers of ethylene and propylene glycol and aromatic hydrocarbons. The use of ethyl acetate as solvent is particularly preferred.

According to select embodiments the urethane component comprises a urethane dimethacrylate of the following formulas:

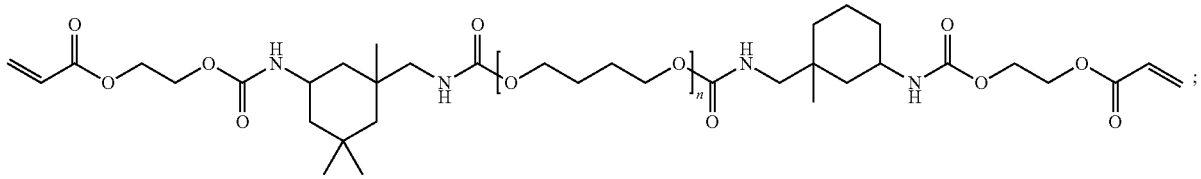

wherein n=9 or 10;

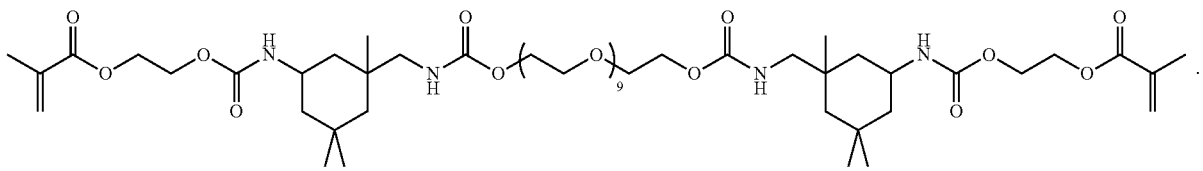

Examples of commercially available urethane components include those available under the trade designations of EXOTHANE 108, EXOTHANE 8, and EXOTHANE 10 from Esstech Inc, and DESMA from 3M Company. DESMA is described in, e.g., paragraph [0135] and Table 3 of EP2167013B1 (Hecht et al.).

The urethane component is included in the photopolymerizable composition in an amount of 50 to 90 wt. %, inclusive, based on the total weight of the photopolymerizable composition, such as 50 to 70 wt. %, inclusive. Typically, the urethane component is included in the photopolymerizable composition in an amount of 50 wt. % or more, 52 wt. % or more, 55 wt. % or more, 57 wt. % or more, 60 wt. % or more, 61 wt. % or more, 62 wt. % or more, 63 wt. % or more, 64 wt. % or more, 65 wt. % or more, 70 wt. % or more, or 72 wt. % or more; and 90 wt. % or less, 87 wt. % or less, 85 wt. % or less, 80 wt. % or less, 77 wt. % or less, or 75 wt. % or less, based on the total weight of the photopolymerizable composition.

Polycarbonate and Polyester Urethane (Meth)Acrylate Polymers

In other embodiments, the urethane component is a urethane (meth)acrylate polymer. Such polymer is the reaction product of a (e.g. aliphatic) polycarbonate or polyester diol; an (e.g. aliphatic and/or aromatic) diisocyanate, and an (e.g. aliphatic and/or aromatic) hydroxy functional (meth)acrylate.

In one embodied synthetic route, the urethane (meth)acrylate polymer is a reaction product of an (e.g. aliphatic) polycarbonate or polyester diol; an (e.g. aliphatic and/or aromatic) diisocyanate, and an (e.g. aliphatic and/or aromatic) hydroxy functional (meth)acrylate.

The polycarbonate diol is typically of the following formula:

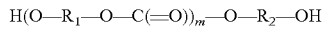

wherein each of $R_1$ in each (O—$R_1$—O—C(=O)) repeat unit, and $R_2$ are independently an aliphatic, cycloaliphatic, or aliphatic/cycloaliphatic alkylene group and an average number of carbon atoms in a combination of all the $R_1$ and $R_2$ groups is 4 to 10, and m is (an integer of) 2 to 23. Stated another way, while some repeat units of $R_1$ and/or $R_2$ may have a carbon number of less than 4 (e.g., 2 or 3), enough of the repeat units have a sufficiently high carbon number that when the carbon numbers of all the repeat units of $R_1$ and $R_2$ of the polycarbonate diol formula are averaged, that average falls within the range of 4 to 10, or any of 4 to 6, 4 to 7, 4 to 8, 4 to 9, 5 to 7, 5 to 8, 5 to 9, 5 to 10, 6 to 8, 6 to 9, 6 to 10, 7 to 9, 7 to 10, or 8 to 10. In select embodiments, at least one of $R_1$ or $R_2$ is —$CH_2CH_2CH(CH_3)CH_2CH_2$—, —$(CH_2)_6$—, or —$(CH_2)_4$—, and preferably a combination of —$CH_2CH_2CH(CH_3)CH_2CH_2$—, and —$(CH_2)_6$—.

In some embodiments, either the polycarbonate diol has a number average molecular weight (Mn) of greater than 1,000 grams per mole (g/mol) or a weighted average of all polycarbonate diols present in the components has a Mn of greater than 1,000 g/mol, wherein Mn is determined by OH value. Stated a different way, when the components contain a single polycarbonate diol, the polycarbonate diol has a Mn higher than 1,000 g/mol. When the components contain two or more polycarbonate diols, the Mn of at least one of the polycarbonate diols may be 1,000 g/mol or less with the proviso that a weighted average of all the Mn values of the two or more polycarbonate diols is higher than 1,000 g/mol. For instance, components containing two polycarbonate diols could include a 1:2 molar ratio of a first polycarbonate diol having a Mn of about 500 g/mol to a second polycarbonate diol having a Mn of about 1,500 g/mol, resulting in a weighted average Mn of 1,167 g/mol. In certain embodiments, a polycarbonate diol (or a weighted average of all the polycarbonate diols present in the components) has a number average molecular weight of 1,500 g/mol or higher.

In some embodiments, the polyester diol is typically of the following formula:

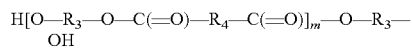

wherein $R_3$ and $R_4$ are independently straight or branched chain or cycle-containing alkylene, groups, that optionally include heteroatoms, such as oxygen. $R_3$ and $R_4$ independently comprise 2 to 40 carbon atoms. The subscript "m" is typically at least 2, 3, 4, 5, 6, or 7. The subscript "m" is typically no greater than 50, 45, 40, 35, 30, 25, 20, or 15. In some embodiments, the $R_3$ and $R_4$ are alkylene.

Representative polyester diols include for example neopentyl glycol adipate diol, butane diol adipate diol; 3-methyl-1,5-pentanediol adipate diol; and 3-methyl-1,5-pentanediol sebecate diol, and dimer acid based polyols in which the dimer acid is derived for example from dimerization of two 18 carbon diacids such as linoleic acid.

In some embodiments, such as the diols just described, the polyester diol comprises a single $R_3$ group (e.g. neopentyl or 3-methyl-1,5-pentyl) and a single $R_4$ group (e.g. adipate).

In other embodiments, the aliphatic polyester diol can be prepared from more than one diol and more than one acid. In this embodiment, the diol can contain two or more different $R_3$ groups and two or more different $R_4$ groups such as in the case of ethylene glycol-hexane diol/adipate-azelate copolyester diol.

In other embodiments, the polyester diol is typically of the formula as follows:

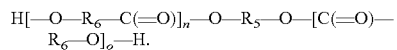

wherein $R_5$ and $R_6$ are independently straight or branched chain or cycle-containing alkylene groups that optionally include heteroatoms such as oxygen, the alkylene groups independently comprise 2 to 40 carbon atoms. The subscripts "n" and "o" (i.e. the letter o) are typically independently at least 4, 5 or 6. The subscripts "n" and "o" are typically independently no greater than 25, 20, or 15.

One representative polyester diol of this type is polycaprolactone diol, such as available from Perstorp. In this embodiment, $R_6$ is a $C_5$ alkylene group and $R_5$ is the residue of an alcohol, such as ethylene glycol, butylene glycol, diethylene glycol, and the like.

In some embodiments, at least one of $R_3$ or $R_4$ of the polyester diol formula and at least one of $R_5$ and $R_6$ the polyester diol formula is a straight or branched chain or cycle-containing alkylene group independently comprising at least 4, 5, or 6 carbon atoms.

In some embodiments, each of the $R_3$ and $R_4$ groups of the polyester diol formula are alkylene groups independently comprising at least 4, 5, or 6 carbon atoms. In some embodiments, each of the $R_5$ and $R_6$ groups of the polyester diol formula are alkylene groups independently comprising at least 4, 5, or 6 carbon atoms.

The values of m, n, and o are chosen such that the molecular weight (Mn) of the diol is at least 500, 600, 700, 800, 900, or 1000 g/mole. In some embodiments, the molecular weight (Mn) of the diol is at least 1100, 1200, 1300, 1400, 1500 g/mole. In some embodiments, the molecular weight (Mn) of the diol is at least 1600, 1700, 1800, 1900, or 2000 g/mole. In some embodiments, the molecular weight (Mn) of the diol is no greater than 10,000; 9,000; 8,000; 7,000; 6,000; 5000; 4000; or 3000 g/mole. When the molecular weight is too low the elongation can be insufficient (i.e. less than 15-20%). The values of m, n, and o can vary widely due to the range of carbons for the $R_3$, $R_4$, $R_5$ and $R_6$ groups.

Various hydroxy functional (meth)acrylates can be used in the preparation of the (e.g. polycarbonate or polyester) urethane (meth)acrylate polymer. In typical embodiments, the hydroxy functional (meth)acrylate has the formula as follows:

wherein Q is a polyvalent (e.g. divalent or trivalent) organic linking group, A has the formula —OC(=O)C($R_1$)=CH$_2$ wherein $R_1$ is H or alkyl of 1 to 4 carbon atoms (e.g. methyl), and p is 1 or 2. In some embodiments, A is a methacrylate functional group ($R_1$=methyl).

Suitable examples of hydroxy functional (meth)acrylates include for example, 2-hydroxyethyl methacrylate, hydroxypropyl methacrylate (all isomers), hydroxybutyl methacrylate (all isomers), poly(e-caprolactone) mono[2-methacryloxy ethyl] esters, glycerol dimethacrylate, 1-(acryloxy)-3-(methacryloxy)-2-propanol, 2-hydroxy-3-phenyloxypropyl methacrylate, 2-hydroxyalkyl methacryloyl phosphate, 4-hydroxycyclohexyl methacrylate, trimethylolpropane dimethacrylate, trimethylolethane dimethacrylate, 1,4-butanediol monomethacrylate, neopentyl glycol monomethacrylate, 1,6-hexanediol monomethacrylate, 3-chloro-2-hydroxypropyl methacrylate, 2-hydroxy-3-alkyloxymethacrylate, polyethylene glycol monomethacrylate, polypropylene glycol monomethacrylate, —OH terminated ethylene oxide-modified phthalic acid methacrylate, and 4-hydroxycyclohexyl methacrylate.

In some embodiments, Q is a straight or branched chain or cycle-containing aliphatic (e.g. divalent) connecting group, such an alkylene. In other embodiments, Q is an aromatic (e.g. divalent) connecting group, such as arylene, aralkylene, and alkarylene. Q can optionally include heteroatoms such as O, N, and S, and combinations thereof. Q can also optionally include a heteroatom-containing functional group such as carbonyl or sulfonyl, and combinations thereof. Q typically comprises no greater than 20 carbon atoms.

In some embodiments, Q is typically alkylene comprising no greater than 12, 10, 8 or 6 carbon atoms. In some embodiments, Q is a $C_2$, $C_3$, or $C_4$ alkylene group. In some embodiments, p is 1.

Such urethane (meth)acrylate polymer can be represented by the following formula:

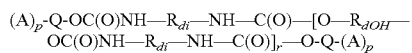

wherein, A has the formula —OC(=O)C($R_1$)=CH$_2$ wherein $R_1$ is H or alkyl of 1 to 4 carbon atoms (e.g. methyl), p is 1 or 2, Q is a polyvalent organic linking group as described above, $R_{di}$ is the residue of a diisocyanate (i.e. the moiety between the isocyanate group), $R_{dOH}$ is the residue of a polyester or polycarbonate polyol (i.e. the moiety between the OH groups of the diol), and r average 1 to 15. In some embodiments, r averages at least 2, 3, 4, or 5. In some embodiments, A is a methacryl functional group, such as methacrylate.

Oligomers that are the reaction product of hydroxy functional (meth)acrylate and diisocyanate (at the exclusion of polycarbonate or polyester diol) have been found to be a by-product of the polymerization reaction of components in certain embodiments. It is possible to purify the polyurethane methacrylate polymer to remove such by-products. Alternatively, additional by-products such as oligomers may be added to the polymerized reaction product, particularly when a specific reaction generates a small amount of one or more by-products. It has been discovered that some side product components can improve at least one of modulus or extent of crosslinking after the photopolymerizable composition has been cured.

For example, photopolymerizable compositions optionally comprise a compound of the formula:

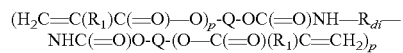

wherein Q, p, and $R_1$ are the same as described above for the hydroxy functional (meth)acrylate, and $R_{di}$ is the residue of a diisocyanate as defined above. Typically, the compound is produced during the polymerization of the components, as described above. In certain embodiments, the compound is added to the photopolymerizable composition, particularly when a smaller amount of such compound is produced by the polymerization of components than desired. In any embodiment, the compound may advantageously improve crosslinking during the photopolymerization reaction, increase the modulus or the photopolymerization reaction product, or both. Regardless of whether the compound is formed during the polymerization of the components, added separately to the photopolymerizable composition, or both, in some embodiments the compound is present in an amount of 0.05 weight percent (wt. %) or greater, based on the weight of the polymerizable composition, 0.1 wt. % or greater, 0.5 wt. % or greater, 1 wt. % or greater, 1.5 wt. % or greater, 2 wt. % or greater, 3 wt. % or greater, 4 wt. % or greater, 5 wt. % or greater, 6 wt. % or greater, 7 wt. % or greater, 8 wt. % or greater, or 9 wt. % or greater; and 20 wt. % or less, 18 wt. % or less, 16 wt. % or less, 14 wt. % or less, 12 wt. % or less, or 10 wt. % or less, based on the weight of the polymerizable composition. Stated another way, the compound of may be present in the photopolymerizable composition in an amount of 0.05 to 20 weight percent (wt. %), 1.5 to 12 wt. %, 2.5% to 12% wt. %, 5% to 15% wt. %, 5% to 12% wt. %, 7% to 15% wt. %, 7% to 12% wt. %, or 5 to 20 wt. %, based on the weight of the polymerizable resin composition.

In select embodiments, the compound is:

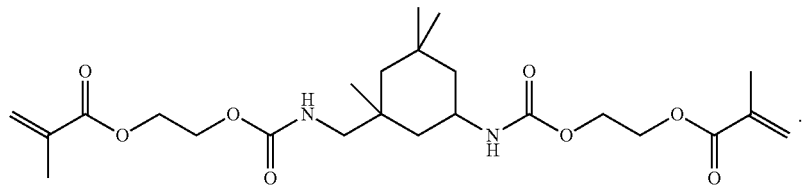 [SMILES: C=C(C)C(=O)OCCOC(=O)NCC1(C)CC(NC(=O)OCCOC(=O)C(=C)C)CC(C)(C)C1]

In another embodied synthetic route, the urethane (meth) acrylate polymer is a reaction product of an (e.g. aliphatic) polycarbonate or polyester diol, as described above, and an (e.g. aliphatic and/or aromatic) isocyanate functional (meth) acrylate, typically in the presence of a catalyst.

In typical embodiments, the isocyanate functional (meth) acrylate has the formula as follows:

$$(A)_p\text{-}Q\text{-NCO}$$

wherein A, Q, and p are the same as described above with respect to the hydroxyl functional (meth)acrylate.

Examples of the isocyanate functional (meth)acrylates include isocyanatoethyl methacrylate, isocyanatoethoxyethyl methacrylate, isocyanatoethyl acrylate, and 1,1-(bisacryloyloxymethyl) ethyl isocyanate, which are for instance commercially available from Showa Denko (Tokyo, Japan).

Such urethane (meth)acrylate polymers can be represented by the following formula:

$$(A)_p\text{-}Q\text{-NHC(O)O}\text{—}R_{dOH}\text{—OC(O)NH-Q-}(A)_p$$

wherein A, p, Q and $R_{dOH}$ are the same as described above. In some embodiments, A is a methacrylate functional group.

The urethane (meth)acrylate polymer (e.g. comprising polymerized units of an aliphatic polycarbonate or polyester diol) described herein is the primary difunctional (e.g. di(meth)acrylate) component of the free-radically polymerizable resin composition. The total amount of urethane (meth)acrylate polymer is typically at least 30, 35, or 40 wt. % based on the total weight of the free-radically polymerizable resin (e.g. excluding inorganic components, such as filler.) The total amount of urethane (meth)acrylate polymer is typically no greater than 70, 65, or 60 wt. %.

In some embodiments, the weight ratio of the monofunctional (meth)acrylate monomer(s) to urethane (meth)acrylate polymer (e.g. comprising polymerized units of an aliphatic polycarbonate or polyester diol) can range from 2:1 to 1:2 or 1.5:1 to 1:1.5.

The polymerizable compositions may optionally include other difunctional (meth)acrylate monomer(s) or polymer(s). The other difunctional (meth)acrylate monomer(s) or polymer(s) may include the previously described by-product as well as reaction products of diisocyanates and hydroxy functional (meth)acrylates as previously described that were not utilized in the preparation of the polycarbonate or polyester urethane (meth)acrylate polymer.

In some embodiments, the total amount of other difunctional (e.g. di(meth)acrylate) components (including by-product) can be at least 0.5, 1, 2, 3, 4, or 5 wt. % based on the total weight of the polymerizable organic components of the composition. In some embodiments, the total amount of other difunctional (e.g. di(meth)acrylate) components (including by-product) is no greater than 20, 19, 18, 17, 16, or 15 wt. %. In some embodiments, the total amount of other difunctional (e.g. di(meth)acrylate) components including by-product) is no greater than 14, 13, 12, 11, or 10 wt. %.

Reactive Diluent

The photopolymerizable compositions of the present disclosure include at least one monofunctional reactive diluent. A "reactive diluent," for reference purposes herein, is a component that contains at least one free radically reactive group (e.g., an ethylenically-unsaturated group) that can co-react with the at least one urethane component (e.g., is capable of undergoing addition polymerization). The reactive diluent has a smaller molecular weight than at least one (e.g., high Mn) urethane component, often less than 400 grams per mole, and does not contain any urethane functional groups (e.g., is free of any urethane functional groups).

In some embodiments, the reactive diluent comprises at least one monofunctional reactive diluent having a $T_g$ of up to but not including 25° C., 20° C., 15° C., or 10° C. The $T_g$ may be 24° C., 23° C., 22° C., 21° C., 20° C., 18° C., 16° C., 14° C., 12° C., 10° C., or 8° C. The inclusion of a low $T_g$ monofunctional reactive diluent tends to lower the $T_g$ of a reaction product of the photopolymerizable composition.

In some embodiments, the at least one monofunctional reactive diluent further comprises a second monofunctional reactive diluent, wherein the second monofunctional reactive diluent has a $T_g$ of 25° C. or greater, 30° C. or greater, 35° C. or greater, or 40° C. or greater. The $T_g$ may be 80° C. or less, 75° C. or less, 70° C. or less, 65° C. or less, 60° C. or less, 55° C. or less, 50° C. or less, or 45° C. or less.

It has been unexpectedly found that a balance of physical properties (e.g., strength and elongation at break) can be obtained in a polymerized article when including both a monofunctional reactive diluent having a $T_g$ of less than 25° C. and a monofunctional reactive diluent having a $T_g$ of 25° C. or greater, in certain photopolymerizable compositions according to the present disclosure. Thus, in some embodiments, the photopolymerizable composition comprises a combination of such low and high Tg monofunctional reactive diluents.

In some embodiments, the monofunctional reactive diluent further comprises a third monofunctional reactive diluent, plus optionally a fourth monofunctional reactive diluent. In an embodiment, the at least one monofunctional reactive diluent comprises one monofunctional reactive diluent having a $T_g$ of up to but not including 25 degrees Celsius and two monofunctional reactive diluents having a $T_g$ of 25 degrees Celsius or greater. In an alternative embodiment, the at least one monofunctional reactive diluent comprises two monofunctional reactive diluents having a $T_g$ of up to but not including 25 degrees Celsius and one monofunctional reactive diluent having a $T_g$ of 25 degrees Celsius or greater.

In select embodiments, the (at least one) monofunctional reactive diluent comprises a (meth)acrylate, an alkyl (meth) acrylate, a phenoxy (meth)acrylate, a hydroxy alkyl (meth) acrylate, or a combination thereof. In some preferred embodiments, the monofunctional reactive diluent comprises phenoxy ethyl methacrylate, such as in an amount of 20 to 80 wt. % of the total amount of the total monofunctional reactive diluent content.

In certain embodiments, the monofunctional reactive diluent comprises an (e.g., amphiphilic) monofunctional reactive diluent. exhibiting a hydrophilic-lipophilic balance (HLB) value of less than 10. Amphiphilic compounds can be characterized by various methodology. One common characterization method, as known in the art, is the hydrophilic-lipophilic balance ("HLB"). Although various methods have been described for determining the HLB of a compound, as used herein, HLB refers to the value obtained by the Griffin's method (See Griffin W C: "Calculation of HLB Values of Non-Ionic Surfactants," Journal of the Society of Cosmetic Chemists 5 (1954): 259). The computations of were conducted utilizing the software program Molecular Modeling Pro Plus from Norgwyn Montgomery Software, Inc. (North Wales, Pa.).

The HLB of some monofunctional reactive diluents and di(meth)acrylate components is described in the following table.

| Hydrophilic-Lipophilic Balance (HLB) Values | |
|---|---|
| Compound | HLB |
| 2-Ethyl Hexyl Methacrylate | 3.4 |
| Hydroxyethyl Methacrylate | 12.4 |
| Isobutyl methacrylate | 4.2 |
| Isobornyl methacrylate | 1.9 |
| Phenoxyethyl methacrylate | 5.6 |
| Exothane 10 | 13.8 |
| H1188 | 5.3 |
| U847 | 4.9 |

According to Griffin's method: HLB=20*Mh/M where Mh is the molecular mass of the hydrophilic portion of the molecule, and M is the molecular mass of the whole molecule. This computation provides a numerical result on a scale of 0 to 20, wherein "0" is highly lipophilic. Preferably, an amphiphilic monofunctional reactive diluent useful for at least certain embodiments of the photopolymerizable compositions described herein exhibits a hydrophilic-lipophilic balance (HLB) value of less than 10, 9 or less, 8 or less, 7 or less, 6 or less, 5 or less, 4 or less, 3 or less, or 2 or less; and 0.1 or more, 0.25 or more, 0.5 or more, 0.75 or more, or 1 or more.

Suitable free-radically polymerizable monofunctional diluents include phenoxy ethyl(meth)acrylate, phenoxy-2-methylethyl(meth)acrylate, phenoxyethoxyethyl(meth)acrylate, 3-hydroxy-2-hydroxypropyl(meth)acrylate, benzyl (meth)acrylate, phenylthio ethyl acrylate, 2-naphthylthio ethyl acrylate, 1-naphthylthio ethyl acrylate, 2,4,6-tribromophenoxy ethyl acrylate, 2,4-dibromophenoxy ethyl acrylate, 2-bromophenoxy ethyl acrylate, 1-naphthyloxy ethyl acrylate, 2-naphthyloxy ethyl acrylate, phenoxy 2-methylethyl acrylate, phenoxyethoxyethyl acrylate, 3-phenoxy-2-hydroxy propyl acrylate, 2,4-dibromo-6-sec-butylphenyl acrylate, 2,4-dibromo-6-isopropylphenyl (meth)acrylate, benzyl (meth)acrylate, phenyl (meth)acrylate, tetrahydrofurfuryl (meth)acrylate, alkoxylated tetrahydrofurfuryl acrylate, ethoxylated nonyl phenol (meth)acrylate, alkoxylated lauryl (meth)acrylate, alkoxylated phenol (meth)acrylate, stearyl (meth)acrylate, tetrahydrofurfuryl (meth)acrylate, lauryl (meth)acrylate, isodecyl (meth)acrylate, isooctyl (meth)acrylate, octadecyl (meth)acrylate, tridecyl (meth) acrylate, ethoxylated (4) nonyl phenol (meth)acrylate, caprolactone (meth)acrylate, cyclic trimethylolpropane formal (meth)acrylate, 3,3,5-trimethylcyclohexyl (meth)acrylate, dicyclopentadienyl (meth)acrylate, isobutyl (meth) acrylate, n-butyl (meth)acrylate, ethyl hexyl (meth)acrylate, isobornyl (meth)acrylate, and 2,4,6-tribromophenyl (meth) acrylate.

In some embodiments, the photopolymerizable composition comprises one or more "high Tg" monofunctional (meth)acrylate monomers, i.e. wherein a cured homopolymer of such monofunctional (meth)acrylate monomer has a Tg of at least 60, 65, 70, 75, 80, 85 or 90° C. In some embodiments, the polymerizable composition comprises at least one of monofunctional (meth)acrylate monomer wherein a cured homopolymer of such monofunctional (meth)acrylate monomer has a Tg of at least 95, 100, 105, 110, 115, 120, 125, 130, 135, 140, 145, 150, 155, 160, 165, 170, 175, 180, 185 or 190° C. The Tg of the homopolymer of the monofunctional (meth)acrylate monomer is typically no greater than about 260° C. For example, 1-adamantyl methacrylate decomposes at about 260° C. In some embodiment, the Tg of the homopolymer of the monofunctional (meth)acrylate monomer is no greater than 255, 250, 245, 240, 235, 230, 225, 220, 215, 210, 205 or 200° C.

Often, the Tg of a homopolymer of a monomer is known from published literature. Table 1 describes the Tg of the homopolymer of various monofunctional (meth)acrylate monomers that may be used in the polymerizable composition of the orthodontic articles described herein. In some embodiments, a single isomer may be used. In other embodiments, a mixture of isomers may be used. Combinations of monofunctional (meth)acrylate monomer(s) can be utilized. In some embodiments, the monofunctional (meth)acrylate monomer is a methacrylate.

In some embodiments, the high Tg monofunctional (meth)acrylate monomer comprises a cyclic moiety. Although the cyclic moiety may be aromatic, in typical embodiments, the cyclic moiety is a cycloaliphatic. Suitable monofunctional (meth)acrylate monomers include for instance and without limitation, 3,3,5-trimethylcyclohexyl (meth)acrylate, butyl-cyclohexyl(meth)acrylate, 2-decahydronapthyl (meth)acrylate, 1-adamantyl (meth)acrylate, dicyclopentadienyl (meth)acrylate, bornyl (meth)acrylate including isobornyl (meth)acrylate, dimethyl-1-adamantyl (meth)acrylate, and 3-tetracyclo[4.4.0.1.1]dodecyl methacrylate.

When the polymerized composition contacts an aqueous environment during normal use, such as in the case of orthodontic articles, it is advantageous to utilize materials that have low affinity for water. One way to express the affinity for water of (meth)acrylate monomers is by calculation of the partition coefficient between water and an immiscible solvent, such as octanol. This can serve as a quantitative descriptor of hydrophilicity or lipophilicity. The octanol/water partition coefficient can be calculated by software programs such as ACD ChemSketch, (Advanced Chemistry Development, Inc., Toronto, Canada) using the log P module. In some embodiments, the monofunctional (meth)acrylate monomer has a calculated log P value of greater than 1, 1.5, 2, 2.5, or 3. In some embodiments, the monofunctional (meth)acrylate monomer has a calculated log P value of greater than 3.5, 4. 4.5, or 5. The calculated log P value is typically no greater than 12.5. In some embodiments, the calculated log P value is no greater than 12, 11.5, 11, 10.5, 10, 9.5, 9, 8.5, 8, 7.5, 7, 6.5, 6, or 5.5.

In some embodiments, the polymerizable composition optionally further comprises a monofunctional (meth)acrylate monomer having a high affinity for water, i.e. having a log P value of less than 3, 2.5, 2.0, 1.5, or 1. When present such monomer(s) are present, such monomer(s) having a high affinity for water are typically present in an amount less than the monofunctional (meth)acrylate monomer(s) having a low affinity for water. Thus, the concentration of monofunctional (meth)acrylate monomer(s) having a high affinity for water is typically no greater than 50, 45, 40, 35, 30, or 25 wt. % of the total monofunctional (meth)acrylate monomer(s). In some embodiments, the concentration of monofunctional (meth)acrylate monomer(s) having a high affinity for water is no greater than 24, 23, 22, 21, 20, 19, 18, 17, 16, 15, 14, 13, 12, 11, 10, 9, 8, 7, 6, 5, 4, 3, 2, or 1 wt. % of the total monofunctional (meth)acrylate monomer(s).

TABLE 1

Reported glass transition temperature ($T_g$) and calculated log P (log of octanol/water partition coefficient) of homopolymers of monofunctional (meth)acrylate monomers.

| Monomer | $T_g$ (° C.) | $T_g$ Reference | Calculated log P |
|---|---|---|---|
| 3,3,5-trimethylcyclohexyl acrylate | 15 | Hopfinger et. al.; J. Polym. Sci. B., Polym. Phys. 1988, 26, 2007 | 4.38 |
| d,l-isobornyl acrylate | 94 | Jakubowski et. al. Polymer, 2008, 49, 1567 | 4.22 |
| dicyclopentanyl acrylate | 103 | U.S. Pat. No. 4,591,626 | 3.69 |
| 3,5-dimethyl-1-adamantyl acrylate | 105 | Matsumoto, A. et. al. Macromolecules 1991, 24, 4017 | 4.63 |
| cyclohexyl methacrylate | 107 | Wilson, P.S., Simha, R.; Macromolecules, 1973, 95, 3, 902 | 3.41 |
| tert-butyl methacrylate | 113 | Matsumoto, A. et. al. Macromolecules 1991, 24, 4017 | 2.57 |
| 3,3,5-trimethylcyclohexyl methacrylate | 125 | Hopfinger et. al.; J. Polym. Sci. B., Polym. Phys. 1988, 26, 2007 | 4.93 |
| cis-4-tert-butyl-cyclohexylmethacrylate | 132 | Matsumoto, A. et. al. Macromolecules 1993, 26, 7, 1659 | 5.13 |
| 2-decahydronapthyl methacrylate | 145 | Matsumoto, A. et. al., J. Polym. Sci. A., Polym. Chem. 1993, 31, 2531 | 4.95 |
| 1-adamantyl acrylate | 153 | Matsumoto, A. et. al. Macromolecules 1991, 24, 4017 | 3.68 |
| Mixture of 73% trans-4-tert-butylcyclohexylmethacrylate/27% cis-4-tert-butylcyclohexylmethacrylate | 163 | Matsumoto, A. et. al. Macromolecules 1993, 26, 7, 1659 | 5.13 |
| dicyclopentanyl methacrylate | 173 | U.S. Pat. No. 4,591,626 | 4.24 |
| trans-4-tert-butylcyclohexyl methacrylate | 178 | Matsumoto, A. et. al. Macromolecules 1993, 26, 7, 1659 | 5.13 |
| d,l-isobornyl methacrylate | 191 | Matsumoto, A. et. al., J. Polym. Sci. A., Polym. Chem. 1993, 31, 2531 | 4.77 |
| 3,5-dimethyl-1-adamantyl methacrylate | 194 | Matsumoto, A. et. al. Macromolecules 1991, 24, 4017 | 5.19 |
| d,l-bornyl methacrylate | 194 | Matsumoto, A. et. al., J. Polym. Sci. A., Polym. Chem. 1993, 31, 2531 | 4.77 |
| 3-tetracyclo[4.4.0.1.1]dodecyl methacrylate | 199 | Matsumoto, A. et. al., J. Polym. Sci. A., Polym. Chem. 1993, 31, 2531 | 4.66 |
| 1-adamantyl methacrylate | >253 | Matsumoto, A. et. al. Macromolecules 1991, 24, 4017 | 4.23 |
| 2-ethylhexyl methacrylate | −10 | Fleischhaker et. al., Macromol. Chem. Phys. 2014, 215, 1192. | 4.88 |
| tetrahydrofurfuryl methacrylate | 60 | E.I. du Pont de Nemours & Co., Ind. Eng. Chem., 1936, 28, 1160, | 1.38 |
| 2-phenoxyethyl methacrylate | 47 | Song et. al.; J. Phys. Chem. B 2010, 114, 7172 | 3.26 |
| N-vinyl pyrrolidone | 180 | Turner et. al; Polymer, 1985, 26, 757 | 0.37 |
| carboxyethyl acrylate | <30 | Fang et. al.; Int. J. Adhes. and Adhes. 84 (2018) 387-393 | 0.60 |
| 2-hydroxyethyl methacrylate | 105 | Russell et. al.; J. Polym. Sci. Polym. Phys, 1980, 18, 1271 | 0.50 |
| acryloyl morpholine | 147 | Elles, J.; Chimie Moderne, 1959, 4, 26, 53 | −0.94 |

The selection and concentration of components including the monofunctional (meth)acrylate monomer(s) contributes to providing a polymerized composition that yields and exhibits a sufficient elongation (e.g. at least 15-20+%). In typical embodiments, the high Tg monofunctional (meth)acrylate monomer(s) also contributes to improving the 3-point bend modulus at 2% strain. When the Tg of the monofunctional (meth)acrylate monomer(s) is too low, the cured compositions may not have the properties needed to move teeth. When the log P values of the monofunctional (meth)acrylate monomer(s) is too low, the polymerized composition may lose its strength when exposed to aqueous environments. When the amount of high Tg monofunctional (meth)acrylate monomer(s) is too high, the polymerized composition can also be too brittle, failing to yield after soaking in water and exhibiting insufficient elongation.

In some embodiments, a monofunctional reactive diluent acts as a compatibilizer, which improves the interfacial adhesion between two otherwise immiscible (i.e. incompatible) material phases (e.g., the urethane component and one or more other reactive diluent(s)). The amount of compatibilizer used is relative to the amount of the urethane component. In some embodiments, a monofunctional reactive diluent compatibilizer is present in a photopolymerizable composition in an amount of 30 wt. % or greater of the amount of the at least one urethane component, or 35 wt. % or greater, or 40 wt. % or greater, of the amount of the at least one urethane component. In certain embodiments of the photopolymerizable composition, the presence of a compatibilizer enables the composition to be a (miscible, i.e. compatible) blend instead of more than one substantially separate phase. Some monofunctional reactive diluents that can act as compatibilizers include for instance phenoxy ethyl (meth)acrylate, tetrahydrofurfuryl (meth)acrylate, and n-vinyl pyrrolidone.

Suitable free-radically polymerizable multifunctional reactant diluents include di-, tri-, or other poly-acrylates and methacrylates such as glycerol diacrylate, ethoxylated bisphenol A dimethacrylate (D-zethacrylate), tetraethylene glycol dimethacrylate (TEGDMA), polyethyleneglycol dimethacrylate (PEGDMA), glycerol triacrylate, ethyleneglycol diacrylate, diethyleneglycol diacrylate, triethyleneglycol dimethacrylate, 1,3-propanediol diacrylate, 1,3-propanediol dimethacrylate, trimethylolpropane triacrylate, 1,2,4-butanetriol trimethacrylate, 1,4-cyclohexanediol diacrylate, pentaerythritol triacrylate, pentaerythritol tetraacrylate, pentaerythritol tetramethacrylate, sorbitol hexacrylate, bis[1-(2-acryloxy)]-p-ethoxyphenyldimethylmethane, bis[1-(3-acryloxy-2-hydroxy)]-p-propoxyphenyldimethylmethane, and trishydroxyethyl-isocyanurate trimethacrylate; bis-acrylates of polyesters (e.g., methacrylate-terminated polyesters); the bis-acrylates and bis-methacrylates of polyethylene glycols of molecular weight 200-500, copolymerizable mixtures of acrylated monomers such as those in U.S. Pat. No. 4,652,274 (Boettcher et al.), and acrylated oligomers such as those of U.S. Pat. No. 4,642,126 (Zador et al.); polyfunctional (meth)acrylates comprising urea or amide groups, such as those of EP2008636 (Hecht et al.).

The reactive diluent can comprise one or more poly(meth) acrylates, for example, di-, tri-, tetra- or pentafunctional monomeric or oligomeric aliphatic, cycloaliphatic or aromatic acrylates or methacrylates.

Examples of suitable aliphatic poly(meth)acrylates having more than two (meth)acrylate groups in their molecules are the triacrylates and trimethacrylates of hexane-2,4,6-triol; glycerol or 1,1,1-trimethylolpropane; ethoxylated or propoxylated glycerol or 1,1,1-trimethylolpropane; and the hydroxyl-containing tri(meth)acrylates which are obtained by reacting triepoxide compounds, for example the triglycidyl ethers of said triols, with (meth)acrylic acid. It is also possible to use, for example, pentaerythritol tetraacrylate, bistrimethylolpropane tetraacrylate, pentaerythritol monohydroxytriacrylate or -methacrylate, or dipentaerythritol monohydroxypentaacrylate or -methacrylate.

Another suitable class of free radical polymerizable compounds includes aromatic di(meth)acrylate compounds and trifunctional or higher functionality (meth)acrylate compound. Trifunctional or higher functionality meth(acrylates) can be tri-, tetra- or pentafunctional monomeric or oligomeric aliphatic, cycloaliphatic or aromatic acrylates or methacrylates.

Examples of suitable aliphatic tri-, tetra- and pentafunctional (meth)acrylates are the triacrylates and trimethacrylates of hexane-2,4,6-triol; glycerol or 1,1,1-trimethylolpropane; ethoxylated or propoxylated glycerol or 1,1,1-trimethylolpropane; and the hydroxyl-containing tri(meth) acrylates which are obtained by reacting triepoxide compounds, for example the triglycidyl ethers of said triols, with (meth)acrylic acid. It is also possible to use, for example, pentaerythritol tetraacrylate, bistrimethylolpropane tetraacrylate, pentaerythritol monohydroxytriacrylate or -methacrylate, or dipentaerythritol monohydroxypentaacrylate or -methacrylate. In some embodiments, tri(meth) acrylates comprise 1,1-trimethylolpropane triacrylate or methacrylate, ethoxylated or propoxylated 1,1,1-trimethylolpropanetriacrylate or methacrylate, ethoxylated or propoxylated glycerol triacrylate, pentaerythritol monohydroxy triacrylate or methacrylate, or tris(2-hydroxy ethyl) isocyanurate triacrylate. Further examples of suitable aromatic tri(meth)acrylates are the reaction products of triglycidyl ethers of trihydroxy benzene and phenol or cresol novolaks containing three hydroxyl groups, with (meth) acrylic acid.

In some cases, a reactive diluent comprises diacrylate and/or dimethacrylate esters of aliphatic, cycloaliphatic or aromatic diols, including 1,3- or 1,4-butanediol, neopentyl glycol, 1,6-hexanediol, dodecane diol, diethylene glycol, triethylene glycol, tetraethylene glycol, polyethylene glycol, tripropylene glycol, ethoxylated or propoxylated neopentyl glycol, 1,4-dihydroxymethylcyclohexane, 2,2-bis(4-hydroxycyclohexyl)propane or bis(4-hydroxycyclohexyl) methane, hydroquinone, 4,4'-dihydroxybiphenyl, bisphenol A, bisphenol F, bisphenol S, ethoxylated or propoxylated bisphenol A, ethoxylated or propoxylated bisphenol F or ethoxylated or propoxylated bisphenol S. In some cases, a reactive diluent described herein comprises one or more higher functional acrylates or methacrylates such as dipentaerythritol monohydroxy pentaacrylate or bis(trimethylolpropane)tetraacrylate.

In some embodiment comprising a multifunctional reactive diluent, one or more multifunctional reactive diluents are present in an amount of 1 to 30 wt. %, inclusive, such as 5 to 20 wt. %, based on the total weight of the photopolymerizable composition. Stated another way, at least one multifunctional reactive diluent may be present in an amount of 1 wt. % or more, 3 wt. % or more, 5 wt. % or more, 10 wt. % or more, or 15 wt. % or more; and 30 wt. % or less, 25 wt. % or less, 20 wt. % or less, or 17 wt. % or less, based on the total weight of the photopolymerizable composition.

In certain other embodiments, the photopolymerizable composition consists essentially of monofunctional components or is free of multifunctional components. This means that the photopolymerizable composition contains 2 wt. % or less of multifunctional components. It was unexpectedly discovered that a significant amount of the monofunctional reactive diluents are incorporated into the reaction product of the photopolymerizable composition during photopolymerization. This means that a relatively small amount of unreacted monofunctional reactive diluent remains in the reaction product and could be extracted from the cured composition, particularly after subjection of the cured composition to a post-cure step.

In select embodiments, two or more reactive diluents are prepolymerized such that up to 10%, up to 15%, or up to 20% of the functional groups of the reactive diluents are reacted prior to inclusion in the photopolymerizable composition. The prepolymerization is typically performed via initiation with a small amount of photoinitiator added to the reactive diluents. One representative prepolymerization process is described in detail in the Examples below. An advantage of prepolymerizing a portion of the reactive diluent(s) is the formation of a semi-interpenetrative polymer network. Also, the prepolymerization tends to assist in producing higher molecular weight chains in the reaction product of the photopolymerizable composition as compared to the same composition that is not prepolymerized.

In certain embodiments, the at least one reactive diluent has a molecular weight of 400 grams per mole or less, 375 g/mol or less, 350 g/mol or less, 325 g/mol or less, 300 g/mol or less, 275 g/mol or less, 225 g/mol or less, or 200 g/mol or less. Including one or more reactive diluents with such molecular weights can assist in providing a photopolymerizable composition that has a sufficiently low viscosity for use with vat polymerization methods. In certain embodiments, the at least one reactive diluent comprises a molecular weight of 200 g/mol to 400 g/mol, inclusive.

The (e.g. monofunctional) reactive diluent is included in the photopolymerizable composition in an amount of 25 to 70 wt. %, inclusive, based on the total weight of the photopolymerizable composition. Typically, the reactive diluent is included in the photopolymerizable composition in an amount of 25 wt. % or more, 30 wt. % or more, or 35 wt. % or more; and 70 wt. % or less, 65 wt. % or less, 60 wt. % or less, 55 wt. % or less, 50 wt. % or less, 45 wt. % or less, or 40 wt. % or less, based on the total weight of the photopolymerizable composition. When the photopolymerizable composition comprises filler, the concentration of (e.g. monofunctional) reactive diluent as just described is based of the total free-radically polymerizable resin (excluding the filler).

Initiators

Photopolymerizable compositions described herein, in some instances, further comprise one or more additives, such as one or more additives selected from the group consisting of photoinitiators, thermal initiators, inhibitors, stabilizing agents, sensitizers, absorption modifiers, fillers and combinations thereof. For example, the photopolymerizable composition further comprises one or more photoinitiators, for instance two photoinitiators. Suitable exemplary photoinitiators are those available under the trade designations IRGACURE and DAROCUR from BASF (Ludwigshafen, Germany) and include 1-hydroxycyclohexyl phenyl ketone (IRGACURE 184), 2,2-dimethoxy-1,2-diphenylethan-1-one (IRGACURE 651), bis(2,4,6 trimethylbenzoyl)phenylphosphineoxide (IRGACURE 819), 1-[4-(2-hydroxyethoxy)phenyl]-2-hydroxy-2-methyl-1-propane-1-one (IRGACURE 2959), 2-benzyl-2-dimethylamino-1-(4-morpholinophenyl)butanone (IRGACURE 369), 2-methyl-1-[4-(methylthio)phenyl]-2-morpholinopropan-1-one (IRGACURE 907), Oligo[2-hydroxy-2-methyl-1-[4-(1-methylvinyl)phenyl]propanone] ESACURE KIP 150 (Lamberti S.p.A., Gallarate, Italy), 2-hydroxy-2-methyl-1-phenyl propan-1-one (DAROCUR 1173), 2, 4, 6-trimethylbenzoyl-diphenylphosphine oxide (IRGACURE TPO), and 2, 4, 6-trimethylbenzoylphenyl phosphinate (IRGACURE TPO-L). Additional suitable photoinitiators include for example and without limitation, benzyl dimethyl ketal, 2-methyl-2-hydroxypropiophenone, benzoin methyl ether, benzoin isopropyl ether, anisoin methyl ether, aromatic sulfonyl chlorides, photoactive oximes, and combinations thereof.

A thermal initiator can be present in a photopolymerizable composition described herein in any amount according to the particular constraints of the additive manufacturing process. In some embodiments, a thermal initiator is present in a photopolymerizable composition in an amount of up to about 5% by weight, based on the total weight of the photopolymerizable composition. In some cases, a thermal initiator is present in an amount of about 0.1-5% by weight, based on the total weight of the photopolymerizable composition. Suitable thermal initiators include for instance and without limitation, peroxides such as benzoyl peroxide, dibenzoyl peroxide, dilauryl peroxide, cyclohexane peroxide, methyl ethyl ketone peroxide, hydroperoxides, e.g., tert-butyl hydroperoxide and cumene hydroperoxide, dicyclohexyl peroxydicarbonate, 2,2,-azo-bis(isobutyronitrile), and t-butyl perbenzoate. Examples of commercially available thermal initiators include initiators available from Chemours Co. (Wilmington, DE) under the VAZO trade designation including VAZO 67 (2,2'-azo-bis(2-methybutyronitrile)) VAZO 64 (2,2'-azo-bis (isobutyronitrile)) and VAZO 52 (2,2'-azo-bis(2,2-dimethyvaleronitrile)), and LUCIDOL 70 from Elf Atochem North America, Philadelphia, PA.

In certain aspects, the use of more than one initiator assists in increasing the percentage of reactive diluent that is incorporated into the reaction product and thus decreasing the percentage of the reactive diluent that remains uncured. Reaction of monofunctional reactive diluent(s) in particular is desirable to minimize the presence of unreacted diluent in the product following polymerization.

In certain embodiments, the orthodontic article or cured photopolymerized composition comprises 2 wt. % or less extractable components, 1 wt. % or less, 0.75 wt. % or less, 0.5 wt. % or less, or even 0.1% or less extractable components, based on the total weight of the article. Either an organic solvent (e.g. heptane) or a solution of 5% ethanol and water can be used to extract component, as described in detail in the Examples below. Post-processing of the article to assist in achieving a low extractable component-containing article is discussed in more detail below. In some embodiments, the heptane extractables is less than 1, 0.75, 0.5, 0.4, 0.3, or 0.2% based on the total weight of the article. In some embodiments, the heptane extractables is less than 0.1, 0.09, 0.08, 0.07, 0.06, 0.05, 0.04, 0.03, or 0.02% based on the total weight of the article.

In some embodiments, the first and second photoinitiators are each present in an amount of at least 0.1, 0.2, 0.3, 0.4, or 0.5 wt. %, based on the total weight of the free-radical polymerizable resin. In some embodiments, the first and second photoinitiators are each present in an amount no greater than 2.5, 2.4, 2.3, 2.2, 2.1, 2.0, 1.9, 1.8, 1.7, 1.6, or 1.5 wt. %. In other embodiments, the first photointiator and second thermal initiator are each present in an amount of at least 0.1, 0.2, 0.3, 0.4, or 0.5 wt. %, based on the total weight of the free-radical polymerizable resin. In some embodiments, the first and second photoinitiators are each present in an amount no greater than 2.5, 2.4, 2.3, 2.2, 2.1, 2.0, 1.9, 1.8, 1.7, 1.6, or 1.5 wt. %.

In some embodiments, the photopolymerizable composition comprises at least two different photoinitiators selected based on absorbance properties of the photoinitiators.

The absorbance of a photoinitiator solution can be determined using a spectrophotometer (according the test method described in the examples). The solvent of the photoinitiator solution is suitable for dissolving the photoinitiator. In typical embodiments, acetonitrile is a suitable solvent. The concentration of photoinitiator dissolved in the solution for determining the absorbance is sufficiently high such that the measured absorbance is greater than the baseline "noise". In typical embodiments, a concentration of 1 g/liter is useful for determining the absorbance properties of a photoinitiator. However, when the photoinitiator is a polymer comprising one or more photoinitiator groups, the concentration is typically adjusted such that the solution contains 1 g of photoinitiator groups per liter. For example, when the polymer comprising one or more photoinitiator groups comprises about 10 grams of polymerized units comprising photoinitiator groups and 30 grams of polymerized units of other monomers (i.e. lacking photoinitiator groups), 4 grams/liter of such polymeric photoinitiator would be equal to 1 gram/ liter of photoinitiator groups/liter. The absorbance of some acetonitrile photoinitiator solutions are described in the literature. One of ordinary skill in the art appreciates that there is a linear relationship between absorbance and concentration. Therefore, by measuring the absorbance at one concentration, the absorbance at other concentrations can be calculated.

The first free-radical photoinitiator has sufficient absorbance at a wavelength of a first wavelength range. In some embodiments, the first wavelength range is 375-450 nm. In some embodiments, the wavelength of absorbance of the first free-radical photoinitiator is 385 nm.

One class of first free-radical photoinitiators having sufficient absorbance at a wavelength of the first wavelength range (e.g. 375-400 nm) are phosphine oxides. Some illustrative phosphine oxide photoinitiators are depicted as follows:

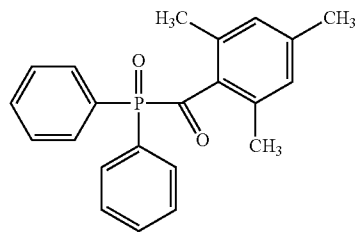

diphenyl-(2,4,6,-trimethylbenzoyl)-phosphine oxide,

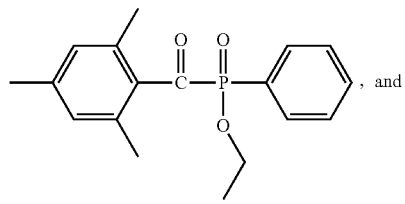, and ethyl-(2,4,6,-trimethylbenzoyl)-phosphine oxide

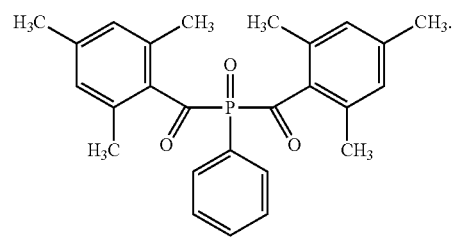

phenyl-bis-(2,4,6,-trimethylbenzoyl)-phosphine oxide.

Phosphine oxide photoinitiator typically comprise a phosphorous atom double bonded to oxygen. The phosphorous atom is also typically bonded to a phenyl group and a benzoyl group. In some embodiments, the phosphorous atom is bonded to two phenyl groups and a (e.g. trimethyl) benzoyl group. In some embodiments, the phosphorous atom is bonded to a phenyl group, an (e.g. $C_1$-$C_4$) alkoxy group and a (e.g. trimethyl)benzoyl group. In some embodiments, the phosphorous atom is bonded to a phenyl group and two (e.g. trimethyl)benzoyl groups. Such phosphine oxide photoinitiators are also referred to as acyl phosphine oxides.

Another class of first free-radical photoinitiators having sufficient absorbance at a wavelength of the first wavelength range (e.g. 375-400 nm) are alkyl amino acetophenones. Some illustrative alkyl amino acetophenones are depicted as follows:

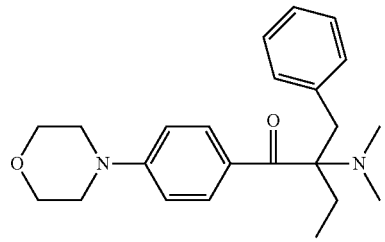 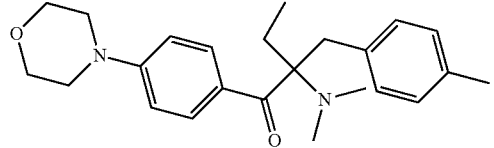

2-benzyl-2-dimethylamino-1-(4-morpholinophenyl)-butanone-1,     2-dimethylamino-2-(4-methyl-benzyl)-1-(4-morpholin-4-yl-phenyl)-butan-1-one,

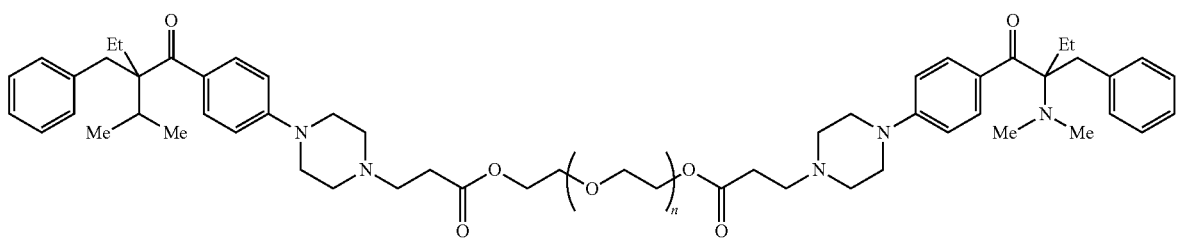

commercially available as Omnipol 910 having a molecular weight of 1039 g/mole (n=3) and a peak absorption wavelength of 325 nm. In this embodiment, the photoinitiator is a polymer comprising a polyalkylene oxide (e.g. polyethylene oxide) polymer and two terminal photoinitiator groups.

Photoinitiators are often characterized according to absorption wavelength maximums or in other words absorption peaks. For example, absorption wavelength maximums are reported for various photoinitiators in *Industrial Photoinitiators, A Technical Guide*, W Arthur Green, CRC Press, Taylor and Francis Group, 2010.

The absorbance of some illustrative phosphine oxide photoinitiators, as reported in Industrial Photoinitiators, as described in the following table.

TABLE 1

First Photoinitiators for 375-450 wavelength range

| Tradename | Chemical Description | Molecular Weight | Measured Absorbance at 385 nm (1 g/liter) | Absorption Wavelengths Maximums (nm) |
|---|---|---|---|---|
| TPO | diphenyl-(2,4,6,-trimethylbenzoyl)-phosphine oxide | 348 g/mole | 1.5 | 275, 379 |
| TPO-L | ethyl-(2,4,6,-trimethylbenzoyl)-phosphine oxide | 316 g/mole | 0.5 | 270, 370 |
| IRGACURE 819 | phenyl-bis-(2,4,6,-trimethylbenzoyl) phosphine oxide | 418 g/mole | | 275, 377 |
| IRGACURE 369 | 2-benzyl-2-dimethylamino-1-(4-morpholinophenyl)-butanone-1 | 367 g/mole | 1.3 | 233, 320 |
| IRGACURE 379 | 2-dimethylamino-2-(4-methyl-benzyl)-1-(4-morpholin-4-yl-phenyl)-butan-1-one | 381 g/mole | 1.4 | 233, 320 |

A 1 g/liter acetonitrile solution of the first free-radical photoinitiator spectrophotometer at a pathlength of 1 cm typically has an absorbance of greater than 0.01, 0.02, 0.03, 0.04, 0.05, 0.06, 0.07, 0.08, 0.09, or 0.10 at a wavelength of the first wavelength range when measured with a. In some embodiments, the first free-radical photoinitiator has an absorbance of greater than 0.2, 0.3, 0.4, or 0.5. In some embodiments, the first free-radical photoinitiator has an absorbance of greater than 1 or 1.5. In typical embodiments, the absorbance is no greater than 3 (for a 1 g/liter acetonitrile solution of the free-radical photoinitiator).

In some embodiments, the first photoinitiator has two absorption wavelength maximums. In some embodiments, the first absorption wavelength maximum ranges from 230 nm-235. The second absorption wavelength maximum ranges from 310 nm-330. In this embodiment, the first photoinitiator does not have an absorption wavelength maximum in the first wavelength range.

In other embodiments, the first absorption wavelength maximum ranges from 270 nm-275. The second absorption wavelength maximum ranges from 370 nm-380. In this embodiment, the first photoinitiator has an absorption wavelength maximum in the first wavelength range.

In some embodiments, such as in the case of (e.g. Omnipol 910) some alkyl amino acetophenone photoinitiators, the first photoinitiator has a single absorption wavelength maximum. Such absorption maximum is between the two absorption wavelength maximums described. In some embodiments, the absorption maximum is near the midpoint between the two absorption wavelength maximums (e.g. 300-330 nm).

Figure 11:
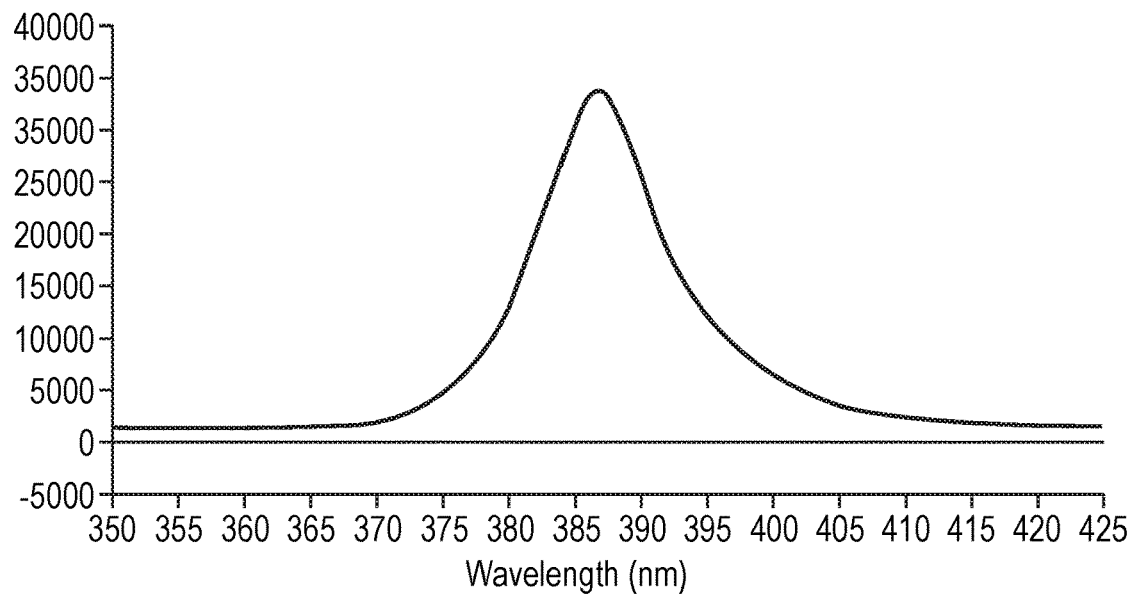
FIG. 11 is a spectrum of wavelength on the x-axis vs light intensity of the y-axis of a photocuring chamber.

In typical embodiments, the orthodontic article is prepared by 3D printing. The photopolymerizable composition is selectively cured by exposure to actinic radiation of the first wavelength range or a portion of the first wavelength range, e.g. 375 nm-410. FIG. 11 is a graph of light intensity as a function of wavelength for an illustrative light source for curing the photopolymerizable composition.

The second free-radical initiator is a thermal initiator or a photoinitiator. When the second free-radical initiator is a photoinitiator, the second free-radical photoinitiator has sufficient absorbance at a second wavelength range. The second wavelength range is a different wavelength range than the first wavelength range. In some embodiments, the second wavelength range is 360 nm up to but not including 375 nm. In some embodiments, the wavelength of absorbance of the second free-radical photoinitiator is 365 nm. Notably, the light source of FIG. 11 has nominally zero light intensity for wavelengths of the second wavelength range. Thus, the second photoinitiator is not activated by exposure to such light source.

One class of second free-radical photoinitiators having the desired absorbance are hydroxy-acetophenones. An illustrative hydroxy acetophenones is depicted as follows:

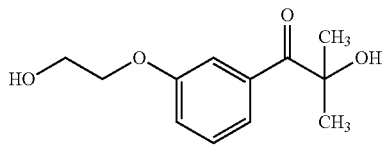

2-hydroxy-4'-(2-hydroxyethoxy)-2-methyl-propiophenone.

Another hydroxy acetophenone is commercially available as Esacure ONE, a mixture of isomers having a molecular weight of 408 g/mole and maximum absorption wavelengths of 260 and 325 nm, depicted as follows:

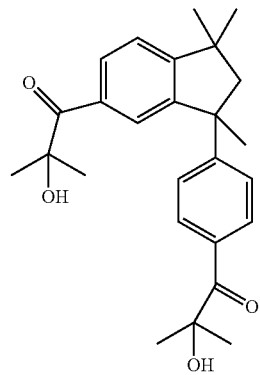 [SMILES: CC(C)(O)C(=O)c1ccc(C2(C)CC(C)(C)c3ccc(C(=O)C(C)(C)O)cc32)cc1]

Esacure ONE is one example of a photoinitiator compound comprising more than one (e.g. two) photoinitiator groups.

Another illustrative hydroxy-acetephenone photoinitiator is commercially available as Esacure KIP 150 and Chivacure 300. Such photoinitiator has the following formula:

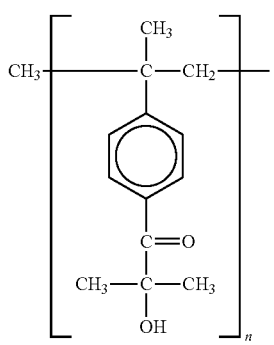

wherein n ranges from 2-5, having a molecular weight of at least 800 g/mole. In this embodiment, the photoinitiator is a polymer comprising a polyolefin backbone and (e.g. 2-5) pendent photoinitiator groups.

Another class of second free-radical photoinitiators having the desired absorbance are benzil ketals.

An illustrative benzil ketal photoinitiator is 2,2-dimethoxy-2-phenyl-acetophenone benzil dimethyl ketal, commercially available as Irgacure 651 is depicted as follows. Such photoinitiator has a molecular weight of 256 g/mole and peak absorption wavelength of 252 and 335 nm.

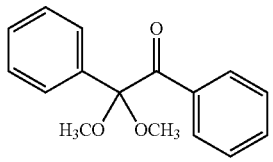 [SMILES: COC(OC)(C(=O)c1ccccc1)c1ccccc1]

The absorbance of some illustrative second photoinitiators, as reported in Industrial Photoinitiators, is described in the following table.

TABLE 2

Second Photoinitiators for 360-375 wavelength range

| Tradename | Chemical Description | Measured Absorbance at 385 nm (1 g/liter) | Measured Absorbance at 365 nm (1 g/liter) | Absorption Peak Wavelength (nm) |
|---|---|---|---|---|
| IRGACURE 2959 Mw = 224 g/mole | 2-hydroxy-4'-(2-hydroxyethoxy)-2-methyl-propiophenone | 0.01 | 0.1 | 273, 330 |
| Esacure KIP 150 | Oligo 2-hydroxy-2-methyl-1-[4-(1-methyl-vinyl)phenyl]propane | 0.01 | 0.1 | 262, 330 |
| Chivacure 300 | Oligo 2-hydroxy-2-methyl-1-[4-(1-methyl-vinyl)phenyl]propane | 0.01 | 0.1 | |

A 1 g/liter acetonitrile solution of the second photoinitiator at a pathlength of 1 cm has an absorbance of greater than 0.01, 0.02, 0.03, 0.04, 0.05, 0.06, 0.07, 0.08, 0.09, or 0.10 a wavelength of the second wavelength range when measured with a spectrophotometer. In typical embodiments, the absorbance is no greater than 3 (for a 1 g/liter acetonitrile solution of the free-radical photoinitiator).

The second photoinitiator has an absorbance of less than 0.1, 0.09, 0.08, 0.07, 0.06, 0.05, 0.04, 0.03, 0.02, or 0.01 at a wavelength (e.g. 385 nm) of the first wavelength range.

The second photoinitiator typically has two absorption wavelength maximums. The first absorption wavelength maximum ranges from 250 nm-275. The second absorption wavelength maximum ranges from 325 nm-330 nm. In some embodiments, the second photoinitiator does not have an absorption wavelength maximum in the second wavelength range. However, the second photoinitiator provides sufficient absorbance at 365 nm.

In some embodiments, the first photoinitiator has an absorbance at 385 nm greater than the second photoinitiator by a factor of 5× ranging up to 10×, 50×, 100×, 150×, 200×, 250×, or 300×.

Figure 12:
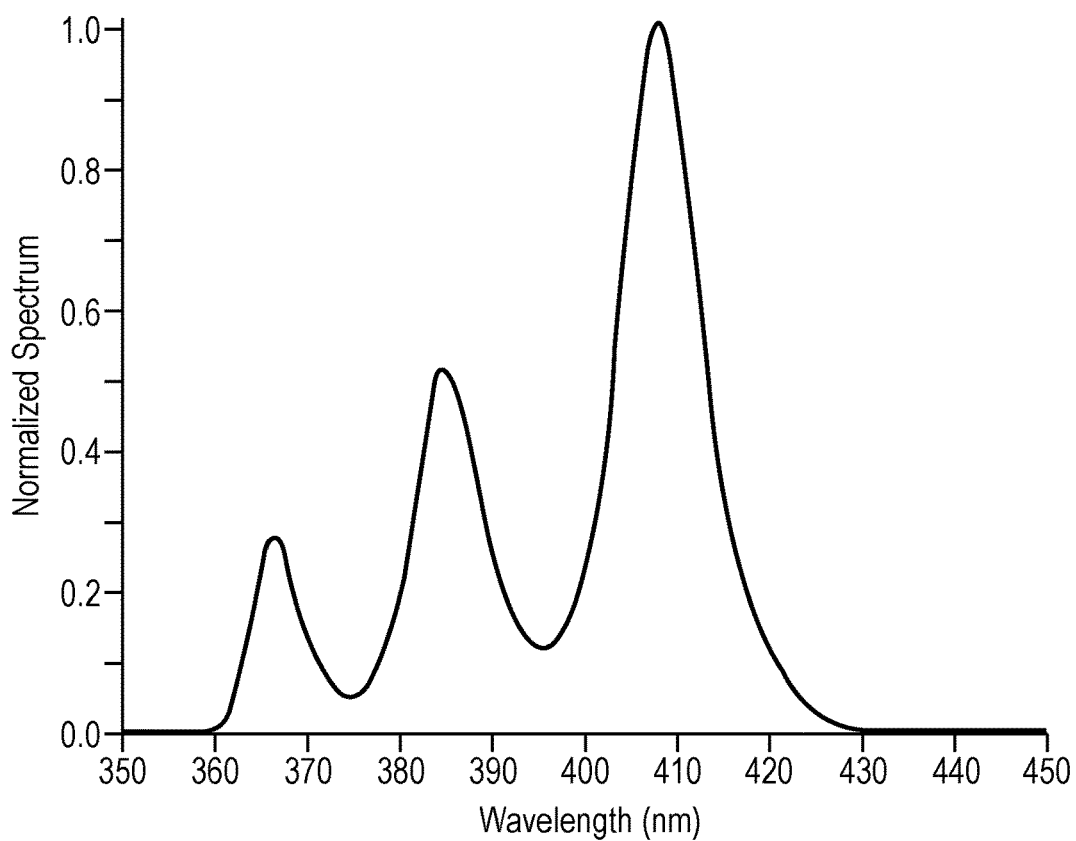
FIG. 12 is a normalized spectrum of light intensity of a post curing chamber.

In typical embodiments, the orthodontic article is subjected to post curing using actinic radiation or heat. When the orthodontic article is subjected to post curing using photocuring, the orthodontic article is post cured by exposure to light of the second wavelength range or a portion of the second wavelength range. FIG. 12 is a graph of a normalized spectrum as a function of wavelength for an illustrative light source for post curing the predominantly cured photopolymerizable composition of the orthodontic article. Notably the post curing can also include actinic radiation of the first wavelength range in the event a portion of the first photoinitiator is present during post curing.

In some embodiments, the photoinitiator may be characterized as a compound, such as in the case of TPO and Irgacure 2959 described above. In typical embodiments, such compounds have a molecular weight of less than 500 g/mole. In some embodiments, the photoinitiator compound may comprise at least two photoinitiator groups, such as in the case of TPO-L and Esacure ONE.

In the case of polymers and macromolecules comprising one or more free-radical photoinitiator groups, the molecular weight (Mn) is typically at least 500 g/mole. In some embodiments, the molecular weight is at least 750, 1000, 1250, or 1500 g/mole. The molecular weight (Mn) of a macromolecule is typically no greater than 4000, 3500, 3000, 2500, or 2000 g/mole.

In some embodiments, the photoinitiator macromolecules have the formula:

$$R^{10}-(PI)_x,$$

where
$R^{10}$ is a polyvalent (hetero)hydrocarbyl group,
x is at least 2 and
PI is a photoinitiator group represented by the structure:

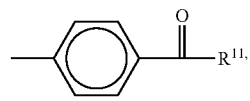

wherein $R^{11}$ is

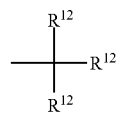

at least one $R^{12}$ is hydroxyl or a $C_1$ to $C_6$ alkoxy group, and the other $R^{12}$ groups are independently phenyl group or $C_1$ to $C_6$ alkyl group.

As described in WO 2018/152076; incorporated herein by reference, polyfunctional photoinitiators can be made by reaction of: 1) (hetero)hydrocarbyl compound comprising two or more first reactive functional group with 2) a compound that comprises an alpha-cleavage photoinitiator group) and second reactive functional group, the two functional groups being co-reactive with each other. Preferred (hetero)hydrocarbyl compounds are aliphatic, cycloaliphatic, and aromatic compounds having up to 36 carbon atoms, optionally one or more oxygen and/or nitrogen atoms, and at least two reactive functional group. When the first and second functional groups react, they form a covalent bond and link the co-reactive compounds.

Representative examples of photoinitiator compounds that can be used to prepare a macromolecule include functional group-substituted compounds such as 1-(4-hydroxyphenyl)-2,2-dimethoxyethanone, 1-[4-(2-hydroxyethyl)phenyl]-2,2-dimethoxyethanone, (4-isocyanatophenyl)-2,2-dimethoxy-2-phenylethanone, 1-{4-[2-(2,3-epoxypropoxy)phenyl]}-2,2-dimethyl-2-hydroxyethanone, 1-[4-(2-aminoethoxy)phenyl]-2,2-dimethoxyethanone, and 1-[4-(carbomethoxy)phenyl]-2,2-dimethoxyethanone.

Representative photoinitiator macromolecules include, for example, the following compounds.

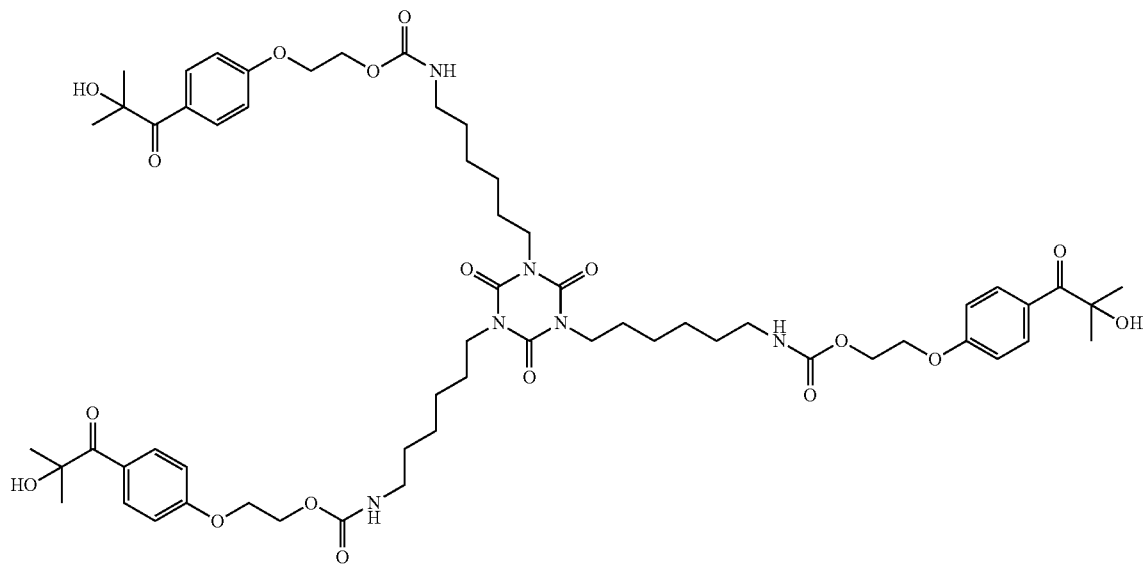

Molecular weight: 1177.36

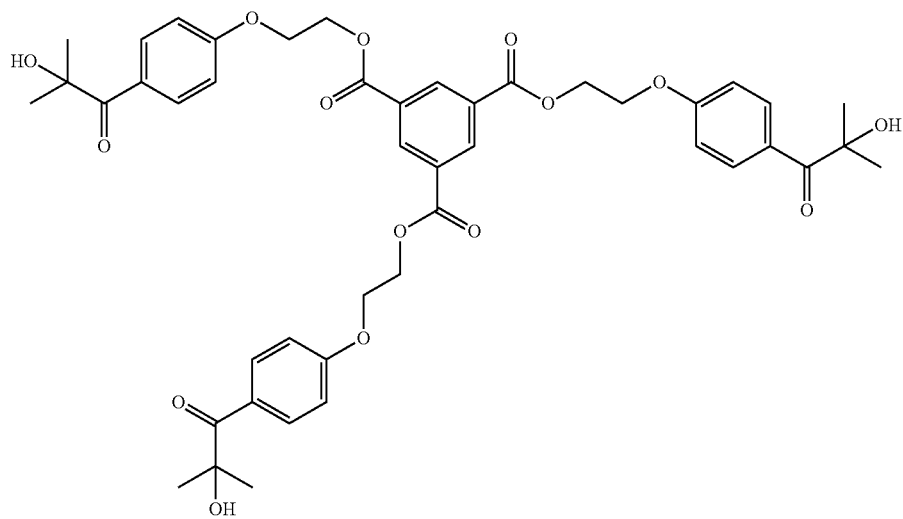

Molecular weight: 828.86

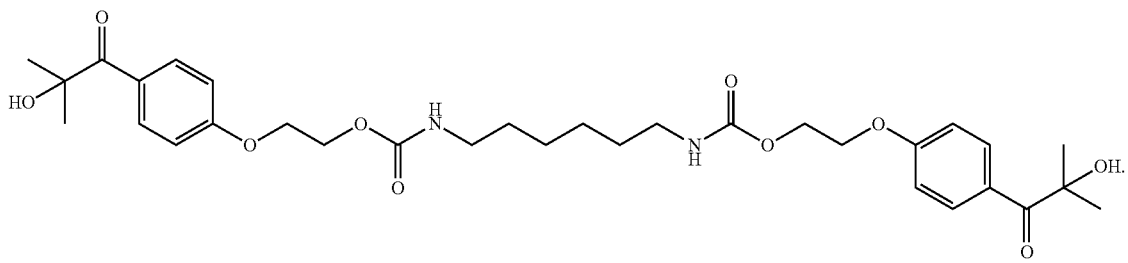

Molecular weight: 616.71

In some embodiments, the second photoinitiator is a polymer comprising one or more photoinitiator groups. As used herein, the term polymer refers to comprising at least 2 or more repeat units. Some polymeric photoinitiators are commercially available such as Omnipol 910, Esacure KIP 150 and Chivacure 300 described above. Since the molecular weight and number of repeat units is relatively low, such polymeric photoinitiators are also characterized as oligomers.

In some embodiments, the molecular weight of the polymer comprising one or more photoinitiator groups can be greater than a macromolecule. In some embodiments, the polymer comprising one or more photoinitiator groups having a molecular weight Mn of greater than 4000, 4500, 5000 g/mole. In some embodiments, the molecular weight Mn is at least 10,000; 15,000; 20,000; or 25,000 g/mole. In some embodiments, Mn of the polymer comprising one or more photoinitiator groups is no greater than 100,000, 75,000, or 50,000 g/mole. The polydispersity of the polymer comprising one or more photoinitiator groups typically ranges 2 to 10. Thus, the weight average molecular weight can be 2×, 3×, 4×, 5×, 6×, 7× or 8× the values just described for the number average molecular weight.

Higher molecular weight macromolecules and polymers with photoinitiator groups and their degradants (i.e. fragments after cleavage) can have low levels of migration upon photolysis (e.g. curing by exposure to UV radiation), resulting in lower extractables and lower odor.

In one embodiment, a urethane component, i.e. having a urethane moiety (e.g., an oligomer or a polymer) may be prepared including one or more pendant groups attached to the oligomer or polymer backbone. Preferably, at least one pendent group comprises a photoinitiator.

For instance, a photoinitiator-containing ethyl acrylate compound (PIEA) has been prepared via the below reaction scheme:

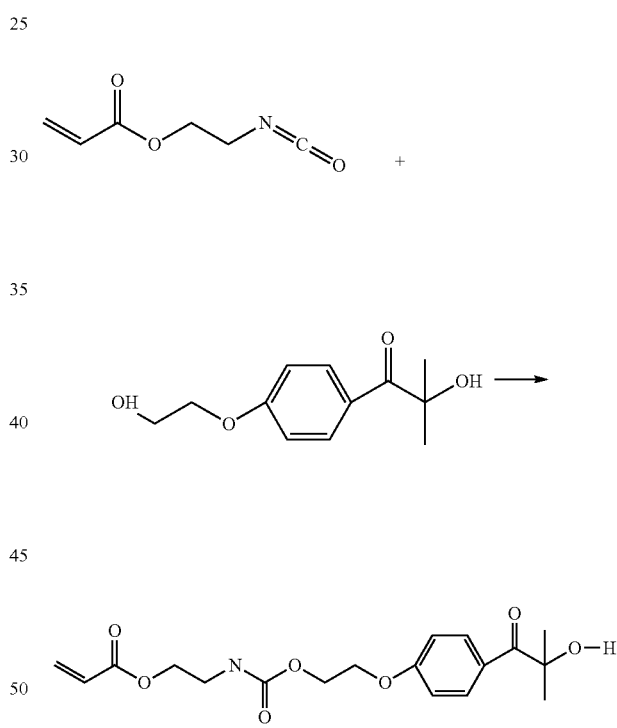

Representative examples of photoinitiator compounds that can be used to prepare a (meth)acrylate functional compound are the same compounds described above that can be used in the preparation of a photoinitiator macromolecule.

Next, the PIEA can be reacted with one or more monomers and a thermal initiator in solution, such as per the below reaction scheme:

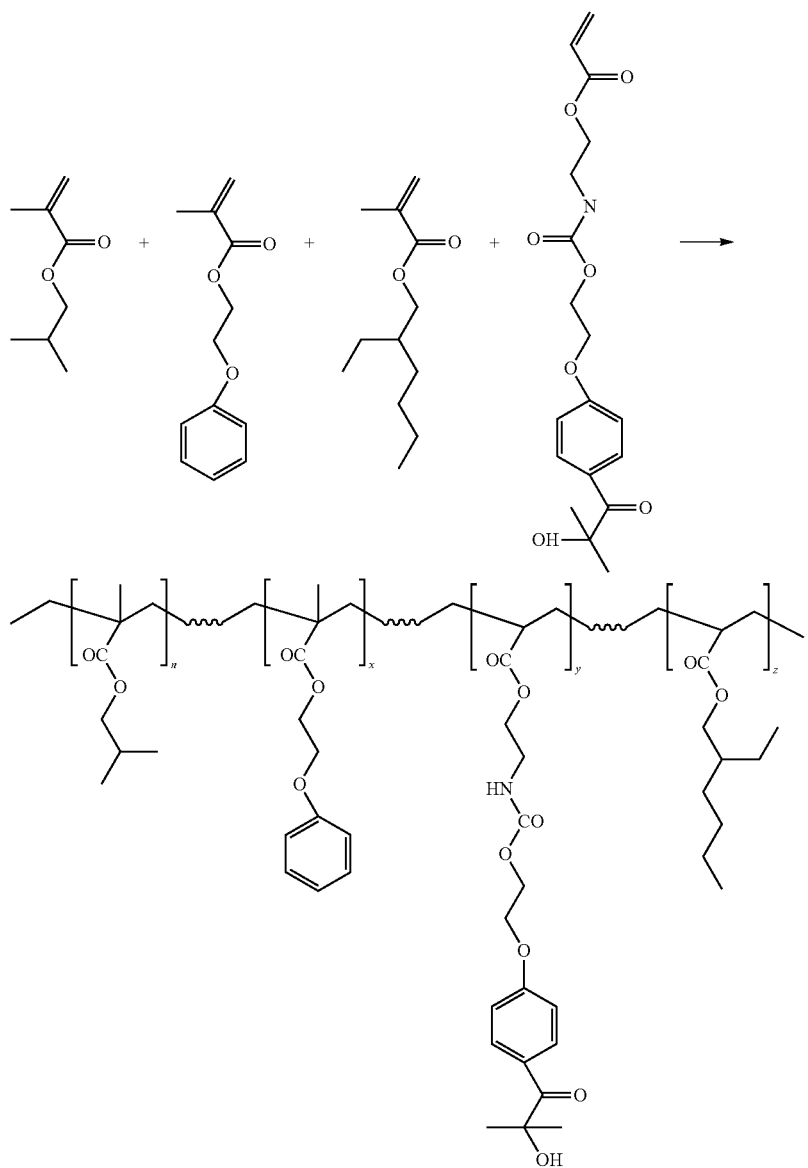

This reaction is also described in detail in the Examples below (preparation of PP1).

This example can be characterized as a poly(meth)acrylate polymer backbone comprising pendent (e.g. hydroxy acetophenone) photoinitiator groups. The pendent (e.g. hydroxy acetophenone) photoinitiator groups are bonded to the polymer backbone via a urethane linking group.

Although a polymer may comprise a single photoinitiator group, the polymer typically comprises two or more photoinitiator groups. In some embodiments, such as in the case of PP1 described above, the photoinitiator groups can range up to 25 wt. % of the total polymeric photoinitiator. In some embodiments, there is at least one photoinitiator group per 500 g/mole, 750 g/mole, or 1,000 g/mole molecular weight (Mn) of the polymeric photoinitiator. In some embodiments, the molecular weight (Mn) per photoinitiator group is no greater than 5000, 4500, 4000, 3500, 3000, 2500, 2000, or 1500 g/mole.

In some embodiments, the second free-radical initiator is a thermal initiator. The thermal initiator preferably has a 10 hour half-life of at least 50, 55, or 60° C. In some embodiments, the 10 hour half-life is not greater than about 150° C. When the photopolymerizable composition is heated to a temperature below the 10 hour half-life (e.g. 40° C., the thermal initiator is not activated. If the thermal initiator is activated while the photopolymerizable composition is in the vat, such activation can cause the photopolymerizable composition to gel. Thermal initiator with such half-life are typically peroxide or azo compounds.

Peroxide initiators typically comprise a single peroxide groups and a molecular weight no greater than 500 grams/mole.

In some embodiments, the initiator is a diacyl peroxides, typically having the formula $R^1-C(=O)-O-O-C(=O)R^1$, wherein IV typically comprises 1 to 20 carbon atoms. $R^1$ can be alkyl including cycloalkyl, aryl, and $-(CH_2)_2-COOH$.

In other embodiments, the initiator is a dialkyl peroxides, typically having the formula $(R^3-O-O)nR^4$; wherein n=1 or 2 and $R^3$ and $R^4$ are independently alkyl, cycloalkyl, and alkaryl; typically comprising 1 to 20 carbon atoms.

In other embodiments, the initiator is a diperoxyketals, typically having the formula $(R^1)(R^2)C(OOR^3)_2$; wherein $R^1$ and $R_2$ independently alkyl, cycloalkyl, alkyl ester; typically comprising 1 to 20 carbon atoms. In some embodiments, $R^1$ and $R^2$ can be taken together with the carbon atom to which they are attached to form a cycloaliphatic hydrocarbon ring having from 4-8 carbon atoms in the ring.

In other embodiments, the initiator is a hydroperoxides, typically having the formula R1-OOH; wherein R1 alkyl, aryl, alkaryl; typically comprising 1 to 20 carbon atoms.

Azo-thermal initiators generally have a nitrogen triple bonded to a nitrogen and a molecular weight no greater than 50 0 grams/mole.

In some embodiments, the azo thermal initiator has the following formula

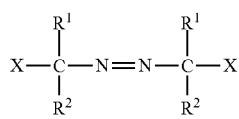

wherein X is a monovalent group such as —CN, —COOR$^3$ and —CONHR$^3$, wherein R$^3$ is hydrogen, alkyl, or hydroxyalkyl); —C(=NH)NR$^4$, where R$^4$ is alkyl, alkyl carboxylate); and

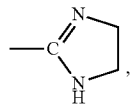

$R^1$ and $R^2$ are independently a $C_1$-$C_{20}$ alkyl group, and $R^2$ is alkyl, alkoxy-functional alkyl, carboxy-functional alky, cycloalkyl, phenyl, benzyl; typically comprising 1 to 20 carbon atoms. In some embodiments, $R^1$ and $R^2$ can be taken together with the carbon atom to which they are attached to form a cycloaliphatic hydrocarbon ring having from 4-8 carbon atoms in the ring.

Some illustrative thermal initiators are described in the following table:

| Chemical name | Trade name | 10 hr half life (° C.) |
|---|---|---|
| 1,1-Di(t-butylperoxy)-3,3,5 trimethylcyclohexane | Luperox 231 | 96 |
| Benzol peroxide | Luperox A98 | 73 |
| Dicumyl peroxide | Luperox DCP | 117 |
| 2,5-Di(t-butylperoxy)-2,5-dimethylhexane | Luperox 101 | 120 |
| t-Butyl cumyl peroxide | Luperox 801 | 124 |
| 2,5-Di(t-butylperoxy) 2,5-dimethyl-3-hexyne | Luperox 130XL45 | 131 |
| 1,1-Di(t-butylperoxy)-3,3,5-trimethylcyclohexane | Luperox ® 231 | 96 |
| Ethyl 3,3-di-(t-butylperoxy)butyrate | Luperox 233M75 | 114 |
| t-amyl peroxy 2-ethylhexanoate | Luperox 575 | 75 |
| Polyether poly-t-butylperoxy carbonate | Luperox JWEB50 | 100 |
| t-Butyl peroxybenzoate | Luperox P | 104 |
| 2,2'Azobis(2,4-dimethyl-valeronitrile) | V-65 | 51 |
| 2.2'-Azobisisobutyronitrile | AIBN | 65 |
| 2,2'-Azobis(2-methyl-butyronitrile) | V-59 | 87 |
| 2-Phenyllazo-2,4-dimethyl-4-methoxyvaleronitrile | V-19 | 122 |

V65, AIBN, V-59, V19 are trade designations from FUJIFILM Wako Chemicals U.S.A. Corporation (North Chesterfield, VA). All materials having the LUPEROX trade designation are from Arkema Inc. (Philadelphia PA).

Additives

Photopolymerizable compositions described herein, in some instances, further comprise one or more additives, such as one or more additives selected from the group consisting of inhibitors, stabilizing agents, sensitizers, absorption modifiers, fillers and combinations thereof.

In addition, a photopolymerizable material composition described herein can further comprise one or more sensitizers to increase the effectiveness of one or more photoinitiators that may also be present. In some embodiments, a sensitizer comprises isopropylthioxanthone (ITX) or 2-chlorothioxanthone (CTX). Other sensitizers may also be used. If used in the photopolymerizable composition, a sensitizer can be present in an amount ranging of about 0.01% by weight or about 1% by weight, based on the total weight of the photopolymerizable composition.

A photopolymerizable composition described herein optionally also comprises one or more polymerization inhibitors or stabilizing agents. A polymerization inhibitor is often included in a photopolymerizable composition to provide additional thermal stability to the composition. A stabilizing agent, in some instances, comprises one or more anti-oxidants. Any anti-oxidant not inconsistent with the objectives of the present disclosure may be used. In some embodiments, for example, suitable anti-oxidants include various aryl compounds, including butylated hydroxytoluene (BHT), which can also be used as a polymerization inhibitor in embodiments described herein. In addition to or as an alternative, a polymerization inhibitor comprises methoxyhydroquinone (MEHQ).

In some embodiments, a polymerization inhibitor, if used, is present in an amount of about 0.001-2% by weight, 0.001 to 1% by weight, or 0.01-1% by weight, based on the total weight of the photopolymerizable composition. Further, if used, a stabilizing agent is present in a photopolymerizable composition described herein in an amount of about 0.1-5% by weight, about 0.5-4% by weight, or about 1-3% by weight, based on the total weight of the photopolymerizable composition.

A photopolymerizable composition as described herein can also comprise one or more UV absorbers including dyes, optical brighteners, pigments, particulate fillers, etc., to control the penetration depth of actinic radiation. One particularly suitable UV absorber include Tinuvin 326 (2-(5-chloro-2H-benzotriazol-2-yl)-6-(1,1-dimethylethyl)-4-methylphenol, obtained from BASF Corporation, Florham Park, NJ Another particularly suitable absorption modifier is Tinopal OB, a benzoxazole, thiophenediyl)bis[5-(1,1-dimethylethyl)], also available from BASF Corporation. Another suitable UV absorber is an optical brightener comprising the following compound"

Another suitable UV absorber is an optical brightener comprising the following compound synthesized as described in detail in the Examples below.

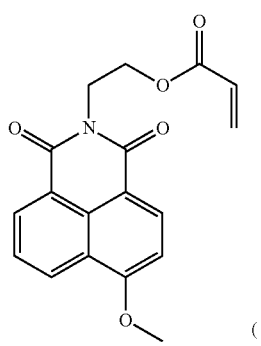 [SMILES: C=CC(=O)OCCN1C(=O)c2cccc3c(OC)ccc(c23)C1=O]

The absorption modifier, if used, can be present in an amount of about 0.001-5% by weight, about 0.01-1% by weight, about 0.1-3% by weight, or about 0.1-1% by weight, based on the total weight of the photopolymerizable composition.

Photopolymerizable compositions may include fillers, including nano-scale fillers. Examples of suitable fillers are naturally occurring or synthetic materials including, but not limited to: silica ($SiO_2$ (e.g., quartz)); alumina ($Al_2O_3$), zirconia, nitrides (e.g., silicon nitride); glasses and ceramic fillers derived from, for example, Zr, Sr, Ce, Sb, Sn, Ba, Zn, and Al; feldspar; borosilicate glass; kaolin (china clay); talc; zirconia; titania; and submicron silica particles (e.g., pyrogenic silicas such as those available under the trade designations AEROSIL, including "OX 50," "130," "150" and "200" silicas from Degussa Corp., Akron, OH and CAB-O-SIL M5 and TS-720 silica from Cabot Corp., Tuscola, IL). Organic fillers made from polymeric materials are also possible, such as those disclosed in International Publication No. WO09/045752 (Kalgutkar et al.).

In certain embodiments, the filler comprises surface modified nanoparticles. Generally, "surface modified nanoparticles" comprise surface treatment agents attached to the surface of a core. In some embodiments, the core is substantially spherical. In some embodiments, the core is at least partially or substantially crystalline. In some embodiments, the particles are substantially non-agglomerated. In some embodiments, the particles are substantially non-aggregated in contrast to, for example, fumed or pyrogenic silica. Generally, surface treatment agents for silica nanoparticles are organic species having a first functional group capable of covalently chemically attaching to the surface of a nanoparticle, wherein the attached surface treatment agent alters one or more properties of the nanoparticle. In some embodiments, surface treatment agents have no more than three functional groups for attaching to the core. In some embodiments, the surface treatment agents have a low molecular weight, e.g., a weight average molecular weight less than 1000 gm/mole.

In some embodiments, the surface-modified nanoparticles are reactive; that is, at least one of the surface treatment agents used to surface modify the nanoparticles of the present disclosure may include a second functional group capable of reacting with one or more of the urethane component and/or one or more of the reactive diluent(s) of the photopolymerizable composition. For purposes of clarity, even when the nanoparticles are reactive, they are not considered to be constituents of the resin component of the photopolymerizable composition. Surface treatment agents often include more than one first functional group capable of attaching to the surface of a nanoparticle. For example, alkoxy groups are common first functional groups that are capable of reacting with free silanol groups on the surface of a silica nanoparticle forming a covalent bond between the surface treatment agent and the silica surface. Examples of surface treatment agents having multiple alkoxy groups include trialkoxy alkylsilanes (e.g., 3-(trimethoxysilyl)propyl methacrylate) and trialkoxy arylsilanes (e.g., trimethoxy phenyl silane).

In some embodiments, the compositions further comprise inorganic nanoparticles, such as silica. In some embodiments, the average particle size is typically at least 5 or 10 nm and no greater than 100, 75, or 50 nm. At concentrations of 25 wt. % or greater, the composition typically exhibits i sufficient elongation. Hence, the concentration of (e.g. silica) inorganic nanoparticles is typically less than 25, 24, 23, 22, 21, 20, 19, 18, 17, 16, 15, 14, 13, 12, or 10 wt. % based on the total weight of the polymerizable composition. In some embodiments, the composition comprises at least 1, 2, 3, 4, or 5 wt. % (e.g. silica) inorganic nanoparticles based on the total weight of the polymerizable composition.

The compositions may further contain fibrous reinforcement and colorants such as dyes, pigments, and pigment dyes. Examples of suitable fibrous reinforcement include PGA microfibrils, collagen microfibrils, and others as described in U.S. Pat. No. 6,183,593 (Narang et al.). Examples of suitable colorants as described in U.S. Pat. No. 5,981,621 (Clark et al.) include 1-hydroxy-4-[4-methylphenylamino]-9,10-anthracenedione (FD&C violet No. 2); disodium salt of 6-hydroxy-5-[(4-sulfophenyl)oxo]-2-naphthalenesulfonic acid (FD&C Yellow No. 6); 9-(o-carboxyphenyl)-6-hydroxy-2,4,5,7-tetraiodo-3H-xanthen-3-one, disodium salt, monohydrate (FD&C Red No. 3); and the like.

Discontinuous fibers are also suitable fillers, such as fibers comprising carbon, ceramic, glass, or combinations thereof. Suitable discontinuous fibers can have a variety of compositions, such as ceramic fibers. The ceramic fibers can be produced in continuous lengths, which are chopped or sheared to provide the discontinuous ceramic fibers. The ceramic fibers can be produced from a variety of commercially available ceramic filaments. Examples of filaments useful in forming the ceramic fibers include the ceramic oxide fibers sold under the trademark NEXTEL (3M Company, St. Paul, MN). NEXTEL is a continuous filament ceramic oxide fiber having low elongation and shrinkage at operating temperatures, and offers good chemical resistance, low thermal conductivity, thermal shock resistance, and low porosity. Specific examples of NEXTEL fibers include NEXTEL 312, NEXTEL 440, NEXTEL 550, NEXTEL 610 and NEXTEL 720. NEXTEL 312 and NEXTEL 440 are refractory aluminoborosilicate that includes $Al_2O_3$, $SiO_2$ and $B_2O_3$. NEXTEL 550 and NEXTEL 720 are aluminosilica and NEXTEL 610 is alumina. During manufacture, the NEXTEL filaments are coated with organic sizings or finishes which serves as aids in textile processing. Sizing can include the use of starch, oil, wax or other organic ingredients applied to the filament strand to protect and aid handling. The sizing can be removed from the ceramic filaments by heat cleaning the filaments or ceramic fibers as a temperature of 700° C. for one to four hours.

The ceramic fibers can be cut, milled, or chopped so as to provide relatively uniform lengths, which can be accomplished by cutting continuous filaments of the ceramic material in a mechanical shearing operation or laser cutting operation, among other cutting operations. Given the highly controlled nature of certain cutting operations, the size distribution of the ceramic fibers is very narrow and allow to control the composite property. The length of the ceramic fiber can be determined, for instance, using an optical microscope (Olympus MX61, Tokyo, Japan) fit with a CCD Camera (Olympus DP72, Tokyo, Japan) and analytic software (Olympus Stream Essentials, Tokyo, Japan). Samples may be prepared by spreading representative samplings of the ceramic fiber on a glass slide and measuring the lengths of at least 200 ceramic fibers at 10× magnification.

Suitable fibers include for instance ceramic fibers available under the trade name NEXTEL (available from 3M Company, St. Paul, MN), such as NEXTEL 312, 440, 610 and 720. One presently preferred ceramic fiber comprises polycrystalline α-$Al_2O_3$. Suitable alumina fibers are described, for example, in U.S. Pat. No. 4,954,462 (Wood et al.) and U.S. Pat. No. 5,185,299 (Wood et al.). Exemplary alpha alumina fibers are marketed under the trade designation NEXTEL 610 (3M Company, St. Paul, MN). In some embodiments, the alumina fibers are polycrystalline alpha alumina fibers and comprise, on a theoretical oxide basis, greater than 99 percent by weight $Al_2O_3$ and 0.2-0.5 percent by weight $SiO_2$, based on the total weight of the alumina fibers. In other embodiments, some desirable polycrystalline, alpha alumina fibers comprise alpha alumina having an average grain size of less than one micrometer (or even, in some embodiments, less than 0.5 micrometer). In some embodiments, polycrystalline, alpha alumina fibers have an average tensile strength of at least 1.6 GPa (in some embodiments, at least 2.1 GPa, or even, at least 2.8 GPa). Suitable aluminosilicate fibers are described, for example, in U.S. Pat. No. 4,047,965 (Karst et al). Exemplary aluminosilicate fibers are marketed under the trade designations NEXTEL 440, and NEXTEL 720, by 3M Company (St. Paul, MN). Aluminoborosilicate fibers are described, for example, in U.S. Pat. No. 3,795,524 (Sowman). Exemplary aluminoborosilicate fibers are marketed under the trade designation NEXTEL 312 by 3M Company. Boron nitride fibers can be made, for example, as described in U.S. Pat. No. 3,429,722 (Economy) and U.S. Pat. No. 5,780,154 (Okano et al.).

Ceramic fibers can also be formed from other suitable ceramic oxide filaments. Examples of such ceramic oxide filaments include those available from Central Glass Fiber Co., Ltd. (e.g., EFH75-01, EFH150-31). Also preferred are aluminoborosilicate glass fibers, which contain less than about 2% alkali or are substantially free of alkali (i.e., "E-glass" fibers). E-glass fibers are available from numerous commercial suppliers.

Examples of useful pigments include, without limitation: white pigments, such as titanium oxide, zinc phosphate, zinc sulfide, zinc oxide and lithopone; red and red-orange pigments, such as iron oxide (maroon, red, light red), iron/chrome oxide, cadmium sulfoselenide and cadmium mercury (maroon, red, orange); ultramarine (blue, pink and violet), chrome-tin (pink) manganese (violet), cobalt (violet); orange, yellow and buff pigments such as barium titanate, cadmium sulfide (yellow), chrome (orange, yellow), molybdate (orange), zinc chromate (yellow), nickel titanate (yellow), iron oxide (yellow), nickel tungsten titanium, zinc ferrite and chrome titanate; brown pigments such as iron oxide (buff, brown), manganese/antimony/titanium oxide, manganese titanate, natural siennas (umbers), titanium tungsten manganese; blue-green pigments, such as chrome aluminate (blue), chrome cobalt-alumina (turquoise), iron blue (blue), manganese (blue), chrome and chrome oxide (green) and titanium green; as well as black pigments, such as iron oxide black and carbon black. Combinations of pigments are generally used to achieve the desired color tone in the cured composition.

The use of florescent dyes and pigments can also be beneficial in enabling the printed composition to be viewed under black-light. A particularly useful hydrocarbon soluble fluorescing dye is 2,5-bis(5-tert-butyl-2-benzoxazolyl) 1 thiophene. Fluorescing dyes, such as rhodamine, may also be bound to cationic polymers and incorporated as part of the resin.

If desired, the compositions of the disclosure may contain other additives such as indicators, accelerators, surfactants, wetting agents, antioxidants, tartaric acid, chelating agents, buffering agents, and other similar ingredients that will be apparent to those skilled in the art. Additionally, medicaments or other therapeutic substances can be optionally added to the photopolymerizable compositions. Examples include, but are not limited to, fluoride sources, whitening agents, anticaries agents (e.g., xylitol), remineralizing agents (e.g., calcium phosphate compounds and other calcium sources and phosphate sources), enzymes, breath fresheners, anesthetics, clotting agents, acid neutralizers, chemotherapeutic agents, immune response modifiers, thixotropes, polyols, anti-inflammatory agents, antimicrobial agents, antifungal agents, agents for treating xerostomia, desensitizers, and the like, of the type often used in dental compositions.

Combinations of any of the above additives may also be employed. The selection and amount of any one such additive can be selected by one of skill in the art to accomplish the desired result without undue experimentation.

Photopolymerizable compositions herein can also exhibit a variety of desirable properties, non-cured, cured, and as post-cured articles. A photopolymerizable composition, when non-cured, has a viscosity profile consistent with the requirements and parameters of one or more additive manufacturing devices (e.g., 3D printing systems). In some instances, a photopolymerizable composition described herein when non-cured exhibits a dynamic viscosity of about 0.1-1,000 Pa·s, about 0.1-100 Pa·s, or about 1-10 Pa·s, using a TA Instruments AR-G2 magnetic bearing rheometer using a 40 mm cone and plate measuring system at 40 degrees Celsius and at a shear rate of 0.1 l/s, when measured according to ASTM D4287, as set forth in the Example Test Method below. In some cases, a photopolymerizable composition described herein when non-cured exhibits a dynamic viscosity of less than about 10 Pa·s, at 25, 30, 35 or 40° C. when measured according to modified ASTM D4287.

Articles and Methods

In another aspect, the present disclosure provides an (e.g. orthodontic) article. The article comprises a reaction product of the photopolymerizable composition described herein.

In many embodiments, the photopolymerizable composition of the article is vat polymerized, as discussed in detail below.

The shape of the article is not limited, and may comprise a film or a shaped integral article. For instance, a film may readily be prepared by casting the photopolymerizable composition according to the first aspect, then subjecting the cast composition to actinic radiation to polymerize the photopolymerizable composition. In many embodiments, the article comprises a shaped integral article, in which more than one variation in dimension is provided by a single integral article. For example, the article can comprise one or more channels, one or more undercuts, one or more perforations, or combinations thereof. Such features are typically not possible to provide in an integral article using conventional molding methods. In some embodiments, the article comprises a plurality of layers. In select embodiments, the article comprises an orthodontic article. Orthodontic articles are described in further detail below.

In another aspect, the present disclosure provides a method of making an (e.g. orthodontic) article. The method comprises:
(a) providing a photopolymerizable composition, as described herein;
(b) selectively curing the photopolymerizable composition to form an article; and
(c) optionally curing unpolymerized urethane component and/or reactive diluent remaining after step (b).

In many embodiments, the photopolymerizable composition is cured using actinic radiation comprising UV radiation, e-beam radiation, visible radiation, or a combination thereof. Moreover, the method optionally further comprises post curing the article using actinic radiation or heat.

In additive manufacturing methods, the method further comprises (d) repeating steps (a) and (b) to form multiple layers and create the article comprising a three-dimensional structure prior to step (c). In certain embodiments, the method comprises vat polymerization of the photopolymerizable composition. When vat polymerization is employed, the radiation may be directed through a wall of a container (e.g., a vat) holding the photopolymerizable composition, such as a side wall or a bottom wall (e.g., floor).

In some embodiments, the method further comprises (e) subjecting the article to heating in an oven, for instance a vacuum oven. Typically, the oven is set at a temperature of 60° C. or higher. A stepwise heating process is optional, such as heating at 60° C., then at 80° C., and then at 100° C. Subjecting the article to heating is often performed to drive off unreacted reactive diluent remaining in the article.

A photopolymerizable composition described herein in a cured state, in some embodiments, can exhibit one or more desired properties. A photopolymerizable composition in a "cured" state can comprise a photopolymerizable composition that includes a polymerizable component that has been at least partially polymerized and/or crosslinked. For instance, in some instances, a cured article is at least about 10% polymerized or crosslinked or at least about 30% polymerized or crosslinked. In some cases, a cured photopolymerizable composition is at least about 50%, at least about 70%, at least about 80%, or at least about 90% polymerized or crosslinked. A cured photopolymerizable composition can also be between about 10% and about 99% polymerized or crosslinked.

The conformability and durability of a cured article made from the photopolymerizable compositions of the present disclosure can be determined in part by standard tensile, modulus, and/or elongation testing. The photopolymerizable compositions can typically be characterized by at least one of the following parameters after hardening. In some embodiments, the elongation is at least 18 or 20%. Advantageously, the elongation at break is typically 25% or greater, 27% or greater, 30% or greater, 32% or greater, 35% or greater, 40% or greater, 45% or greater, 50% or greater, 55% or greater, or 60% or greater; and 200% or less, 100% or less, 90% or less, 80% or less, or 70% or less. The elongation at break of the cured article can range up to 200, 300, 400, or 500%. In some embodiments, the elongation at break is at least 30% and no greater than 100%.

The ultimate tensile strength is typically 15 MegaPascals (MPa) or greater, 20 MPA or greater, 25 MPa or greater, or 30 MPa or greater, and is typically 80 MPa or less, each as determined according to ASTM D638-10. While the urethane component has the greatest effect on the elongation at break of an article, other components of the photopolymerizable composition also impact the elongation at break, e.g., the length of a linear chain or branch of a reactive diluent tends to be positively correlated to the elongation at break of the final article.

The tensile modulus is typically 250 MPa or greater, 500 MPa or greater, 750 MPa or greater, or 1,000 MPa or greater, as determined according to ASTM D638-10. Such elongation properties can be measured, for example, by the methods outlined in ASTM D638-10, using test specimen Type V. The mechanical properties above are particularly well suited for articles that require resiliency and flexibility, along with adequate wear strength and low hygroscopicity.

In some embodiments, the cured (e.g. cast or 3D printed) photopolymerizable composition described herein have the elongation properties described above after conditioning (i.e., soaking) of a sample of the material of the orthodontic article in phosphate-buffered saline having a pH of 7.4, for 24 hours at a temperature of 37° C. ("PBS Conditioning").

In some embodiments, the cured (e.g. cast or 3D printed) photopolymerizable composition described herein exhibits a tensile strength at yield of 14 MPa or greater as determined, as determined according to ASTM-D638-14, using test specimen V, after PBS Conditioning. High tensile strength contributes to the article having sufficient strength to be resilient during use in a patient's mouth. Preferably, an article exhibits a tensile strength at yield of 15 MPa or greater, 17 MPa or greater, 20 MPa or greater, 25 MPa or greater, 30 MPa or greater, 35 MPa or greater, 40 MPa or greater, 45 MPa or greater, 50 MPa or greater, or even 55 MPa or greater. In some embodiments, the tensile strength at yield is no greater than 75, 70, 60 or 65 MPa.

Photopolymerizable compositions described herein can be mixed by known techniques. In some embodiments, for instance, a method for the preparation of a photopolymerizable composition described herein comprises the steps of mixing all or substantially all of the components of the photopolymerizable composition, heating the mixture, and optionally filtering the heated mixture. Softening the mixture, in some embodiments, is carried out at a temperature of about 50° C. or in a range from about 50° C. to about 85° C. In some embodiments, a photopolymerizable composition described herein is produced by placing all or substantially all components of the composition in a reaction vessel and heating the resulting mixture to a temperature ranging from about 50° C. to about 85° C. with stirring. The heating and stirring are continued until the mixture attains a substantially homogenized state.

Fabricating an Article

Once prepared as set forth above, the photopolymerizable compositions of the present disclosure may be used in myriad additive manufacturing processes to create a variety of articles, including casting a film as noted above. A generalized method 100 for creating three-dimensional articles is illustrated in FIG. 1. Each step in the method will be discussed in greater detail below. First, in Step 110 the desired photopolymerizable composition (e.g., comprising at least one urethane component, at least one monofunctional reactive diluent, and an initiator) is provided and introduced into a reservoir, cartridge, or other suitable container for use by or in an additive manufacturing device. The additive manufacturing device selectively cures the photopolymerizable composition according to a set of computerized design instructions in Step 120. In Step 130, Step 110 and/or Step 120 is repeated to form multiple layers to create the article comprising a three-dimensional structure (e.g., an orthodontic aligner). Optionally uncured photopolymerizable composition is removed from the article in Step 140, further optionally, the article is subjected to additional curing to polymerize remaining uncured photopolymerizable components in the article in Step 150, and even further optionally, the article is subjected to heat to drive off remaining unreacted reactive diluent in Step 160.

Methods of printing a three-dimensional article or object described herein can include forming the article from a plurality of layers of a photopolymerizable composition described herein in a layer-by-layer manner. Further, the layers of a build material composition can be deposited according to an image of the three-dimensional article in a computer readable format. In some or all embodiments, the photopolymerizable composition is deposited according to preselected computer aided design (CAD) parameters.

Additionally, it is to be understood that methods of manufacturing a 3D article described herein can include so-called "stereolithography/vat polymerization" 3D printing methods. Other techniques for three-dimensional manufacturing are known, and may be suitably adapted to use in the applications described herein. More generally, three-dimensional fabrication techniques continue to become available. All such techniques may be adapted to use with photopolymerizable compositions described herein, provided they offer compatible fabrication viscosities and resolutions for the specified article properties. Fabrication may be performed using any of the fabrication technologies described herein, either alone or in various combinations, using data representing a three-dimensional object, which may be reformatted or otherwise adapted as necessary for a particular printing or other fabrication technology.

It is entirely possible to form a 3D article from a photopolymerizable composition described herein using vat polymerization (e.g., stereolithography). For example, in some cases, a method of printing a 3D article comprises retaining a photopolymerizable composition described herein in a fluid state in a container and selectively applying energy to the photopolymerizable composition in the container to solidify at least a portion of a fluid layer of the photopolymerizable composition, thereby forming a hardened layer that defines a cross-section of the 3D article. Additionally, a method described herein can further comprise raising or lowering the hardened layer of photopolymerizable composition to provide a new or second fluid layer of unhardened photopolymerizable composition at the surface of the fluid in the container, followed by again selectively applying energy to the photopolymerizable composition in the container to solidify at least a portion of the new or second fluid layer of the photopolymerizable composition to form a second solidified layer that defines a second cross-section of the 3D article. Further, the first and second cross-sections of the 3D article can be bonded or adhered to one another in the z-direction (or build direction corresponding to the direction of raising or lowering recited above) by the application of the energy for solidifying the photopolymerizable composition. Moreover, selectively applying energy to the photopolymerizable composition in the container can comprise applying actinic radiation, such as UV radiation, visible radiation, or e-beam radiation, having a sufficient energy to cure the photopolymerizable composition. A method described herein can also comprise planarizing a new layer of fluid photopolymerizable composition provided by raising or lowering an elevator platform. Such planarization can be carried out, in some cases, by utilizing a wiper or roller or a recoater bead. Planarization corrects the thickness of one or more layers prior to curing the material by evening the dispensed material to remove excess material and create a uniformly smooth exposed or flat up-facing surface on the support platform of the printer.

It is further to be understood that the foregoing process can be repeated a selected number of times to provide the 3D article. For example, in some cases, this process can be repeated "n" number of times. Further, it is to be understood that one or more steps of a method described herein, such as a step of selectively applying energy to a layer of photopolymerizable composition, can be carried out according to an image of the 3D article in a computer-readable format. Suitable stereolithography printers include the Viper Pro SLA, available from 3D Systems, Rock Hill, SC and the Asiga Pico Plus39, available from Asiga USA, Anaheim Hills, CA.

Figure 2:
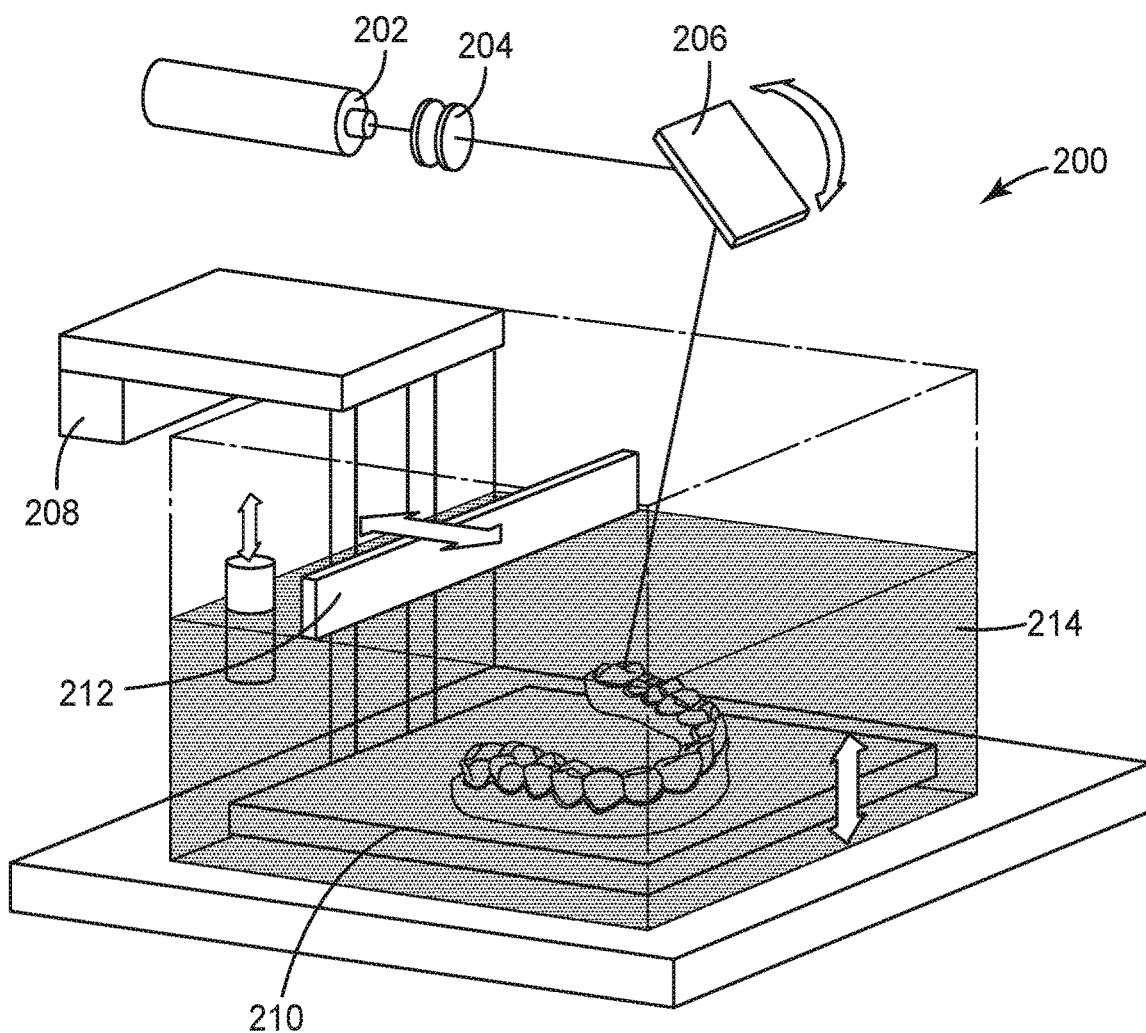
FIG. 2 is a generalized schematic of a stereolithography apparatus.

FIG. 2 shows an exemplary stereolithography apparatus ("SLA") that may be used with the photopolymerizable compositions and methods described herein. In general, the SLA 200 may include a laser 202, optics 204, a steering lens 206, an elevator 208, a platform 210, and a straight edge 212, within a vat 214 filled with the photopolymerizable composition. In operation, the laser 202 is steered across a surface of the photopolymerizable composition to cure a cross-section of the photopolymerizable composition, after which the elevator 208 slightly lowers the platform 210 and another cross section is cured. The straight edge 212 may sweep the surface of the cured composition between layers to smooth and normalize the surface prior to addition of a new layer. In other embodiments, the vat 214 may be slowly filled with liquid resin while an article is drawn, layer by layer, onto the top surface of the photopolymerizable composition.

A related technology, vat polymerization with Digital Light Processing ("DLP"), also employs a container of curable polymer (e.g., photopolymerizable composition). However, in a DLP based system, a two-dimensional cross section is projected onto the curable material to cure the desired section of an entire plane transverse to the projected beam at one time. All such curable polymer systems as may be adapted to use with the photopolymerizable compositions described herein are intended to fall within the scope of the term "vat polymerization system" as used herein. In certain embodiments, an apparatus adapted to be used in a continuous mode may be employed, such as an apparatus commercially available from Carbon 3D, Inc. (Redwood City, CA), for instance as described in U.S. Pat. Nos. 9,205,601 and 9,360,757 (both to DeSimone et al.).

Figure 5:
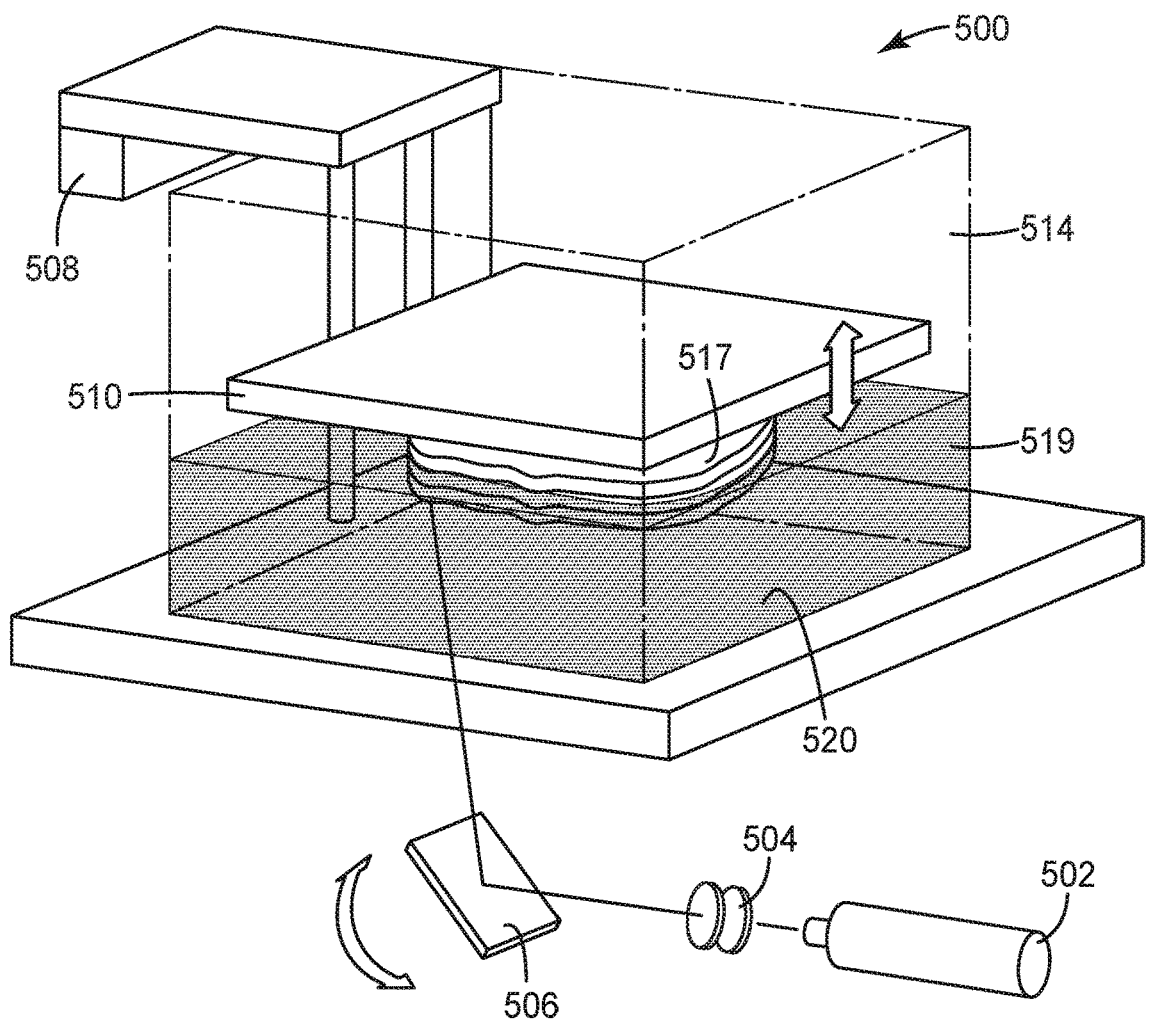
FIG. 5 is a generalized schematic of an apparatus in which radiation is directed through a container.

Referring to FIG. 5, a general schematic is provided of another SLA apparatus that may be used with photopolymerizable compositions and methods described herein. In general, the apparatus 500 may include a laser 502, optics 504, a steering lens 506, an elevator 508, and a platform 510, within a vat 514 filled with the photopolymerizable composition 519. In operation, the laser 502 is steered through a wall 520 (e.g., the floor) of the vat 514 and into the photopolymerizable composition to cure a cross-section of the photopolymerizable composition 519 to form an article 517, after which the elevator 508 slightly raises the platform 510 and another cross section is cured.

More generally, the photopolymerizable composition is typically cured using actinic radiation, such as UV radiation, e-beam radiation, visible radiation, or any combination thereof. The skilled practitioner can select a suitable radiation source and range of wavelengths for a particular application without undue experimentation.

After the 3D article has been formed, it is typically removed from the additive manufacturing apparatus and rinsed, (e.g., an ultrasonic, or bubbling, or spray rinse in a solvent, which would dissolve a portion of the uncured photopolymerizable composition but not the cured, solid state article (e.g., green body). Any other conventional method for cleaning the article and removing uncured material at the article surface may also be utilized. At this stage, the three-dimensional article typically has sufficient green strength for handling in the remaining optional steps of method 100.

It is expected in certain embodiments of the present disclosure that the formed article obtained in Step 120 will shrink (i.e., reduce in volume) such that the dimensions of the article after (optional) Step 150 will be smaller than expected. For example, a cured article may shrink less than 5% in volume, less than 4%, less than 3%, less than 2%, or even less than 1% in volume, which is contrast to other compositions that provide articles that shrink about 6-8% in volume upon optional postcuring. The amount of volume percent shrinkage will not typically result in a significant distortion in the shape of the final object. It is particularly contemplated, therefore, that dimensions in the digital representation of the eventual cured article may be scaled according to a global scale factor to compensate for this shrinkage. For example, in some embodiments, at least a portion of the digital article representation can be at least 101% of the desired size of the printed appliance, in some embodiments at least 102%, in some embodiments at least 104%, in some embodiments, at least 105%, and in some embodiments, at least 110%.

A global scale factor may be calculated for any given photopolymerizable composition formulation by creating a calibration part according to Steps 110 and 120 above. The dimensions of the calibration article can be measured prior to postcuring.

In general, the three-dimensional article formed by initial additive manufacturing in Step 120, as discussed above, is not fully cured, by which is meant that not all of the photopolymerizable material in the composition has polymerized even after rinsing. Some uncured photopolymerizable material is typically removed from the surface of the printed article during a cleaning process (e.g., optional Step 140). The article surface, as well as the bulk article itself, typically still retains uncured photopolymerizable material, suggesting further cure. Removing residual uncured photopolymerizable composition is particularly useful when the article is going to subsequently be postcured, to minimize uncured residual photopolymerizable composition from undesirably curing directly onto the article.

Further curing can be accomplished by further irradiating with actinic radiation, heating, or both. Exposure to actinic radiation can be accomplished with any convenient radiation source, generally UV radiation, visible radiation, and/or e-beam radiation, for a time ranging from about 10 to over 60 minutes. Heating is generally carried out at a temperature in the range of about 75-150° C., for a time ranging from about 10 to over 60 minutes in an inert atmosphere. So called post cure ovens, which combine UV radiation and thermal energy, are particularly well suited for use in the postcure process of Step 150. In general, postcuring improves the mechanical properties and stability of the three-dimensional article relative to the same three-dimensional article that is not postcured. In certain embodiments, the article is also subjected to heat or actinic radiation to drive off remaining unreacted components (e.g. reactive diluent) in Step 160.

The following describes general methods for creating a clear tray aligner as printed appliance 300. However, other dental and orthodontic articles can be created using similar techniques and the photopolymerizable compositions of the present disclosure. Representative examples include, but are not limited to, the removable appliances having occlusal windows described in International Application Publication No. WO2016/109660 (Raby et al.), the removable appliances with a palatal plate described in US Publication No. 2014/0356799 (Cinader et al); and the resilient polymeric arch members described in International Application Nos. WO2016/148960 and WO2016/149007 (Oda et al.); as well as US Publication No. 2008/0248442 (Cinader et al.). Moreover, the photopolymerizable compositions can be used in the creation of indirect bonding trays, such as those described in International Publication No. WO2015/094842 (Paehl et al.) and US Publication No. 2011/0091832 (Kim, et al.) and other dental articles, including but not limited to crowns, bridges, veneers, inlays, onlays, fillings, and prostheses (e.g., partial or full dentures). Other orthodontic appliances and devices include, but not limited to, orthodontic brackets, buccal tubes, lingual retainers, orthodontic bands, class II and class III correctors, sleep apnea devices, bite openers, buttons, cleats, and other attachment devices.

In certain embodiments, the (e.g., orthodontic) article advantageously has a certain equilibrium modulus even after stress relaxation provides a particular maximum amount of stress relaxation. The equilibrium modulus after stress relaxation can be measured by monitoring the stress resulting from a steady strain over time at a specific temperature (e.g., 37° C.) and a specific relative humidity (e.g., 100% relative humidity). In at least certain embodiments, the equilibrium modulus is 100 MPa or greater after 24 hours at 2% strain under 100% relative humidity and 37° C.

Alternatively, the photopolymerizable compositions can be used in other industries, such as aerospace, animation and entertainment, architecture and art, automotive, consumer goods and packaging, education, electronics, hearing aids, sporting goods, jewelry, medical, manufacturing, etc.

Fabricating an Orthodontic Appliance with the Photopolymerizable Compositions

Figure 3:
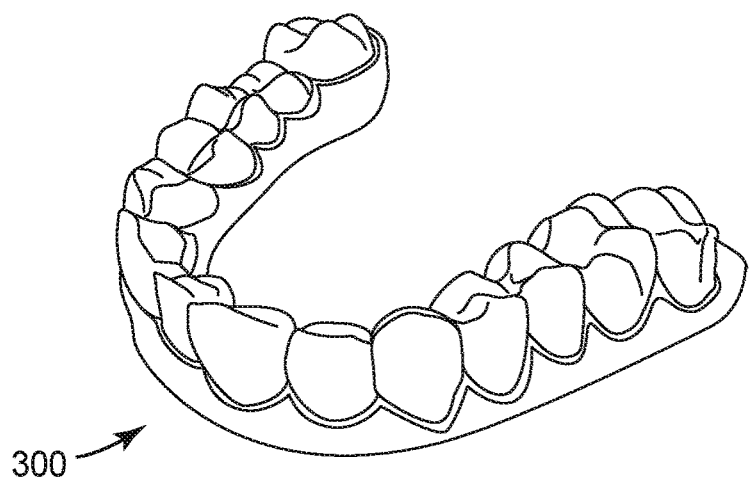
FIG. 3 is an isometric view of a printed clear tray aligner, according to one embodiment of the present disclosure.

One particularly interesting implementation of an article is generally depicted in FIG. 3. The additive manufactured article 300 is a clear tray aligner and is removably positionable over some or all of a patient's teeth. In some embodiments, the appliance 300 is one of a plurality of incremental adjustment appliances. The appliance 300 may comprise a shell having an inner cavity. The inner cavity is shaped to receive and resiliently reposition teeth from one tooth arrangement to a successive tooth arrangement. The inner cavity may include a plurality of receptacles, each of which is adapted to connect to and receive a respective tooth of the patient's dental arch. The receptacles are spaced apart from each other along the length of the cavity, although adjoining regions of adjacent receptacles can be in communication with each other. In some embodiments, the shell fits over all teeth present in the upper jaw or lower jaw. Typically, only certain one(s) of the teeth will be repositioned while others of the teeth will provide a base or anchor region for holding the dental appliance in place as it applies the resilient repositioning force against the tooth or teeth to be treated.

In order to facilitate positioning of the teeth of the patient, at least one of receptacles may be misaligned as compared to the corresponding tooth of the patient. In this manner, the appliance 300 may be configured to apply rotational and/or translational forces to the corresponding tooth of the patient when the appliance 300 is worn by the patient. In some particular examples, the appliance 300 may be configured to provide only compressive or linear forces. In the same or different examples, the appliance 300 may be configured to apply translational forces to one or more of the teeth within receptacles.

In some embodiments, the shell of the appliance 300 fits over some or all anterior teeth present in an upper jaw or lower jaw. Typically, only certain one(s) of the teeth will be repositioned while others of the teeth will provide a base or anchor region for holding the appliance in place as it applies the resilient repositioning force against the tooth or teeth to be repositioned. An appliance 300 can accordingly be designed such that any receptacle is shaped to facilitate retention of the tooth in a particular position in order to maintain the current position of the tooth.

Figure 4:
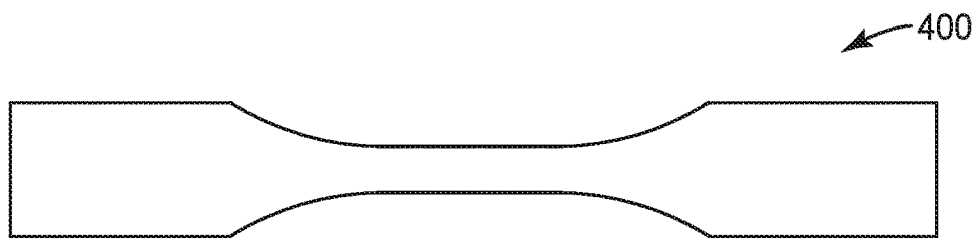
FIG. 4 is a flowchart of a process for manufacturing a printed orthodontic appliance according to the present disclosure.

A method 400 of creating an orthodontic appliance using the photopolymerizable compositions of the present disclosure can include general steps as outlined in FIG. 4. Individual aspects of the process are discussed in further detail below. The process includes generating a treatment plan for repositioning a patient's teeth. Briefly, a treatment plan can include obtaining data representing an initial arrangement of the patient's teeth (Step 410), which typically includes obtaining an impression or scan of the patient's teeth prior to the onset of treatment. The treatment plan will also include identifying a final or target arrangement of the patient's anterior and posterior teeth as desired (Step 420), as well as a plurality of planned successive or intermediary tooth arrangements for moving at least the anterior teeth along a treatment path from the initial arrangement toward the selected final or target arrangement (Step 430). One or more appliances can be virtually designed based on the treatment plan (Step 440), and image data representing the appliance designs can exported in STL format, or in any other suitable computer processable format, to an additive manufacturing device (e.g., a 3D printer system) (Step 450). An appliance can be manufactured using a photopolymerizable composition of the present disclosure retained in the additive manufacturing device (Step 460).

In some embodiments, a (e.g., non-transitory) machine-readable medium is employed in additive manufacturing of articles according to at least certain aspects of the present disclosure. Data is typically stored on the machine-readable medium. The data represents a three-dimensional model of an article, which can be accessed by at least one computer processor interfacing with additive manufacturing equipment (e.g., a 3D printer, a manufacturing device, etc.). The data is used to cause the additive manufacturing equipment to create an article comprising a reaction product of a photopolymerizable composition, the photopolymerizable composition comprising a blend of: (a) 30 to 70 wt. %, inclusive, of at least one urethane component; (b) 25 to 70 wt. %, inclusive, of at least one monofunctional reactive diluent, wherein the at least one monofunctional reactive diluent comprises at least one monofunctional reactive diluent having a $T_g$ of up to but not including 25 degrees Celsius; (c) optionally at least one difunctional reactive diluent in an amount of 1 to 30 wt. %, inclusive, if present, based on the total weight of the photopolymerizable composition; (d) 0.1 to 5 wt. %, inclusive, of at least one initiator; and (e) an optional inhibitor in an amount of 0.001 to 1 wt. %, inclusive, if present, based on the total weight of the photopolymerizable composition. In certain embodiments, the article is an orthodontic article. Preferably, the article has an elongation at break of 25% or greater.

Data representing an article may be generated using computer modeling such as computer aided design (CAD) data. Image data representing the (e.g., polymeric) article design can be exported in STL format, or in any other suitable computer processable format, to the additive manufacturing equipment. Scanning methods to scan a three-dimensional object may also be employed to create the data representing the article. One exemplary technique for acquiring the data is digital scanning. Any other suitable scanning technique may be used for scanning an article, including X-ray radiography, laser scanning, computed tomography (CT), magnetic resonance imaging (MRI), and ultrasound imaging. Other possible scanning methods are described, e.g., in U.S. Patent Application Publication No. 2007/0031791 (Cinader, Jr., et al.). The initial digital data set, which may include both raw data from scanning operations and data representing articles derived from the raw data, can be processed to segment an article design from any surrounding structures (e.g., a support for the article). In embodiments wherein the article is an orthodontic article, scanning techniques may include, for example, scanning a patient's mouth to customize an orthodontic article for the patient.

Figure 10:
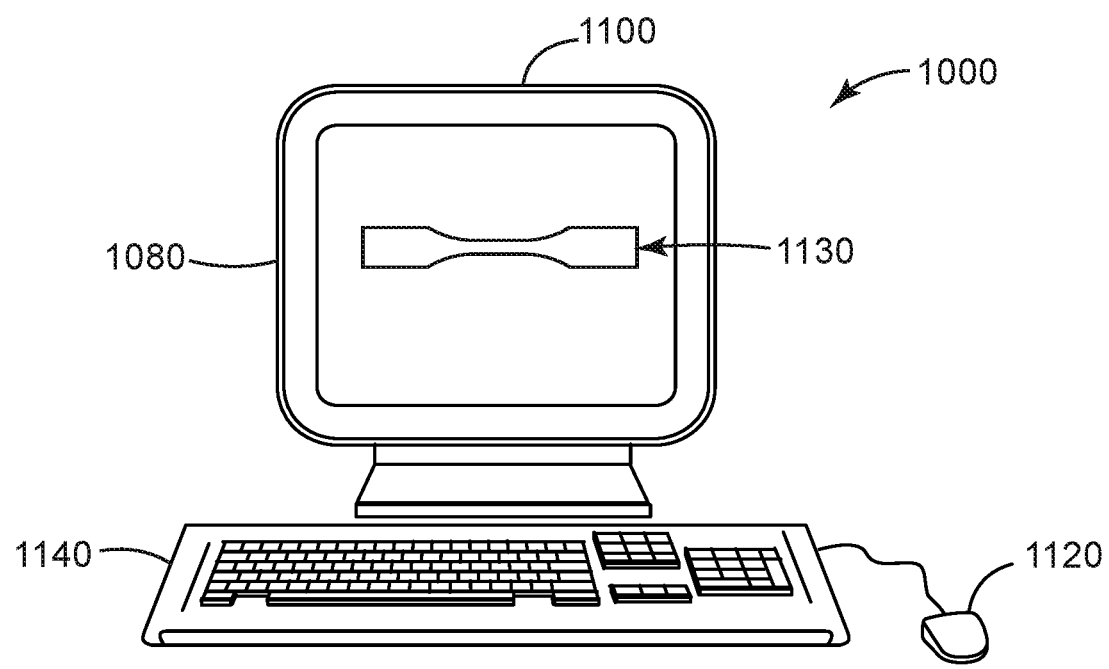
FIG. 10 is a schematic front view of an exemplary computing device 1000.

Often, machine-readable media are provided as part of a computing device. The computing device may have one or more processors, volatile memory (RAM), a device for reading machine-readable media, and input/output devices, such as a display, a keyboard, and a pointing device. Further, a computing device may also include other software, firmware, or combinations thereof, such as an operating system and other application software. A computing device may be, for example, a workstation, a laptop, a personal digital assistant (PDA), a server, a mainframe or any other general-purpose or application-specific computing device. A computing device may read executable software instructions from a computer-readable medium (such as a hard drive, a CD-ROM, or a computer memory), or may receive instructions from another source logically connected to computer, such as another networked computer. Referring to FIG. 10, a computing device 1000 often includes an internal processor 1080, a display 1100 (e.g., a monitor), and one or more input devices such as a keyboard 1140 and a mouse 1120. In FIG. 10, an aligner 1130 is shown on the display 1100.

Figure 6:
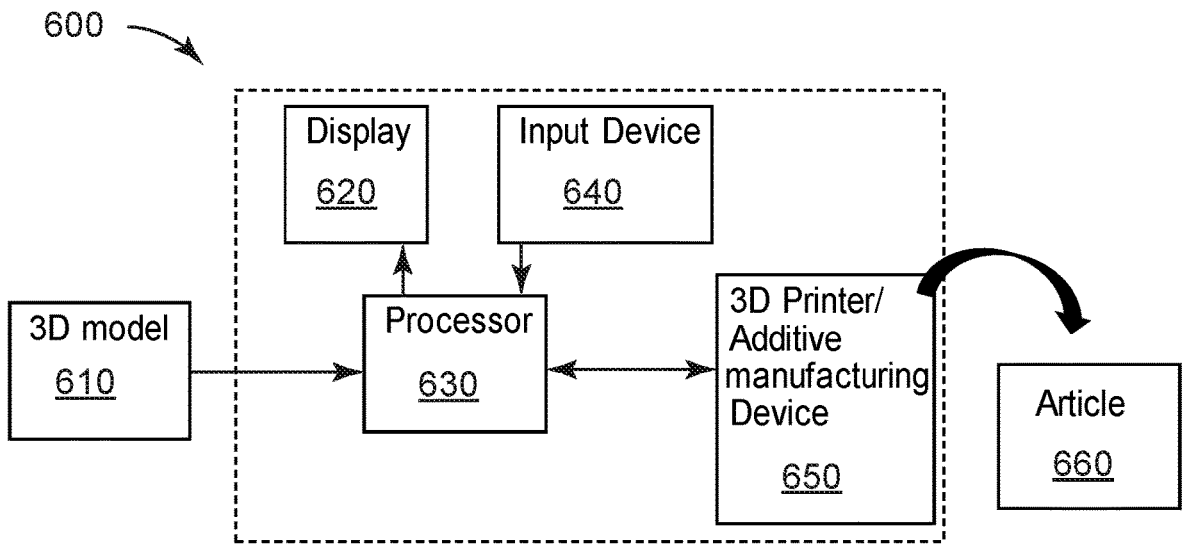
FIG. 6 is a block diagram of a generalized system 600 for additive manufacturing of an article.

Referring to FIG. 6, in certain embodiments, the present disclosure provides a system 600. The system 600 comprises a display 620 that displays a 3D model 610 of an article (e.g., an aligner 1130 as shown on the display 1100 of FIG. 10); and one or more processors 630 that, in response to the 3D model 610 selected by a user, cause a 3D printer/additive manufacturing device 650 to create a physical object of the article 660. Often, an input device 640 (e.g., keyboard and/or mouse) is employed with the display 620 and the at least one processor 630, particularly for the user to select the 3D model 610. The article 660 comprises a reaction product of a photopolymerizable composition, the photopolymerizable composition comprising a blend of: (a) 30 to 70 wt. %, inclusive, of at least one urethane component; (b) 25 to 70 wt. %, inclusive, of at least one monofunctional reactive diluent, wherein the at least one monofunctional reactive diluent comprises at least one monofunctional reactive diluent having a Tg of up to but not including 25 degrees Celsius; (c) optionally at least one difunctional reactive diluent in an amount of 1 to 30 wt. %, inclusive, if present, based on the total weight of the photopolymerizable composition; (d) 0.1 to 5 wt. %, inclusive, of at least one initiator; and (e) an optional inhibitor in an amount of 0.001 to 1 wt. %, inclusive, if present, based on the total weight of the photopolymerizable composition.

Figure 7:
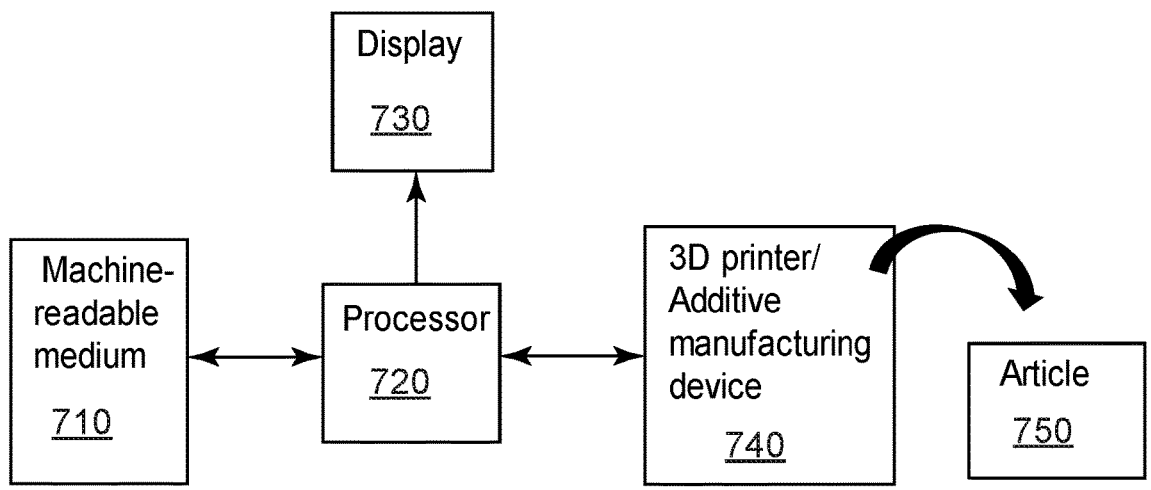
FIG. 7 is a block diagram of a generalized manufacturing process for an article.

Referring to FIG. 7, a processor 720 (or more than one processor) is in communication with each of a machine-readable medium 710 (e.g., a non-transitory medium), a 3D printer/additive manufacturing device 740, and optionally a display 730 for viewing by a user. The 3D printer/additive manufacturing device 740 is configured to make one or more articles 750 based on instructions from the processor 720 providing data representing a 3D model of the article 750 (e.g., an aligner 1130 as shown on the display 1100 of FIG. 10) from the machine-readable medium 710.

Figure 8:
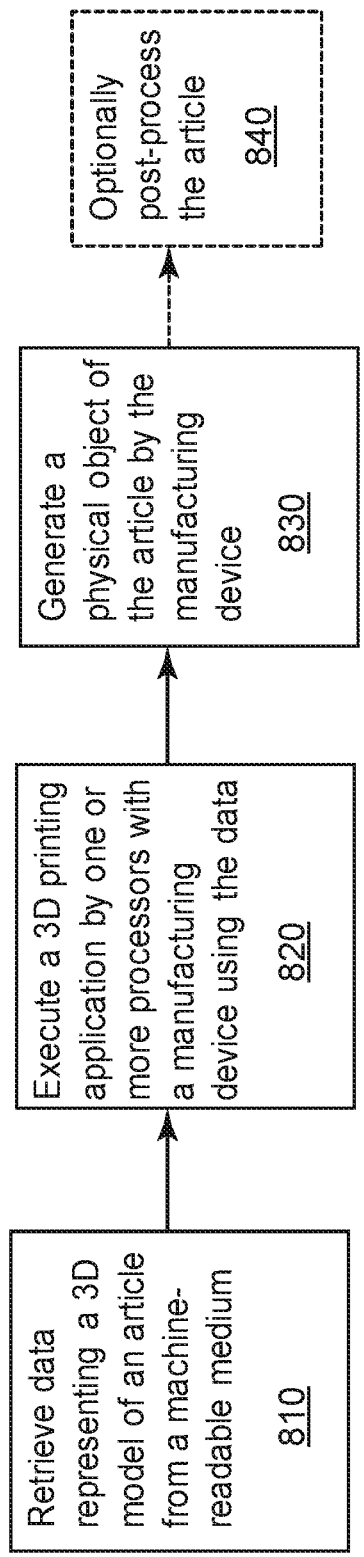
FIG. 8 is a high-level flow chart of an exemplary article manufacturing process.
Figure 9:
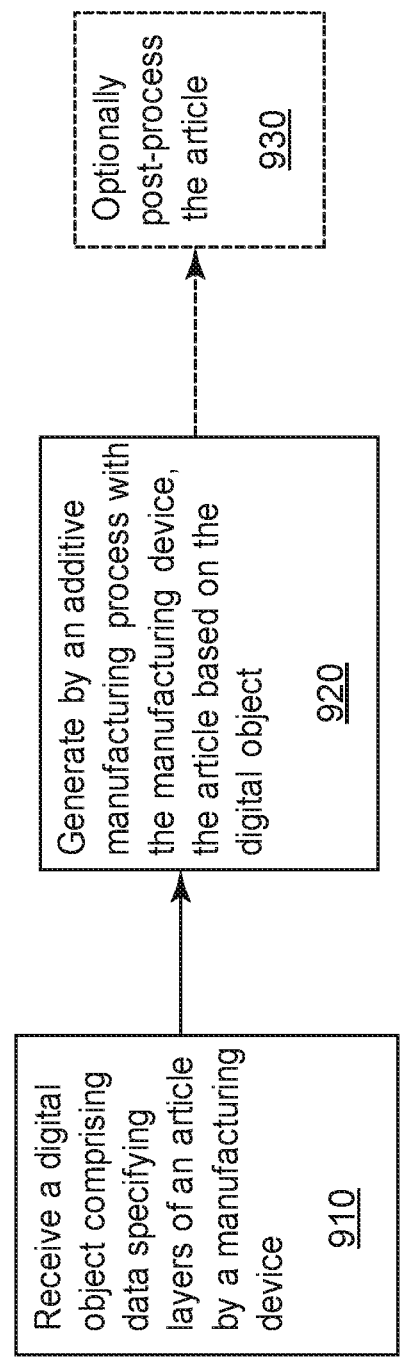
FIG. 9 is a high-level flow chart of an exemplary article additive manufacturing process.

Referring to FIG. 8, for example and without limitation, an additive manufacturing method comprises retrieving 810, from a (e.g., non-transitory) machine-readable medium, data representing a 3D model of an article according to at least one embodiment of the present disclosure. The method further includes executing 820, by one or more processors, an additive manufacturing application interfacing with a manufacturing device using the data; and generating 830, by the manufacturing device, a physical object of the article. The additive manufacturing equipment can selectively cure a photopolymerizable composition to form an article. The article comprises a reaction product of a photopolymerizable composition, the photopolymerizable composition comprising a blend of: (a) 30 to 70 wt. %, inclusive, of at least one urethane component; (b) 25 to 70 wt. %, inclusive, of at least one monofunctional reactive diluent, wherein the at least one monofunctional reactive diluent comprises at least one monofunctional reactive diluent having a $T_g$ of up to but not including 25 degrees Celsius; (c) optionally at least one difunctional reactive diluent in an amount of 1 to 30 wt. %, inclusive, if present, based on the total weight of the photopolymerizable composition; (d) 0.1 to 5 wt. %, inclusive, of at least one initiator; and (e) an optional inhibitor in an amount of 0.001 to 1 wt. %, inclusive, if present, based on the total weight of the photopolymerizable composition. One or more various optional post-processing steps 840 may be undertaken. Typically, remaining unpolymerized photopolymerizable component may be cured. In certain embodiments, the article comprises an orthodontic article. Preferably, the article exhibits an elongation at break of 25% or greater. Additionally, referring to FIG. 9, a method of making an article comprises receiving 910, by a manufacturing device having one or more processors, a digital object comprising data specifying a plurality of layers of an article; and generating 920, with the manufacturing device by an additive manufacturing process, the article based on the digital object. Again, the article may undergo one or more steps of post-processing 930, e.g., to cure unpolymerized urethane component and/or reactive diluent remaining in the article. Typically, the manufacturing device selectively cures a photopolymerizable composition to form the article.

ADDITIONAL EMBODIMENTS

Embodiment 1. A method of making an (e.g. orthodontic) article, the method comprising:
 a) providing a photopolymerizable composition as described herein; and
 b) selectively curing the photopolymerizable composition to form an article;
 c) optionally curing unpolymerized urethane component and/or reactive diluent remaining after step (b).

Embodiment 2. The method of Embodiment 1 further comprising (d) repeating steps (a) and (b) to form multiple layers and create the article having a three-dimensional structure prior to step (c).

Embodiment 3. The method of Embodiments 1-2 further comprising subjecting the article to heating in an oven.

Embodiment 4. The method of Embodiments 1-3 wherein the oven is set at a temperature of 60° C. or higher.

Embodiment 5. The method of Embodiments 1-4 wherein the article is subjected to stepwise heating to 60, 80 and then 100° C.

Embodiment 6. The method of Embodiments 1-5 wherein curing utilizes actinic radiation having a wavelength range of 375-400 nm.

Embodiment 7. The method of Embodiments 1-6 further including postcuring the article using actinic radiation or heat.

Embodiment 8. The method of Embodiments 1-7 wherein the postcuring the article using actinic radiation utilizes a wavelength range of 365 up to but not including 375 nm.

Embodiment 9. A non-transitory machine-readable medium comprising data representing a three-dimensional model of an orthodontic article, when accessed by one or more processors interfacing with a 3D printer, causes the 3D printer to create an article comprising a reaction product of a photopolymerizable compositions, as described herein.

Embodiment 10. A method comprising:
 retrieving, from a non-transitory machine readable medium, data representing a 3D model of an (e.g. orthodontic) article;
 executing, by one or more processors, a 3D printing application interfacing with a manufacturing device using the data; and
 generating, by the manufacturing device, a physical object of the article, the article comprising a reaction product of a photopolymerizable composition, as described herein.

Embodiment 11. A method comprising:
 receiving, by a manufacturing device having one or more processors, a digital object comprising data specifying a plurality of layers of an (e.g. orthodontic) article; and
 generating, with the manufacturing device by an additive manufacturing process, the article based on the digital object, the article comprising a reaction product of a photopolymerizable composition, as described herein.

Embodiment 12. A system comprising:
 a display that displays a 3D model of an (e.g. orthodontic) article; and
 one or more processors that, in response to the 3D model selected by a user, cause a 3D printer to create a physical object of an article, the article comprising a reaction product of a photopolymerizable composition, as described herein.

EXAMPLES

Unless otherwise noted, all parts, percentages, ratios, etc. in the Examples and the rest of the specification are by weight. Unless otherwise indicated, all other reagents were obtained, or are available from fine chemical vendors such as Sigma-Aldrich Company, St. Louis, Missouri, or may be synthesized by known methods. Table 1 (below) lists materials used in the examples and their sources.

TABLE 1

Materials List

| DESIGNATION | DESCRIPTION | SOURCE |
| --- | --- | --- |
| PE-1 | Urethane methacrylate prepared as described in PE-44 of U.S. patent application Ser. No. 62/736027; preparation procedure also described below. | |
| PE-2 | Urethane methacrylate prepared as described in PE-33 of U.S. patent application Ser. No. 62/736027; preparation procedure also described below. | |
| PE-3 | Urethane methacrylate prepared as described below; preparation procedure also described below. | |
| PP1 | Described in Example 2 of U.S. patent application Ser. No. 62/589707; preparation procedure also described below. | |
| IBOMA | Isobornyl methacrylate | San Esters Corp., New York, NY |
| EXOTH-10 | A urethane (meth)acrylate oligomer comprising a polyethylene oxide diol of about 400 MW, obtained under the trade designation EXOTHANE-10 | Esstech Inc., Essington, PA |
| EXOTH-108 | A urethane (meth)acrylate oligomer comprising a polytetramethylene oxide diol of about 650 MW, obtained under the trade designation EXOTHANE-108 | Esstech Inc. |
| IBOA | Isobornyl acrylate | Alfa Aesar |
| CHMA | Cyclohexyl methacrylate | Alfa Aesar |
| EHMA | 2-Ethyl hexyl methacrylate | Alfa Aesar |
| CN154 | Bisphenol A epoxy methacrylate oligomer obtained under the trade designation CN154 | Sartomer, Exton, PA |
| SR833S | Tricyclodecane dimethanol diacrylate obtained under the trade designation SR833S | Sartomer |
| Nanosilica filler | 20 nm nanosilica filler was prepared as described in U.S. Pat. No. 6572693 by surface treating NALCO 2327 according to the procedure described in column 21, lines 64 to 67. | |
| EBE-4859 | Difunctional aliphatic urethane methacrylate obtained under the trade designation EBECRYL 4859 | Allnex, Alphareta, GA |
| ESA-ONE | Difunctional alpha-OH ketone obtained under the trade designation ESACURE ONE | IGM Resins, Waalwijk, The Netherlands |
| LUP-231 | 1,1-Bis(tert-butylperoxy)-3,3,5-trimethylcyclohexane obtained under the trade designation LUPEROX 231 | Sigma-Aldrich Co., St. Louis, MO |
| IRG-2959-TRI | Prepared as described in U.S. patent application Ser. No. 62/460340. See section on the preparation of Pf3PI-B. | |
| IRG-TPO-L | 2,4,6-trimethylbenzoylphenyl phosphinate obtained under the trade designation IRGACURE TPO-L | BASF, Ludwigshafen, Germany |
| IRG-TPO | 2,4,6-trimethylbenzoyldiphenylphosphine oxide photoinitiator obtained under the trade designation IRGACURE TPO | BASF |
| IRG-651 | 2,2-Dimethoxy-1,2-diphenylethan-1-one obtained under the trade designation IRGACURE 651 | BASF |
| BHT | 2,6-di-t-butyl-4-methylphenol | Alfa Aesar |
| IRG-819 | Bis(2,4,6-trimethylbenzoyl)-phenylphosphineoxide obtained under the trade designation IRGACURE 819 | BASF |
| ESA-KIP 150 | Oligo[2-hydroxy-2-methyl-1-[4-(1-methylvinyl)phenyl]propanone] obtained under the trade designation ESACURE KIP150 | Lamberti, Hungerford, TX (currently available from IGM Resins, Waalwijk, The Netherlands) |
| NapA | Naphthalimide acrylate (NapA), prepared as described in U.S. patent application Ser. No. 62/736027 | |
| TIN-326 | 2-(5-chloro-2H-benzotriazol-2-yl)-6-(1,1-dimethylethyl)-4-methylphenol obtained under the trade designation TINUVIN 326 | BASF |
| C-2050 | A polycarbonate diol of about 1000 MW made with about a 9:1 mole ratio of 3-methyl-1,5-pentanediol (MPD):hexane diol (HD), (i.e., 90% MPD) obtained under the trade designation KURARAY POLYOL C-1090 | Kuraray Co. Ltd., Tokyo, Japan. |
| P-2010 | A 3-methyl-1,5-pentanediol (MPD) adipate polyester diol of about 2000 MW obtained as "KURARAY POLYOL P-2010" obtained from Kuraray Co. Ltd. | Kuraray Co. Ltd. |

TABLE 1-continued

Materials List

| DESIGNATION | DESCRIPTION | SOURCE |
|---|---|---|
| BiN | Bismuth neodeconate | Sigma-Aldrich Co. |
| DBTDL | Dibutyltin dilaurate | Sigma-Aldrich Co. |
| HEMA | Hydroxyethyl methacrylate | TCI America, Portland, OR |
| IBuMA | Isobutyl methacrylate | TCI America |
| PEMA | Phenoxy ethyl methacrylate under the trade name SR340 | Sartomer |
| IPDI | Isophorone diisocyanate, equivalent wt. 111.11, molecular wt. 222.22 g/mole, obtained under trade designation DESMODUR I | Covestro LLC, Leverkusen, Germany |
| XK-672 | Zn-based catalyst obtained under the trade designation K-KAT XK-672 | King Industries, Norwalk, CT |
| CHIV-300 | Oligo[2-hydroxy-2-methyl-1-[4-(1-methylvinyl)phenyl]propanone], obtained under the trade designation CHIVACURE 300 | Chitec, Taipei City, Taiwan. |
| EtOH | Ethanol | Spectrum Chemicals, New Brunswick, NJ. |
| Heptane | Heptane (Ultra resi-analyzed) | Avantor, Center Valley, PA. |
| ACN | Acetonitrile | EMD Millipore, Burlington, MA |
| IEA | 2-isocyanatoethylacrylate | Show Denko America Inc., New York, NY |
| Irgacure 2959 | 1-[4-(2-hydroxyethoxy)-phenyl]-2-hydroxy-2-methyl-1-propane-1-one obtained under the trade designation IRGACURE 2959 | BASF |
| AIBN | 2,2'-Azobis(2-methylpropionitrile) | Sigma-Aldrich Co. |

Test Methods

Additive Manufacturing of 3D Printed Parts

Unless otherwise noted, all 3D-printed examples were manufactured either on an Asiga Pico Plus or Asiga Max, a vat polymerization 3D printer available from Asiga USA, Anaheim Hills, CA.

Each formulation listed in Tables 5 to 12 was photopolymerized on an Asiga Max 3D printer with a LED light source of 385 nanometer (nm). Each formulation listed in Table 7 was photopolymerized on an Asiga Plus 3D printer with a LED light source of 405 nm. The dogbone shaped tensile test bars of Type V according to ASTM D638-14 (2014) and rectangular DMA bars were prepared via 3D printing. The resin bath of the printer was heated to 35-50° C. before photopolymerization to reduce the viscosity to prepare the tensile test bars. The following settings were used for the printing: slice thickness=50 micrometers (μm); burn in layers=1; separation velocity=1.5 millimeters per second (mm/s), separation distance=10 millimeters (mm), approach velocity=1.5 mm/s.

The printed parts were washed using propylene carbonate followed by isopropanol to remove unreacted resin. The printed part was then post-cured using a Clearstone 3200 UV chamber (365 nm, 385 nm, 405 nm LEDs—all of them switched on) for 5 minutes each side under nitrogen purge. EX-7 was post cured using Asiga Pico Flash post-curing chamber (obtained from Asiga USA, Anaheim Hills, CA) for 90 minutes each side. The parts were then heated in an oven at 100° C. for 30 minutes. When the secondary initiator was a thermal initiator, the printed parts were thermal cured at 120° C. for 24 hours followed by a UV post cure using a Clearstone 3200 UV chamber (365 nm, 385 nm, 405 nm LEDs—all of them switched on) for 5 minutes on each side, under a nitrogen purge. The dogbone specimens were conditioned in phosphate-buffered saline (PBS, diluted to 1× from 10× stock, pH=7.4) for 24 hours at 37° C. The DMA 3-point bend rectangular specimens were conditioned in de-ionized (DI) water for 48 hours at room temperature.

General Procedure of Formulation Casting and Curing

For Example 34 and Control 35 (EX-34 and CT-35), each formulation was poured into a silicone dogbone mold (Type V mold of 1 mm thickness, ASTM D638-14) for preparing tensile specimens, and a rectangular mold of dimensions (9.4 mm×25.4 mm×1 mm) for DMA 3-point bend test specimens. A 2 mil (0.05 mm) polyethylene terephthalate (PET) release liner (obtained under the trade designation "SCOTCHPAK" from 3M Company (St. Paul, MN)) was rolled on the filled mold, and the filled mold along with the liner was placed between two glass plates held by binder clips. The formulation was cured under a Asiga Pico Flash post-curing chamber (obtained from Asiga USA, Anaheim Hills, CA) for 30 minutes. The specimens were removed from the mold followed by additional light exposure for 30 minutes using the Asiga Pico Flash post-curing chamber. Specimens were then kept in an oven set at 100° C. for 30 minutes. The dogbone specimens were conditioned in phosphate-buffered saline (PBS, diluted to 1× from 10× stock, pH=7.4) for 24 hours at 37° C. The DMA 3-point bend rectangular specimens were conditioned in de-ionized (DI) water for 48 hours at room temperature.

For EX-37, the mixture was degassed and speed mixed in THINKY planetary mixer (Thinky Corporation, Tokyo, Japan), at 2000 rpm for 90 seconds under vacuum. The mixture was then poured in a silicone dogbone mold and cured in Asiga Pico Flash post-curing device for 15 minutes. The dogbones were demolded and cured for another 15 minutes in the chamber. The dogbones were kept in a vacuum oven at 100° C. overnight to remove any residual unreacted monomer. The dogbones were subjected to an additional UV cure for 10 mins in presence of germicidal lamp (GE G30T8, 30 W bulb).

General Procedure for Tensile Testing

PBS conditioned dogbone specimens were tested on an Instron 5944 testing system (Instron, Norwood, MA) with a 500 Newton (N) load cell. The test speed was 5 mm/minute, and the initial grip separation was 1 inch. The gauge length was set to 1 inch (2.5 cm). Five replicate samples for each formulation were tested, and the average values are reported. The tensile strength at yield was determined according to ASTM D638-14 (2014). Elongation at break was determined from the crosshead movement of the grips. Tensile strength at yield, maximum tensile strength, and elongation at break are shown in Table 13.

Dogbone specimens for EX-37 were tested on an Insight MTS with 5 kN load cell at the rate of 5 mm/minute. Five replicate samples were tested, and the average and standard deviation are reported. The tensile strength was determined according to ASTM D638-10. Elongation at break was determined from the crosshead movement of the grips and the samples were not strain gauged. These dogbone specimens were not conditioned in PBS.

General Procedure for the Determination of 3-Point Bend at 2% Strain Modulus Using Dynamic Mechanical Analysis DMA rectangular specimens were water conditioned by soaking in deionized water for 48 hours at a temperature of 22 to 25° C. and were tested in a TA instruments Q800 DMA equipped with a submersion 3-point bending clamp with a 15 mm span. The water conditioned rectangular specimens were placed in water filled submersion fixture, and were equilibrated for 10 minutes at 37° C. A displacement rate of 8.5 mm/min was used to apply a 2% strain and the 3-point bend modulus at 2% stain was measured immediately using TA advantage software. The data is reported in Table 13.

Test Procedure for Gravimetric Analysis of Extractables from Printed Articles

Articles shaped as a continuous 5-tooth row (30.4 mm×9.24 mm×8.17 mm) using formulations selected from Tables 5, 8, and 10 were printed. The printed parts were washed using propylene carbonate followed by isopropanol to remove unreacted resin. The printed articles were then post cured in a Clearstone 3200 UV chamber (365 nm, 385 nm, 405 nm LEDs—all of them switched on) for 15 minutes each side under nitrogen purge. When the secondary initiator was a thermal initiator, the printed parts were thermal cured at 120° C. for 24 hours followed by UV post cure in a Clearstone 3200 UV chamber (365 nm, 385 nm, 405 nm LEDs—all of them switched on) for 15 minutes on each side, under nitrogen purge. The thickness of the article was 0.49 mm. Three of the 5-tooth articles (total surface area of 45 cm$^2$) were placed in a 40 milliliter (mL) glass vial and weighed. 15 mL of solvent (either heptane or 5% ethanol/Milli-Q water) was added to the vial, with one 15 mL blank (vial without articles) for each solvent. The vials were covered with TEFLON caps, and the samples were kept at 37° C. for 24 hours while shaking at 80 revolutions per minute (RPM) in a LabLine Benchtop incubated shaker, Model No. 4628. The samples were allowed to cool before transferring the extraction solution to a new 20 mL glass vial. A 5 mL aliquot was transferred to a pre-weighed 8 mL glass vial and set to evaporate under a nitrogen purge. The vials were then weighed once the solvent evaporated, until a constant weight was reached. % Residue was calculated using the formula below. The test was completed in triplicates, all run at the same time, and results shown are the average of the three replicates.

$$\% \text{ Residue} = \left[\frac{(\text{vial after evaporation }(g) - \text{vial tare}(g)) * (15 \text{ mL solvent})}{(\text{mass of article }(g)) * (5 \text{ mL solvent analyzed})}\right] * 100$$

UV-VIS Measurements of Photoinitiators 1 g/L of photoinitiator in ACN (Acetonitrile) was taken in a spectrophotometer cuvette (obtained from Starna Cells Inc, Atascadero, CA) of 10 mm pathlength. A CARY 60 UV-Vis spectrometer (Agilent, Santa Clara, CA) was used to measure the UV-VIS spectrum of photoinitiator solutions. UV-VIS absorbances at desired wavelengths are reported in Tables 2 and 3, below.

TABLE 2

| UV-VIS absorbances | |
|---|---|
| Photoinitiator | Absorbance measured at 385 nm at 1 g/L |
| TPO | 1.5 |
| IRG-TPO-L | 0.5 |

TABLE 3

| UV-VIS absorbances | | |
|---|---|---|
| Photoinitiator | Absorbance measured (385 nm) at 1 g/L | Absorbance measured (365 nm) at 1 g/L |
| ESA-KIP 150 | 0.01 | 0.1 |
| CHIV-300 | 0.01 | 0.1 |
| IRG-2959-TRI | 0.01 | 0.1 |

Examples

PE—indicates a preparative example, EX—indicates an example, and CT—indicates a control.

Preparation of Polymer with Pendant Photoinitiator (PP1)

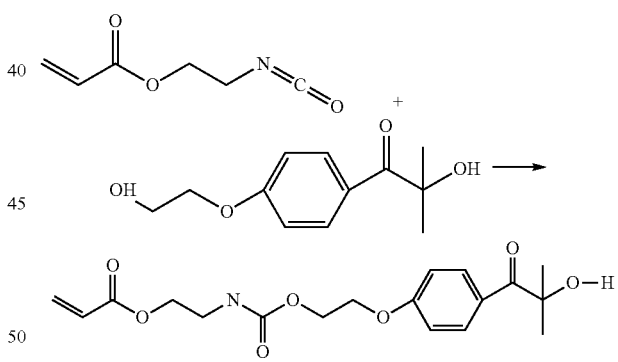

A preparation of PIEA was produced as the product of Irgacure 2959 and 2-isocyanatoethylacrylate (IEA), according to the chemical reaction above. Irgacure 2959 (50.29 g, 224.3 mmol) was dissolved in acetone (150 mL, GFS Chemicals Inc., Powell, OH, USA). Dibutyltindilaurate (0.5 g, 0.8 mmol) and BHT (0.2 g, 0.9 mmol) were added, followed by the incremental addition of 2-isocyanatoethyl acrylate (IEA, 3015 g, 213.6 mmol), over 20 minutes with continuous stirring. Samples were taken and the IR spectrum was recorded. After 2-hour reaction time, NCO band (~2200-2500 cm-1) disappeared indicating reaction completion. The solvent was removed in a rotary evaporator followed by further drying under vacuum to give a hazy viscous liquid. The reaction yield was 99.7%.

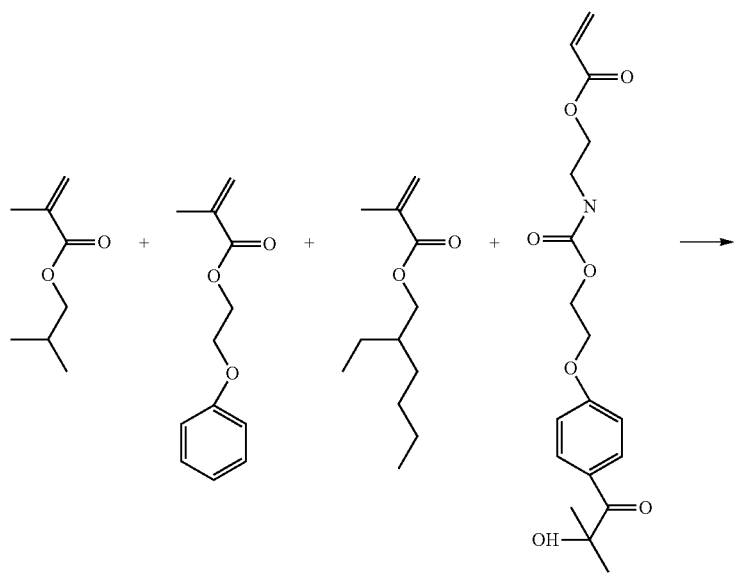

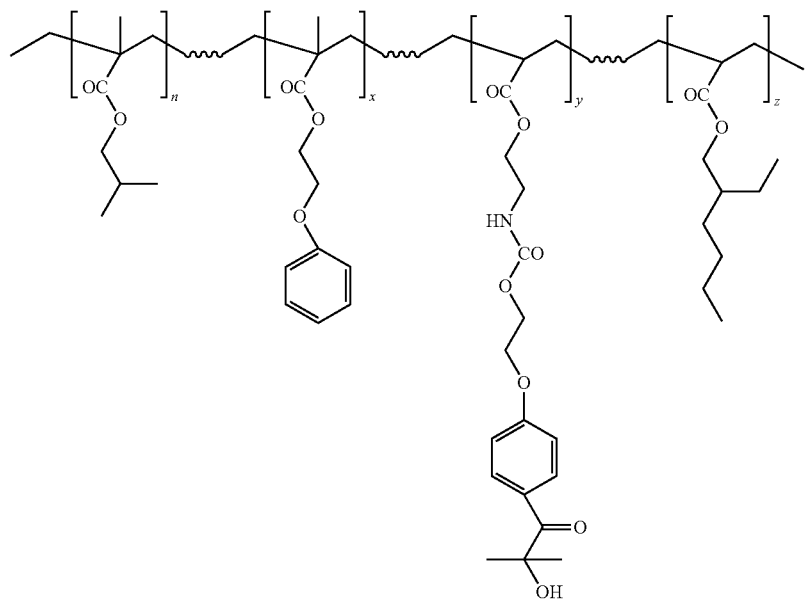

A photo-initiator-carrying polymer (PP1) was prepared per the chemical reaction above. Isobutyl methacrylate (10 g, 70.32 mmol), 2-phenoxyethyl methacrylate (PEMA) (10.47 g, 50.77 mmol), 2-ethyhexyl methacrylate (10.65 g, 53.71 mmol), and PIEA (10.56 g, 28.9 mmol, an adduct of 2-isocyanatoethyl acrylate and Irgacure-2959) were dissolved in isopropyl alcohol (75 mL, GFS Chemicals Inc., Powell, OH, USA) in a 250 mL 3-neck flask equipped with a stirring bar, a condenser, a thermocouple and a stream of $N_2$ bubbling into the solution. 2,2'-Azobis(2-methylpropionitrile) ((AIBN), 0.25 g, 1.5 mmol) was added. After bubbling $N_2$ through the solution for 15 minutes, the heat was raised to 65° C. and stirred overnight. The next day, the heat was turned off and the solution was allowed to cool to room temperature. The solvent was decanted off the product to obtain a moist product, which was then dried under vacuum to give a sticky semi-solid.

The molecular weight of PP1 was determined with gel permeation chromatography (HPLC 1260 from Agilent Technologies (Santa Clara, CA) operated at a flow rate of 1.0 mL/min using tetrahydrofuran as eluent. The GPC column set consisted of a PLgel MIXED-B and a PLgel MIXED-C in series (300 mm length×7.5 mm internal diameter) each from Agilent Technologies. The column compartment and differential refractive index detector were set to 40° C. The data were analyzed using Agilent GPC/SEC software from Agilent Technologies.

The sample was prepared singly and injected in duplicate. A solution of approximate concentration 3 mg/mL was prepared in a glass scintillation vial using tetrahydrofuran (Non-UV stabilized with 250 parts per million BHT, Omnisolv® grade, from EMD Millipore Corporation) as solvent. The sample solution was filtered through a 0.45 micrometer pore size PTFE syringe filter (Fisherbrand) and placed into an autosampler vial that was tightly crimped. This solution was placed into the autosampler of the GPC system for analysis. The injection volume was set to 60 μL.

The molecular weight standards were EasiCal Polystyrene from Agilent Technologies (Batch Number 0006308830. The Mp values of the polystyrene molecular weight standards used in the calibration curve ranged from 580 g/mol to 6,570,00 g/mol.

The results were as follows: Mn=24,900 g/mole, Mw=206,000 g/mole, polydispersity 8.25.

Preparative Examples for Polyurethane Methacrylates (PE-1 to PE-3):

Synthesis of PE-1 has been described in PE-44 of U.S. Pat. App. 62/736,027. PE-1 was prepared as follows. A 1 liter (L) three-necked round-bottom flask was charged with 1100.8 g C-2050 (OH equivalent weight 984.2), heated to about 45° C., then were added 248.55 g IPDI, 0.6 g BHT, and 0.375 g XK-672. The reaction was heated under dry air to an internal setpoint of 105° C. (temperature reached at about 20 min). At 1 hour and 20 minutes 150.65 g HEMA was added via an addition funnel at a steady rate over 1 hour and 10 minutes. The reaction was heated for about 2.5 hours at 105° C., then an aliquot was checked by Fourier transform infrared spectroscopy (FTIR) and found to have no —NCO peak at 2265 cm-1 and the product was isolated as a clear, viscous material.

Synthesis of PE-2 has been described in PE-33 of U.S. Pat. App. 62/736,027. PE-2 was prepared as follows. A 1 L three-necked round-bottom flask was charged with 319.80 g IPDI (2.878 eq), 0.280 g BHT, and 0.175 g bismuth neodecanoate (250 ppm based on solids) and heated to an internal temperature of about 55° C. under dry air. Then 380.20 g (2.921 eq) HEMA was added over 1 hour and 45 minutes, with the internal temperature rising to a maximum of 90° C. At 2 hours and 25 minutes an aliquot was checked by FTIR and found to have no —NCO peak at 2265 cm$^{-1}$.

PE-3 was prepared as follows. A 3 liter (L) three-necked round-bottom flask was charged with 1475.29 grams (g) heated polyester diol P-2010 (1.462 eq, 1009 hydroxyl equivalent weight (OH EW)), 324.91 g IPDI (2.9242 eq), 0.800 g BHT (400 ppm), and 0.500 XK-672 (250 ppm). The reaction of initial temperature 60° C., was heated under dry air to an internal setpoint of 100° C. (temperature reached at about 50 min). At 1 hour and 1 minutes, 199.80 g HEMA (1.5352 eq, 130.14 MW, a 5% stoichiometric excess) was added via an addition funnel at a steady rate over 30 minutes. At 6.5 hours into the reaction, an aliquot was checked by Fourier transform infrared spectroscopy (FTIR) and found to have no —NCO peak at 2265 cm$^{-1}$. The product was poured out of the flask as a clear, viscous material.

This reaction scheme can also produce diisocyanate capped with (meth)acrylate mono-ols as a by-product.

TABLE 4

Formulations of Urethane Methacrylates (in grams)

| EXAMPLE | IPDI, g | C-2050, g | P-2010, g | HEMA, g | XK-672, g | BiN, g | BHT, g |
|---|---|---|---|---|---|---|---|
| PE-1 | 248.55 | 1100.8 | | 150.65 | 0.375 | | 0.6 |
| PE-2 | 319.8 | | | 380.2 | | 0.175 | 0.28 |
| PE-3 | 324.91 | | 1475.29 | 199.8 | 0.5 | | 0.8 |

Preparation of Formulated Resins:

Formulations were prepared by weighing the components (as indicated in Tables 5-12) in an amber glass jar, followed by rolling on a roller (obtained under the trade designation OLDE MIDWAY PRO18 from Olde Midway) until mixed. Some formulations were heated to 60° C. for complete mixing.

TABLE 5

Formulations of Resins (in parts by weight)

| COMPONENTS | CT-1 | CT-2 | EX-3 | EX-4 | EX-5 | EX-6 | EX-7 |
|---|---|---|---|---|---|---|---|
| PE-1 | 50 | 50 | 50 | 50 | 50 | 50 | 50 |
| Isobornyl methacrylate | 50 | 50 | 50 | 50 | 50 | 50 | 50 |
| IRG-TPO | 0.5 | 2 | 0.5 | 0.5 | 0.5 | 0.5 | 0.5 |
| ESA-KIP 150 | | | | 0.5 | | | |
| ESA-ONE | | | | | 0.5 | | |
| IRG-651 | | 0.5 | | | | | |
| IRG-2959-TRI | | | | | | | 0.5 |
| LUP-231 | | | | | | 1.0 | |
| BHT | 0.025 | 0.025 | 0.025 | 0.025 | 0.025 | 0.025 | 0.025 |
| NapA | 0.1 | 0.0.25 | 0.1 | 0.1 | 0.1 | 0.1 | 0.1 |

TABLE 6

Formulations of Resins (in parts by weight)

| COMPONENTS | CT-8 | EX-9 | CT-10 | EX-11 |
|---|---|---|---|---|
| PE-1 | 50 | 50 | 50 | 50 |
| Isobornyl methacrylate | 50 | 50 | 50 | 50 |
| IRG-TPO-L | 0.5 | 0.5 | | |
| IRG-819 | | | 0.5 | 0.5 |
| ESA-KIP 150 | | 0.5 | | 0.5 |
| BHT | 0.025 | 0.025 | 0.025 | 0.025 |
| NapA | 0.1 | 0.1 | 0.1 | 0.1 |

TABLE 7

Formulations of Resins (in parts by weight)*

| COMPONENTS | CT-12 | EX-13 |
|---|---|---|
| PE-1 | 50 | 50 |
| Isobornyl methacrylate | 50 | 50 |
| IRG-TPO | 0.5 | 0.5 |
| ESA-KIP 150 | | 0.5 |
| BHT | 0.025 | 0.025 |
| NapA | 0.1 | 0.1 |

*Printed using a 3D printer wavelength of 405 nm.

TABLE 8

Formulations of Resins (in parts by weight)

| COMPONENTS | EX-14 | EX-15 | EX-16 | EX-17 | CT-18 | EX-19 |
|---|---|---|---|---|---|---|
| PE-2 | | | | | 7.8 | 7.8 |
| PE-1 | 50 | 50 | 50 | 50 | 44.7 | 44.7 |
| Isobornyl methacrylate | 50 | 50 | 50 | 50 | 47.5 | 47.5 |
| IRG-TPO | 0.5 | 0.5 | 0.5 | 2 | 0.5 | 0.5 |
| ESA-KIP 150 | 1.0 | 1.5 | 2.0 | 2 | | 0.5 |
| BHT | 0.025 | 0.025 | 0.025 | 0.025 | 0.025 | 0.025 |
| NapA | 0.1 | 0.1 | 0.1 | 0.1 | 0.1 | 0.1 |

TABLE 9

Formulations of Resins (in parts by weight)

| COMPONENTS | CT-20 | EX-21 | CT-22 | EX-23 | CT-24 | EX-25 | CT-26 | EX-27 |
|---|---|---|---|---|---|---|---|---|
| EBE-4859 | 20 | 20 | | | | | | |
| EXOTH-10 | | | 50 | 50 | | | | |
| EXOTH-108 | 40 | 40 | | | 40 | 40 | 40 | 40 |
| CN154 | | | | | 20 | 20 | | |
| SR833S | | | | | | | 20 | 20 |
| Isobornyl methacrylate | 20 | 20 | | | 20 | 20 | 20 | 20 |
| EHMA | 20 | 20 | 15 | 15 | 20 | 20 | 20 | 20 |
| CHMA | | | 35 | 35 | | | | |
| IRG-TPO | 0.5 | 0.5 | 0.5 | 0.5 | 0.5 | 0.5 | 0.5 | 0.5 |
| ESA-KIP 150 | | 0.5 | | 0.5 | | 0.5 | | 0.5 |
| BHT | 0.025 | 0.025 | 0.025 | 0.025 | 0.025 | 0.025 | 0.025 | 0.025 |
| NapA | 0.1 | 0.1 | 0.1 | 0.1 | 0.1 | 0.1 | 0.1 | 0.1 |

TABLE 10

Formulations of Resins (in parts by weight)

| COMPONENTS | CT-28 | EX-29 | CT-30 | EX-31 |
|---|---|---|---|---|
| PE-1 | | | 50 | 50 |
| EXOTH-10 | 50 | 50 | | |
| Isobornyl methacrylate | | | 50 | 50 |
| IBOA | 50 | 50 | | |
| IRG-TPO | 0.5 | 0.5 | 0.5 | 0.5 |
| ESA-KIP 150 | | 0.5 | | |
| CHIV-300 | | | | 0.5 |
| BHT | 0.025 | 0.025 | 0.025 | 0.025 |
| NapA | 0.1 | 0.1 | | |
| TIN-326 | | | 0.1 | 0.1 |

TABLE 11

Formulations of Resins (in parts by weight)

| COMPONENTS | CT-32 | EX-33 |
|---|---|---|
| PE-3 | 50 | 50 |
| Isobornyl methacrylate | 50 | 50 |
| IRG-TPO | 0.5 | 0.5 |
| CHIV-300 | | 0.5 |
| BHT | 0.025 | 0.025 |
| TIN-326 | 0.1 | 0.1 |

TABLE 12

Formulations of Resins (in parts by weight)

| COMPONENTS | EX-34** | CT-35** | EX-36 | EX-37* |
|---|---|---|---|---|
| EXOTH-108 | 38 | 30 | 38 | |
| EXOTH-10 | | | | 50 |
| EBE-4859 | 19 | 15 | 19 | |
| Isobornyl methacrylate | 19 | 15 | 19 | |
| IBuMA | | | | 13.33 |
| EHMA | 19 | 15 | 19 | 13.33 |
| PEMA | | | | 13.33 |
| Nanosilica Filler | 5 | 25 | 5 | |
| IRG-TPO | 0.5 | 0.5 | 0.5 | 2 |

TABLE 12-continued

Formulations of Resins (in parts by weight)

| COMPONENTS | EX-34** | CT-35** | EX-36 | EX-37* |
|---|---|---|---|---|
| PP1 | | | | 10 |
| ESA-KIP 150 | 0.5 | 0.5 | 0.5 | |
| BHT | | | 0.025 | 0.025 |
| NapA | | | 0.1 | |

*EX-37 is the same as E-16 in U.S. patent application Ser. No. 62/589707;
**Formulations were molded and then cured as described in the general procedure of formulation casting and curing above.

TABLE 13

Mechanical Analysis of Printed Articles

| EXAMPLE | Yield strength, MPa | Maximum Tensile strength, MPa | % Elongation at break | 3-Point Bend Modulus, MPa |
|---|---|---|---|---|
| CT-1 | 21.2 | 27.2 | 103.0 | 666.5 |
| CT-2* | 24.2 | 27.5 | 81.5 | 700.7 |
| EX-3 | 25.8 | 27.8 | 74.1 | 724.9 |
| EX-4 | 27.9 | 28.7 | 84.3 | 771.6 |
| EX-5 | 23.5 | 26.4 | 71.3 | 720.0 |
| EX-6 | 25.3 | 29.3 | 74.4 | 601.1 |
| EX-7 | 24.0 | 28.9 | 105.6 | 740.8 |
| CT-8 | 22.4 | 25.2 | 69.2 | 695.1 |
| EX-9 | 24.4 | 28.7 | 82.5 | 671.7 |
| CT-10 | 26.9 | 34.7 | 100.8 | 778.8 |
| EX-11 | 28.8 | 30.4 | 67.0 | 828.7 |
| CT-12 | 21.6 | 24.4 | 74.0 | 709.3 |
| EX-13 | 29.4 | 30.9 | 58.7 | 837.6 |
| EX-14 | 27.8 | 28.3 | 81.4 | 826.4 |
| EX-15 | 28.3 | 30.0 | 71.9 | 828.1 |
| EX-16 | 24.5 | 26.5 | 75.9 | 708.2 |
| EX-17 | 25.7 | 29.5 | 86.1 | 729.2 |
| CT-18 | 33.1 | 33.1 | 38.3 | 773.9 |
| EX-19 | 37.9 | 37.9 | 21.5 | 940.9 |
| CT-20 | DNY | 14.7 | 20.0 | 204.0 |
| EX-21 | 17.6 | 17.8 | 19.3 | 370.5 |
| CT-22 | 16.8 | 17 | 30.1 | 218.2 |
| EX-23 | 20.2 | 20.2 | 27.7 | 243.1 |
| CT-24 | 20.3 | 20.3 | 14.1 | 383.7 |
| EX-25 | 25.5 | 25.5 | 13.4 | 500.7 |
| CT-26 | DNY | 17.6 | 14.1 | 414.1 |
| EX-27 | 22.2 | 22.2 | 10.5 | 639.1 |
| CT-28 | 15.2 | 15.2 | 17.0 | 317.7 |
| EX-29 | 26.3 | 26.3 | 16.2 | 637.7 |
| CT-30 | 27.2 | 31.4 | 79.4 | 752.8 |
| EX-31 | 30.9 | 38.2 | 94.5 | 694.1 |
| CT-32 | 18.1 | 23.0 | 94.2 | 556.6 |
| EX-33 | 18.4 | 26.5 | 120.5 | 586.9 |
| EX-34** | 28.4 | 28.4 | 11.5 | 406.4 |
| CT-35** | 32.4 | 32.4 | 6.2 | 417.8 |
| EX-36 | 17.9 | 19.1 | 24.8 | 271.0 |

DNY: Did not yield;
*Results are reported as an average of two measurements taken from printed articles prepared from formulation CT-2 using different batches of PE-1;
**Indicates molded and cured formulations.

TABLE 14

Mechanical Analysis of EX-37

| EXAMPLE | Tensile strength, MPa | Tensile Modulus, MPa | Elongation at break, % | Viscosity, Pa·s** |
|---|---|---|---|---|
| EX-37* | 34.4 | 1205.8 | 98 | 0.163 |

*EX-37 is the same as E-16 in U.S. patent application Ser. No. 62/589707;
**Absolute (e.g., dynamic) viscosity of the EX-37 was measured using a TA Instruments AR-G2 magnetic bearing rheometer using a 40 millimeter cone and plate measuring system at 40° C. at a shear rate of 0.1 1/s. Two replicates were measured and the average value was reported as the viscosity, in Pa·s.

TABLE 15

Analysis of Extractables from Printed Articles

| EXAMPLE | % Extractable in Heptane | % Extractable in 5% EtOH/H$_2$O |
|---|---|---|
| CT-2* | 0.521 | 0.047 |
| CT-1 | 0.217 | 0.046 |
| CT-30 | 0.304 | 0.051 |
| EX-4 | 0.232 | 0.045 |
| EX-16 | 0.273 | 0.04 |
| EX-6 | 0.234 | 0.070 |

*The article prepared for CT-2 in the extractable test was prepared with a separate but identical formulation as represented in Table 4.

Additive Manufacturing of Aligner Articles from the Formulated Resin

Polymerizable composition EX-31 of Table 10 was photopolymerized on the Asiga Max printer with a LED light source of 385 nm. A stereolithography file format (STL file) of the aligner was loaded into the Asiga Composer software, and support structures were generated. The resin bath of the printer was heated to 40° C. before photopolymerization to reduce the viscosity to be able to manufacture the article. The following settings were used for the printing: slice thickness=50 μm; burn in layers=1; separation velocity=1.5 mm/min, burn-in exposure time=10 sec; exposure time=3 sec. The printed part was washed using propylene carbonate followed by isopropanol to remove unreacted resin. The printed specimen was then post-cured using an Clearstone 3200 post-curing chamber for 15 minutes on each side. The photopolymerized aligner fits the model.

All cited references, patents, and patent applications in the above application for letters patent are herein incorporated by reference in their entirety in a consistent manner. In the event of inconsistencies or contradictions between portions of the incorporated references and this application, the information in the preceding description shall control. The preceding description, given in order to enable one of ordinary skill in the art to practice the claimed disclosure, is not to be construed as limiting the scope of the disclosure, which is defined by the claims and all equivalents thereto.

What is claimed is:

1. An orthodontic article comprising a cured composition comprising
   a free-radically polymerizable resin comprising a urethane (meth)acrylate comprising polymerized units derived from a diol selected from polycarbonate diol or polyester diol;
   a first free-radical photoinitiator having sufficient absorbance at a first wavelength range; and
   a second free-radical initiator selected from a second photoinitiator having sufficient absorbance at a second wavelength range, wherein the second wavelength range is different than the first wavelength range, or a thermal free-radical initiator.

2. The orthodontic article of claim 1 wherein a 1 g/liter acetonitrile solution of the first free-radical photoinitiator, at a pathlength of 1 cm, has an absorbance of greater than 0.01 at a wavelength of 385 nm when measured with a spectrophotometer.

3. The orthodontic article of claim 1 wherein a 1 g/liter acetonitrile solution of the first free-radical photoinitiator, at a pathlength, of 1 cm has an absorbance of greater than 0.2 for a 1 g/liter solution of the first free-radical photoinitiator in acetonitrile at a wavelength of 385 nm when measured with a spectrophotometer.

4. The orthodontic article of claim 1 wherein the first free-radical photoinitiator has a maximum absorbance at a wavelength of the range of 370-380 nm or 320-330 nm.

5. The orthodontic article of claim 1 wherein the first free-radical photoinitiator comprises photoinitiator groups selected from acyl phosphine oxide or alkyl amine acetophenone.

6. The orthodontic article of claim 1 wherein the second free-radical initiator is a thermal initiator.

7. The orthodontic article of claim 1 wherein a 1 g/liter acetonitrile solution of the second photoinitiator, at a pathlength of 1 cm, has an absorbance of greater than 0.01 at a wavelength of 365 nm when measured with a spectrophotometer.

8. The orthodontic article of claim 1 wherein the second photoinitiator has a maximum absorbance at a wavelength of the range 325-330 nm.

9. The orthodontic article of claim 1 wherein the second photoinitiator comprises photoinitiator groups selected from benzil ketal or hydroxy-acetophenone.

10. The orthodontic article of claim 1 wherein a 1 g/liter acetonitrile solution of the second photoinitiator, at a pathlength of 1 cm, has an absorbance of less than 0.1 at a wavelength of 365 nm.

11. The orthodontic article of claim 1 wherein the composition comprises 0.1 to 5 wt. % of photoinitiators based on the total weight of the polymerizable composition.

12. The orthodontic article of claim 1 wherein the polymerizable composition further comprises an ultraviolet absorber.

13. The orthodontic article of claim 1 wherein the free-radically polymerizable resin comprises 25 to 70 wt. % of at least one monofunctional reactive diluent.

14. The orthodontic article of claim 13 wherein the monofunctional reactive diluent comprises at least one monofunctional reactive diluent having a $T_g$ of 25 degrees Celsius or greater.

15. The orthodontic article of claim 13 wherein the monofunctional reactive diluent comprises at least one monofunctional reactive diluent where a homopolymer thereof has a $T_g$ of 60 degrees Celsius or greater.

16. The orthodontic article of claim 13 wherein the monofunctional reactive diluent comprises at least one monofunctional reactive diluent having a log P value of greater than 1.5.

17. The orthodontic article of claim 13 wherein the orthodontic article comprises less than 0.1 wt.-% extractables in a solution of 5% ethanol in water.

18. The orthodontic article of claim 1 wherein the cured composition exhibits an elongation at break of 15% or greater and a tensile strength at yield of at least 10 MPa as determined according to ASTM D638-14 after conditioning in phosphate-buffered saline having a pH of 7.4 for 24 hours at a temperature of 37° C.

19. The orthodontic article of claim 1 wherein the cured composition polymerized composition exhibits a 3-point bend modulus of at least 100 MPa as determined according to dynamic mechanical analysis at 2% strain after conditioning in deionized water at 20-25° C. for 48 hours.

20. The orthodontic article of claim 1 wherein the orthodontic article is orthodontic tray aligner article.

* * * * *